US011446388B2

(12) United States Patent
Hechler et al.

(10) Patent No.: US 11,446,388 B2
(45) Date of Patent: Sep. 20, 2022

(54) AMANITIN ANTIBODY CONJUGATES

(71) Applicant: Heidelberg Pharma Research GmbH, Ladenburg (DE)

(72) Inventors: Torsten Hechler, Ladenburg (DE); Michael Kulke, Ladenburg (DE); Christian Lutz, Ladenburg (DE); Andreas Pahl, Ladenburg (DE); Christoph Müller, Ladenburg (DE); Werner Simon, Ladenburg (DE); Anikó Pálfi, Ladenburg (DE)

(73) Assignee: HEIDELBERG PHARMA RESEARCH GMBH, Ladenburg (DE)

( * ) Notice: Subject to any disclaimer, the term of this patent is extended or adjusted under 35 U.S.C. 154(b) by 448 days.

(21) Appl. No.: 16/470,950

(22) PCT Filed: Dec. 22, 2017

(86) PCT No.: PCT/EP2017/084431
§ 371 (c)(1),
(2) Date: Jun. 18, 2019

(87) PCT Pub. No.: WO2018/115466
PCT Pub. Date: Jun. 28, 2018

(65) Prior Publication Data
US 2019/0328899 A1    Oct. 31, 2019

(30) Foreign Application Priority Data

Dec. 23, 2016    (EP) ..................................... 16206849

(51) Int. Cl.
*A61K 47/68*    (2017.01)
*A61P 35/00*    (2006.01)
(Continued)

(52) U.S. Cl.
CPC ...... *A61K 47/6831* (2017.08); *A61K 47/6867* (2017.08); *A61K 47/6889* (2017.08);
(Continued)

(58) Field of Classification Search
None
See application file for complete search history.

(56) References Cited

U.S. PATENT DOCUMENTS 5,939,598 A    8/1999   Kucherlapati et al.
6,214,345 B1   4/2001   Firestone et al.
(Continued)

FOREIGN PATENT DOCUMENTS

EP    1859811        * 11/2007
EP    1859811 B1      11/2007
(Continued)

OTHER PUBLICATIONS

Palfi et al., European Journal of Cancer, 2016, vol. 69, suppl. 1, p. S24 (Year: 2016).*
(Continued)

*Primary Examiner* — Karl J Puttlitz
(74) *Attorney, Agent, or Firm* — Ballard Spahr LLP

(57) ABSTRACT

The invention relates to a conjugate comprising (a) an amatoxin comprising (i) an amino acid 4 with a 6'-deoxy position; and (ii) an amino acid 8 with an S-deoxy position; (b) a BCMA-binding moiety comprising (i) the variable domains of humanized antibody J22.9-ISY, and (ii) a heavy chain constant region comprising a D265C mutation; and (c) a protease-cleavable linker linking said amatoxin and said target-binding moiety. The invention furthermore relates to a pharmaceutical composition comprising such conjugate, particularly for use in the treatment of multiple myeloma.

3 Claims, 32 Drawing Sheets
Specification includes a Sequence Listing.

(51) Int. Cl.
  *C07K 14/37* (2006.01)
  *C07K 16/28* (2006.01)
(52) U.S. Cl.
  CPC .............. *A61P 35/00* (2018.01); *C07K 14/37* (2013.01); *C07K 16/2878* (2013.01)

(56) References Cited

U.S. PATENT DOCUMENTS

| | | |
|---|---|---|
| 2011/0256157 A1 | 10/2011 | Howard et al. |
| 2014/0161828 A1 | 6/2014 | Armitage et al. |

FOREIGN PATENT DOCUMENTS

| | | | |
|---|---|---|---|
| WO | WO-2010/115290 A1 | 10/2010 | |
| WO | WO-2010/115629 A2 | 10/2010 | |
| WO | WO-2010/115630 A1 | 10/2010 | |
| WO | WO 2012/119787 A1 | 9/2012 | |
| WO | WO-2014/009025 A1 | 1/2014 | |
| WO | 2014068079 | * 5/2014 | |
| WO | WO-2014/068079 A1 | 8/2014 | |
| WO | WO 2014/135282 A1 | 9/2014 | |
| WO | 2015166073 | * 11/2015 | |
| WO | WO-2015/166073 A1 | 11/2015 | |
| WO | WO 2016/062855 A1 | 4/2016 | |
| WO | WO 2016/062857 A1 | 4/2016 | |
| WO | 2016142049 | * 9/2016 | |
| WO | WO-2016/142049 A1 | 9/2016 | |
| WO | WO-2017/149077 A1 | 9/2017 | |
| WO | WO-2017/219029 A2 | 12/2017 | |

OTHER PUBLICATIONS

Palf et al., [Abstract], In: Proceedings of the 107th Annual Meeting of the American Association for Cancer Research; Apr. 16-20, 2016; New Orleans, LA. Philadelphia (PA): AACR; Cancer Res 2016;76(14 Suppl):Abstract nr 2973 (Year: 2016).*
Zhao et al., ChemBioChem 2015, 16, 1420-1425 (Year: 2015).*
Database Caplus Chemical Abstracts Service, Columbus, Ohio, US; Registry No. 1870916-87-2, L-Alaninamide, N-[6-(2,5-dihydro-2,5-dioxo-1H-pyrrol-1-yl)-1-oxohexyl]-L-valyl-N-[4-(hydroxymethyl)phenyl], Mc-Val-Ala-PAB, Entered STN: Feb. 19, 2016 (Year: 2016).*
Ackerman M E et al. A robust, high-throughput assay to determine the phagocytic activity of clinical antibody samples. J Immunol Methods. Mar. 7, 2011; 366(1-2): 8-19.
Baudino L et al. Crucial role of aspartic acid at position 265 in the CH2 domain for murine IgG2a and IgG2b Fc-associated effector functions. J Immunol. Nov. 1, 2008; 181(9):6664-9.
Belucci R et al. Graft-versus-tumor response in patients with multiple myeloma is associated with antibody response to BCMA, a plasma-cell membrane receptor. Blood. May 15, 2005; 105(10):3945-5.
Bird J M et al. Guidelines for the diagnosis and management of multiple myeloma 2011. Br J Haematol. Jul. 2011; 154(1):32-75.
Bossen C, Schneider P. Baff, April and their receptors: structure, function and signaling. Semin Immunol. Oct. 2006; 18(5):263-75.
Chesi M, Bergsagel P L. Advances in the pathogenesis of multiple myeloma. Int J Lab Hematol. May 2015; 37 Suppl 1:108-14.
Davis M B, Preston J F. A Conjugate of a-amanitin and Monoclonal Immunoglobulin G to Thy 1.2 Antigen is Selectively Toxic to T Lymphoma Cells. Science 213 (1981) 1385-1388.
Dimopoulos Ma et al. Current treatment landscape for relapsed and/or refractory multiple myeloma. Nat Rev Clin Oncol. Jan. 2015; 12(1):42-54.
Dimopoulos Ma et al.: "Pathogenesis and treatment of renal failure in multiple myeloma", LEUKEMIA, vol. 22, No. 8, Aug. 2008 (Aug. 1, 2008), pp. 1485-1493.
Hayes J M et al. Glycosylation and Fc receptors. Curr Top Microbiol Immunol. 2014; 382:165-99.
Holliger P. et al.,"Diabodies": Small Bivalent and Bispecific Antibody Fragments Proc Natl Acad Sci U S A., vol. 90, 1993, pp. 6444-6448.
Kuehl W M, Bergsagel P L. Molecular pathogenesis of multiple myeloma and its premalignant precursor. J Clin Invest. Oct. 2012; 122(10):3456-63.
Kyle R A, Rajkumar S V. Criteria for diagnosis, staging, stratification and response assessment of multiple myieloma. Leukemia. Jan. 2009;23(1):3-9.
Kyle R A, Rajkumar S V. Multiple myeloma. N Engl J Med. Oct. 28, 2004; 351(18):1860-73.
Marino S F, et al. A complex water network contributes to high-affinity binding in an antibody-antigen interface. Data Brief. Dec. 19, 2015; 6:394-7.
Morris P W, and Venton D L. Regiospecific amine substitution into a-amanitin with retention of inhibitory properties against eukaryotic class II RNA polymerase. Int. J. Peptide Protein Res. 21 (1983) 419-430.
Oden et al. Potent anti-tumor response by targeting B cell maturation antigen (BCMA) in a mouse model of multiple myeloma. Mol Oncol. Aug. 2015; 9(7):1348-5.
Palfi, A., et al., "A promising target for amanitin based ADSs", Cancer Research, vol. 76, No. 14, Supp. 2973, Jul. 2016, Abstract.
Palfi, A., et al., 28th EORTC-NCI-AACR Symposium On Molecular Targets and Cancer Therapeutics, Nov. 29, 2016 (Nov. 29, 2016) Poster.
Palfi et al: "Preclinical evaluation of anti-CD269 antibody drug conjugates", European Journal of Cancer, vol. 69, 2016, pp. S24.
Peters C, and Brown S. Antibody-drug conjugates as novel anti-cancer chemotherapeutics. Biosci Rep. Jun. 12, 2015; 35(4).
Rajkumar S V et al. International Myeloma Working Group updated criteria for the diagnosis of multiple myeloma. Lancet Oncol. Nov. 2014; 15(12):e538-4.
Rickert R C et al. Signaling by the tumor necrosis factor receptor superfamily in B-cell biology and disease. Immunol Rev. Nov. 2011; 244(1):115-33.
Sanchez et al. Serum B-cell maturation antigen is elevated in multiple myeloma and correlates with disease status and survival. Br J Haematol. Sep. 2012; 158(6):727-38.
Shaffer A L et al. IRF4 addiction in multiple myeloma. Nature. Jul. 10, 2008; 454(7201):226-31.
Shields R L et al. High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001; 276(9):6591-604.
Trail P A. Antibody drug conjugates as cancer therapeutics. Antibodies 2013, 2(1), 113-129.
Wieland T, and Faulstich H. Amatoxins, phallotoxins, phallolysin, and antamanide: the biologically active components of poisonous Amanita mushrooms. CRC Crit Rev Biochem. Dec. 1978; 5(3):185-260.
Zanotti, et al., Syntheses of Monocyclic and Bicyclic Peptides of Tryptathionine and Glycine. International Journal Of Peptide & Protein Research, vol. 18, 1978, pp. 204-216.
Zhao L, et al. Synthesis of a Cytotoxic Amanitin for Biorthogonal Conjugation. ChemBioChem, vol. 16 (2015) 1420-1425.
Snowden et al., Guidelines for supportive care in multiple myeloma 2011. British Journal of Haematology, vo. 154, 2011 76-103.
International Search Report and Written Opinion dated Mar. 23, 2018 by the International Searching Authority for Patent Application No. PCT/EP2017/084331, which was filed Dec. 22, 2017 and published as WO 2017/220776 on Dec. 28, 2017 (Inventor—Michels et al.; Applicant—EW Nutrition GmbH) (11 pages).
International Preliminary Report on Patentability dated Dec. 25, 2018 by the International Searching Authority for Patent Application No. PCT/EP2017/065529, which was filed Jun. 23, 2017 and published as WO 2017/220776 on Dec. 28, 2017 (Inventor—Michels et al.; Applicant—EW Nutrition GmbH) (6 pages).
Palfi et al.: "Preclinical evaluation of HDP-101, anti-BCMA antibody-drug conjugate", American Association for Cancer 2017, Abstract 77.
Palfi et al.: AACR #77 "Preclinical evaluation of HDP-101, anti-BCMA antibody-drug conjugate", Heidelberg Phara GmbH/ 2017 Poster.

(56) References Cited

OTHER PUBLICATIONS

Reichard et al. "Sedolisins, a New Class of Secreted Proteases fromAspergillus fumigatuswith Endoprotease or Tripeptidyl-Peptidase Activity at Acidic pHs" Applied Andenvironmentalmicrobiology, Mar. 2006, p. 1739-1748, vol. 72, No. 3.
Oda "New families of carboxyl peptidases: serine-carboxyl peptidases and glutamic peptidases" The Journal of Biochemistry, vol. 151, Issue 1, Jan. 2012, pp. 13-25.
EP 2017832077, filed Jul. 23, 2019, Torsten Hechler (Heidelberg Pharma Research GMBH).
IN 201927024210, filed Jan. 17, 2020, Torsten Hechler (Heidelberg Pharma Research GMBH).
KR 1020197024210, filed Aug. 28, 2019, Torsten Hechler (Heidelberg Pharma Research GMBH).
RU 2019119442, filed Jun. 21, 2019 (Dec. 21, 2020), Torsten Hechler (Heidelberg Pharma Research GMBH).
JP 2019534106, filed Jun. 21, 2019, Torsten Hechler (Heidelberg Pharma Research GMBH).
MX MX/a/2019/007604, filed Jun. 21, 2019, Torsten Hechler (Heidelberg Pharma Research GMBH).
CN 201780079545.8, filed Jun. 21, 2019 (Aug. 6, 2019), Torsten Hechler (Heidelberg Pharma Research GMBH).
AU 2017380099, filed May 24, 2019 (Jun. 13, 2019), Torsten Hechler (Heidelberg Pharma Research GMBH).
CA 304458, filed May 21, 2019, Torsten Hechler (Heidelberg Pharma.
SG 11201904392S, filed May 15, 2019, Torsten Hechler (Heidelberg Pharma Research GMBH).
EP 16206849.8, filed Dec. 23, 2016, Torsten Hechler (Heidelberg Pharma Research GMBH).
PCT/EP2017/084431 (WO 2018/115466), filed Dec. 22, 2017 (Jun. 28, 2018), Torsten Hechler (Heidelberg Pharma Research GMBH).

* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | NH2 | H |

Cytotoxicity on SKBR-3 cells after incubation in Human plasma

Cytotoxicity on SKBR-3 cells after incubation in Mouse plasma

Cytotoxicity on SKBR-3 cells after incubation in PBS

FIGURE 16: (A)
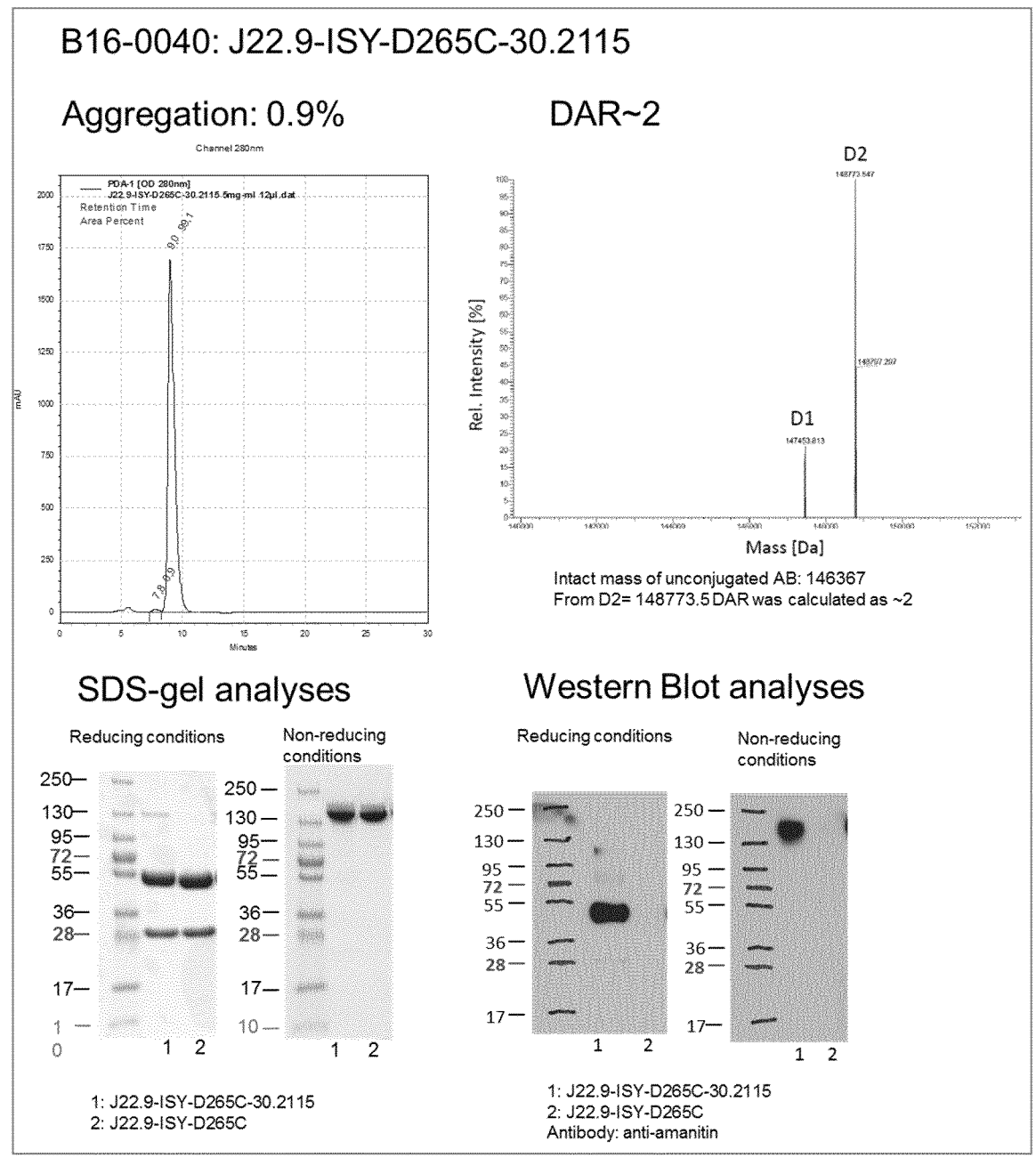

FIGURE 16: (B)
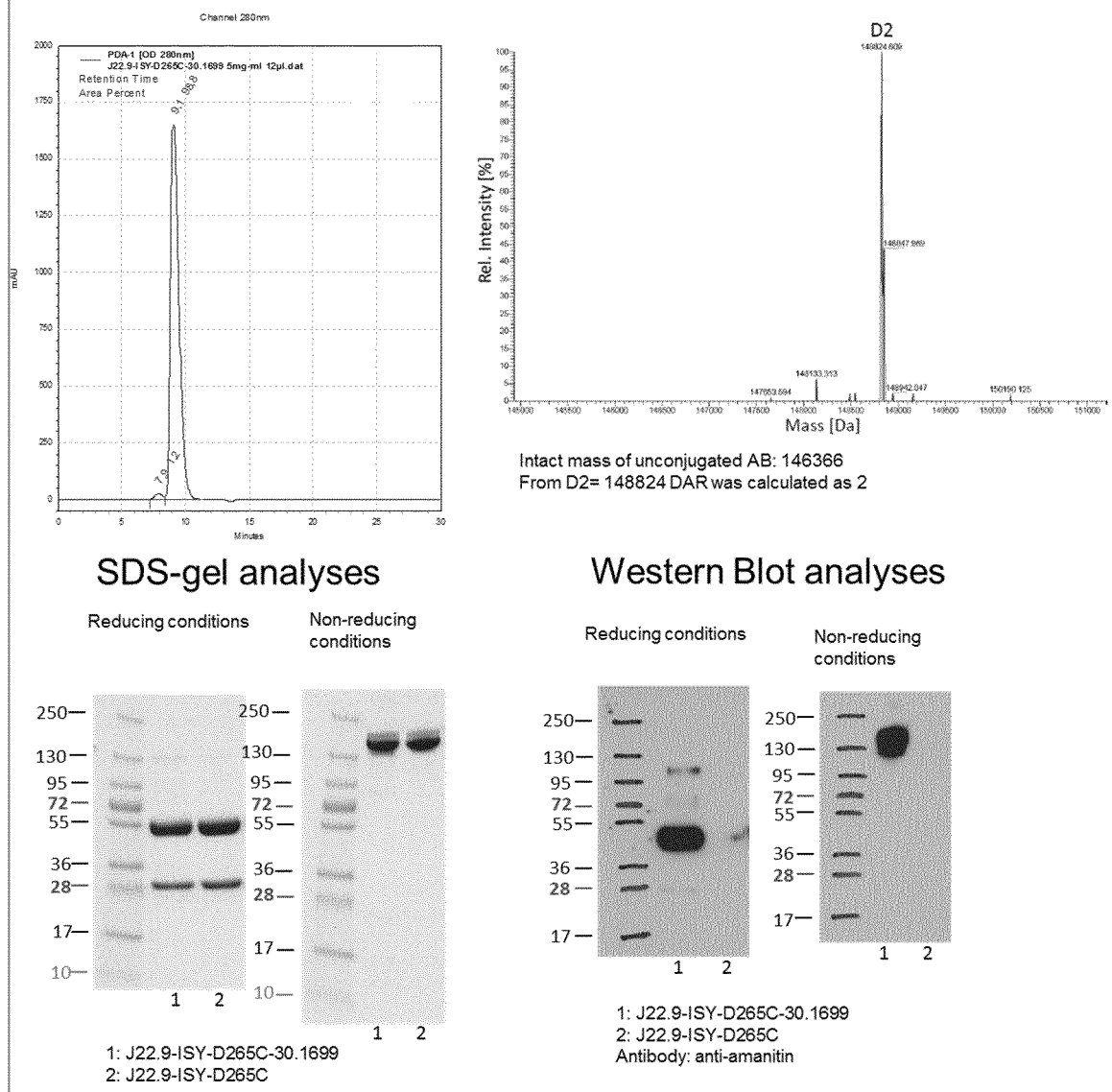

FIGURE 18
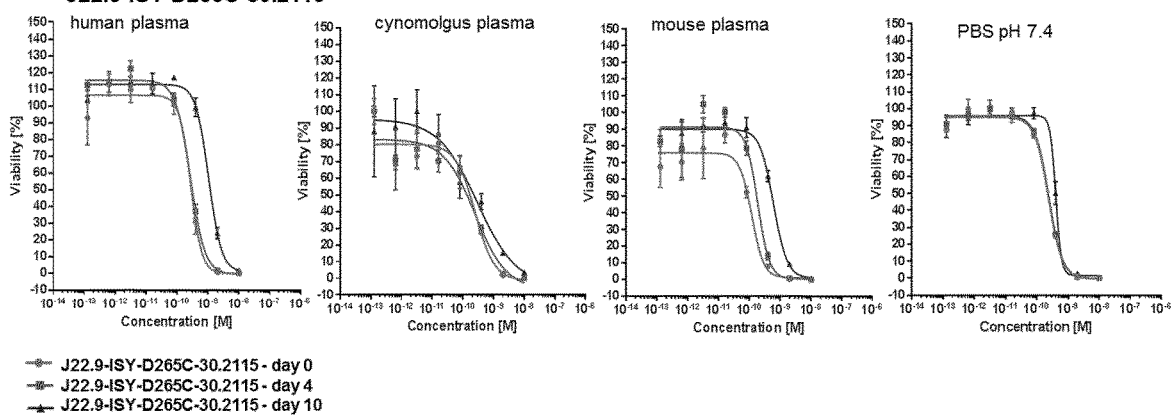
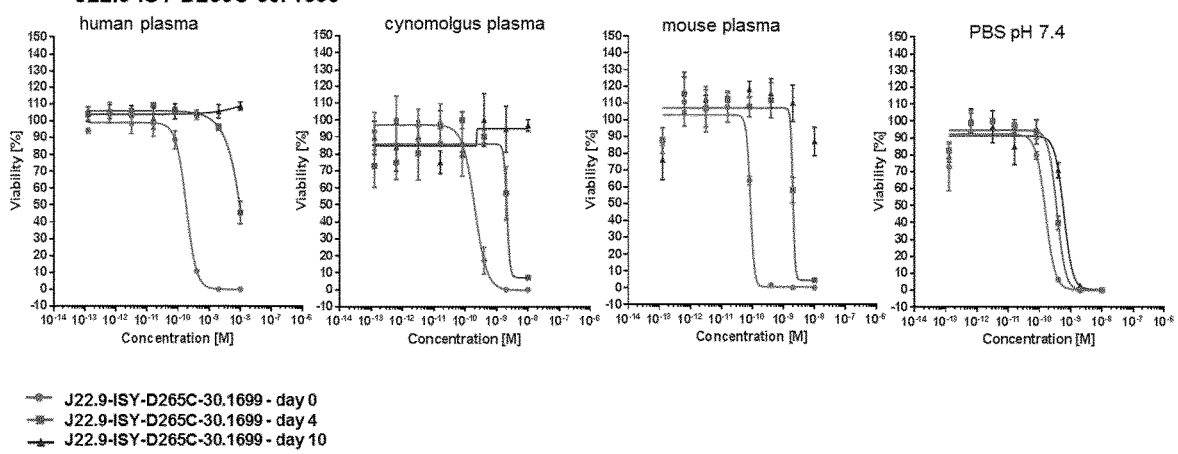

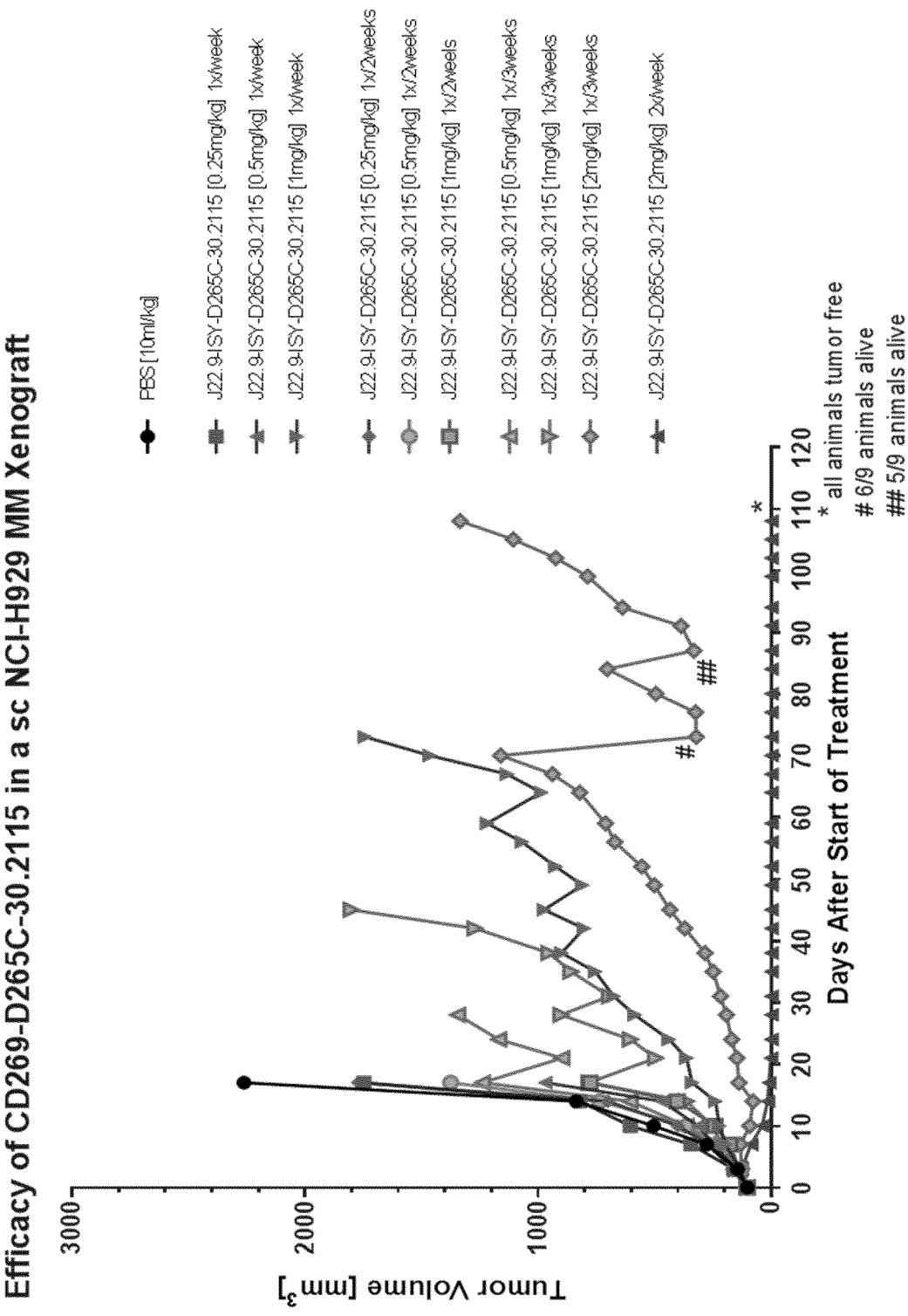

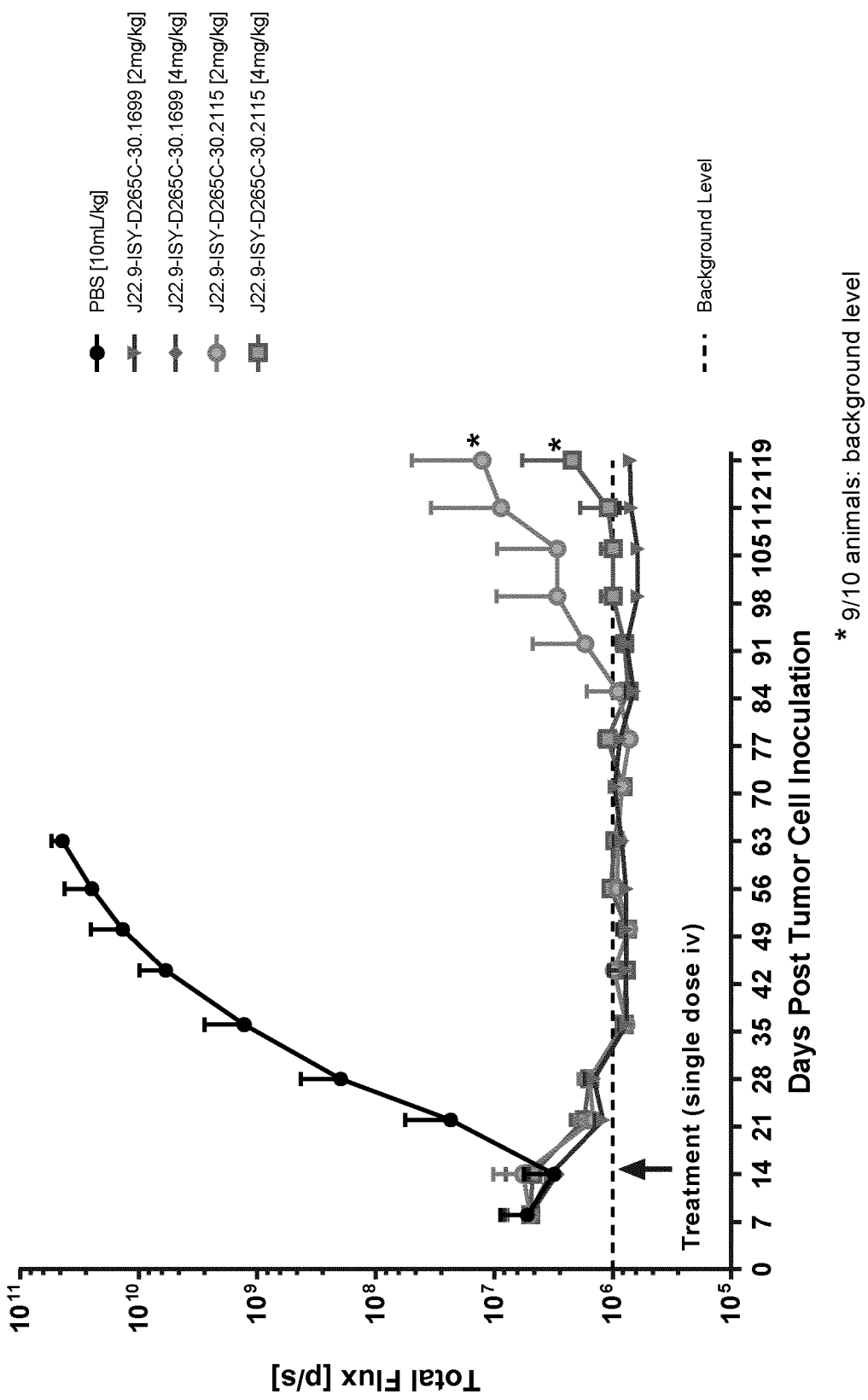

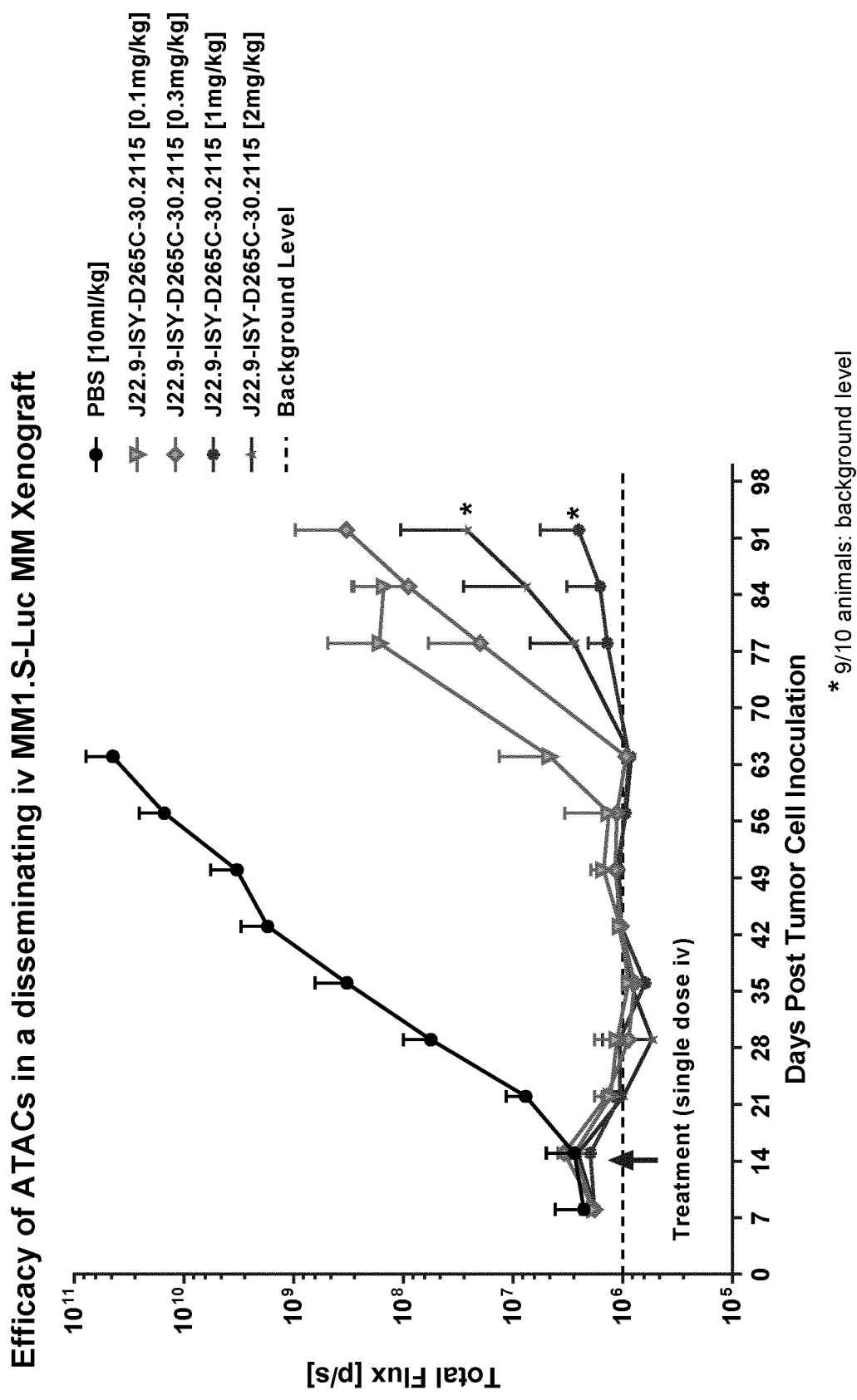

SEQUENCE LISTING

<160> NUMBER OF SEQ ID NOS: 2

<210> SEQ ID NO 1
<211> LENGTH: 450
<212> TYPE: PRT
<213> ORGANISM: Artificial Sequence
<220> FEATURE:
<223> OTHER INFORMATION: Humanized J22.9 heavy chain J22.9-ISY-D265C

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Cys Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

-continued

```
Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Humanized J22.9 light chain

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Glu Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

AMANITIN ANTIBODY CONJUGATES

CROSS REFERENCE TO RELATED APPLICATIONS

This application claims the benefit of priority under 35 U.S.C. § 371 of International Application No. PCT/EP2017/084431, filed on Dec. 22, 2017, which claims the benefit of the filing date of European Application No. 16206849.8, filed on Dec. 23, 2016. The content of these earlier filed applications is hereby incorporated by reference herein in its entirety.

SEQUENCE LISTING

The Sequence Listing submitted herewith as a text file named "13318_0040U1_Sequence_Listing," created on Jun. 11, 2019, and having a size of 8,192 bytes is hereby incorporated by reference pursuant to 37 C.F.R. § 1.52(e)(5).

FIELD OF THE INVENTION

The invention relates to a conjugate comprising (a) an amatoxin comprising (i) an amino acid 4 with a 6'-deoxy position; and (ii) an amino acid 8 with an S-deoxy position; (b) a BCMA-binding moiety comprising (i) the variable domains of humanized antibody J22.9-ISY, and (ii) a heavy chain constant region comprising a D265C mutation; and (c) a protease-cleavable linker linking said amatoxin and said target-binding moiety. The invention furthermore relates to a pharmaceutical composition comprising such conjugate, particularly for use in the treatment of multiple myeloma.

BACKGROUND OF THE INVENTION

Multiple Myeloma (MM) is the second most prevalent hematopoietic malignancy characterized by the proliferation of a single clone of plasma cells derived from B cells in the bone marrow. MM ranks as the 15$^{th}$ most common type of cancer in the US and is still considered incurable, with a median survival rate of about 30-60 months. Even though advances in the treatment of MM using conventional and novel therapeutics alone or in combination have resulted in improved response rate and thus prolonged median survival of many years, MM is still considered as incurable disease. MM represents about 0.8-1% of all cancers worldwide and approximately 10% of all hematological cancers with an estimated global incidence of more than 100.000 new cases a year and a global mortality of more than 70.000 cases yearly (National Cancer Institute SEER database).

The uncontrolled proliferation of plasma cells in MM results in the abnormal production of monoclonal immunoglobulins (also known as M-protein) that can lead to renal failure caused by immunoglobulin light chains or hyperviscosity from excessive amounts of M-proteins. In summary, clinically symptomatic MM is characterized by the presence of M-protein in serum and/or urine and end-organ damage, generally involving hypercalcemia, renal failure, anemia and bone marrow lesions (CRAB features) (Bird et al., 2011; Rajkumar et al. 2014).

Despite several treatment options, MM is an incurable disease and almost all patients will eventually develop resistant or refractory disease. Relapsed MM refers to progressive disease in which at least a partial response was previously achieved following first-line treatment of salvage therapy. Refractory MM indicates progressive disease when the patient is either unresponsive initially or following treatment within the last 60 days (Dimipoulos et al., 2015).

Without any treatment, the median length of survival after diagnosis of a myeloma patient is about three years (Kyle and Rajkumar, 2004). There are now several classes of drugs used in the treatment of myeloma: immunomodulatory drugs (thalidomide, lenalidomide, pomalidomide), proteasome inhibitors (bortezomib, carfilzomib) and stem cell transplantation. Many of the notable drugs in these classes were approved over the past 10-15 years. Treatments using these novel drugs and high-dose chemotherapy in combination with autologous or allogenic hematopoietic stem-cell transplant (SCT) have been shown to improve median survival to five years, which makes this the current standard therapy. However, many patients suffer relapse or develop treatment resistance, leaving a need to develop safe and effective treatments that prolong the duration of remission and improve survival.

About 30% of MM patients will develop renal insufficiency over the course of disease and 20% will present renal failure, caused by the accumulation and precipitation of light chains. Renal morbidity is a considerable burden for MM patients with incidence of renal replacement therapy for end-stage renal disease due to MM. Novel agents such as the proteasome inhibitor bortezomib can successfully restore renal function in a considerable proportion of patients and complications due to renal failure can be avoided when detected and treated early (Dimopoulos et al., 2008).

Even though agents like proteasome inhibitors and/or immunomodulatory drugs have improved outcome for patients, these agents do not cure the disease. Thus, the need remains for new agents with novel modes of action. The knowledge of molecules expressed on the surface of myeloma cells resulted in a number of new monoclonal antibodies currently in development for new therapies. However, most of these molecules are not exclusively expressed on MM cells and their potential to treat MM needs to be demonstrated.

Numerous drugs and therapies are currently in clinical phase: antibodies like daratumumab targeting CD38 and elotuzumab targeting SLAMF7 (Signaling Lymphocyte Activation Molecule Family Member 7), both used alone or in combination with other drugs; panabinostat, a histone deacetylase inhibitors (HDAC) to be used in combination therapy; chimeric antigen receptor engineered T (CAR-T) cells expressing an anti-BCMA single-chain variable fragment allowing specific targeting of MM cells.

MM is characterized by the malignant proliferation of plasma cells, terminally differentiated B-cells which under normal circumstances are responsible for the mass production of immunoglobulins. This progression from plasma cells to malignant myeloma cell is associated with multiple genetic and oncogenic events including deregulation of cyclin D1 and c-Myc, and mutations like KRAS, BRAF, FGFR3 (fibroblast growth factor receptor 3) and TP53 (Shaffer et al., 2008; Kuehl and Bergsagel, 2012; Chesi and Bergsagel, 2015).

Despite these genetic alterations, the malignant plasma cell remains largely dependent on the bone marrow (BM) environment. Following binding of the MM cells in the BM, signalling cascades are activated including accessory growth factors and its ligands secreted by the BM accessory cells. Components released by these accessory cells play a critical role in MM to both promote disease and escape from immune surveillance.

Antibody-drug conjugates (ADCs) aim to take advantage of the specificity of monoclonal antibodies to deliver potent cytotoxic drugs selectively to antigen-presenting tumor cells.

The antibody should target a well-characterized antigen with high and specific expression at the tumor site and low or no expression on normal tissue, thus maximizing the efficacy of the ADC while limiting toxicity.

Members of the tumor necrosis factor receptor (TNFR) superfamily and their ligands play a critical role in controlling proliferation, differentiation and apoptosis of B-cells. In particular, B-cell activating factor (BAFF) ligand-receptor network play a central role in regulating B-cell maturation and differentiation into malignant plasma cells. The functionally related BAFF receptors BAFF-R, cyclophilin ligand interactor (TACI) and B-Cell maturation antigen (BCMA) are type III transmembrane proteins lacking a signal-peptide and containing cysteine-rich extracellular domains.

These receptors promote survival of B-cells at distinct stages of development and thus their expression patterns on B-cells differ depending on the type of B-cells and their stage of maturation and activation. BAFF-R expression is not detectable on B-cell precursors but is the dominant receptor expressed on mature B-cells. BAFF-R mediates the survival of B-cells, sustains the longevity of the germinal-center reaction and promotes immunoglobulin class-switch recombination. TACI is expressed on B-cells and activated T-cells and is important in class-switch recombination and supports T-cell dependent antibody response. BCMA, which is almost exclusively expressed on plasma cells but is absent from naïve and memory B-cells, promotes B-cell differentiation into plasma cells and thus promotes the maintenance of humoral immune response. Soluble BCMA is elevated in the serum of MM patients and the successful donor lymphocyte infusion is associated with the formation of antibodies against BCMA. The level of serum BCMA found among MM patients associates with clinical status and overall survival. (Belucci et al., 2005; Sanchez et al., 2012).

BAFF, APRIL (a proliferation-inducing ligand) and BCMA perform critical roles in decision-making process from B-cell to plasma and MM cell. As B-cells egress from the bone marrow, further maturation into marginal zone B-cells (MZ B) is dependent on BAFF. BAFF is also essential for the homeostasis of naïve recirculating B-cells and MZ B-cells. Downregulation of BAFF-R on plasma cells is coincident with the upregulation of BCMA, which can bind BAFF as well as APRIL. Transcription factor NFκB plays a crucial role in pathways regulation, B-cell proliferation, survival and differentiation. NFκB activity is modulated by the inhibitor of κB (IκB) proteins. Among these, IκBα retains NFκB dimers inactive in the cytoplasm and, when degraded, releases bound NFκB dimers to translocate to the nucleus and drive gene expression. Regulation of IκB activity through degradation depends on serine phosphorylation by the IκB kinase (IKK) (Rickert et al., 2011).

Various anti-BCMA antibodies have been generated in the past, including murine antibody J22.9 (WO 2014/068079) and humanized versions thereof (WO 2015/166073).

In order to obtain antibody-drug conjugates, bifunctional linkers with attachment sites for both the antibody and the drug are used to join the two components.

With respect to conjugation to the antibody, linker attachment strategies typically rely on cysteine or lysine residues on the antibody. Ideally, the linker must remain stable in systemic circulation to minimize adverse or toxic effects. Upon antigen recognition and binding, the resulting ADC receptor complex is internalized through receptor-mediated endocytosis. The unconjugated toxin should demonstrate high potency to enable efficient killing upon release from ADC. Release of the toxic payload should only occur inside the target cell and ADC must be stable in plasma. For the release of the toxin from the antibody inside the cell linkers can be either cleavable (either cleaved by lysosomal proteases, hydrolysed at low pH in the lysosomal compartment or released from disulfide bonds by intracellular gluthatione) or non-cleavable (depending on complete degradation of the antibody after internalization of the ADC).

Finally, with respect to the toxic payload of antibody-drug conjugates, two main classes of cytotoxic agents are currently used in clinical evaluations: drugs that disrupt microtubule assembly or compounds that bind to the minor groove of DNA causing double strand breaks.

Amatoxins are cyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumor therapy had already been explored in 1981 by coupling an anti-Thy 1.2 antibody to a-amanitin using a linker attached to the indole ring of Trp (amino acid 4; see FIG. 1) via diazotation (Davis & Preston, Science 213 (1981) 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 21 (1983) 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji) and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

It is known that amatoxins are relatively non-toxic when coupled to large biomolecule carriers, such as antibody molecules, and that they exert their cytotoxic activity only after the biomolecule carrier is cleaved off. In light of the toxicity of amatoxins, particularly for liver cells, it is of outmost importance that amatoxin conjugates for targeted tumor therapy remain highly stable after administration in plasma, and that the release of the amatoxin occurs after internalization in the target cells. In this context, minor improvements of the conjugate stability may have drastic consequences for the therapeutic window and the safety of the amatoxin conjugates for therapeutic approaches.

Patent application WO 2016/142049 describes antibody-amanitin conjugates wherein the amanitin payload is attached to the antibody via specifically engineered cysteine residues in the antibody heavy chain constant region. Depending on the nature of the mutated residue, the replacement of the wild-type amino acid residue may influence the activity.

It has already been reported that amatoxin-based antibody conjugates directed at CD269 may offer advantages in the treatment of tumor patients (see Palfi et al.: "Preclinical evaluation of anti-CD269 antibody drug conjugates", European Journal of Cancer 69 (2016), S21 & 28$^{th}$ EORTC-NCI-AACR Symposium on Molecular Targets and Cancer Therapeutics, Munich (Germany) Nov. 29-Dec. 2, 2016; Palfi et al.: "CD269—A promising target for amanitin based ADCs", Cancer Research 76 (No. 14 suppl) (2016) 2973 & 107$^{th}$ Annual Meeting of the American Association for Cancer Research, New Orleans (U.S.A.) Apr. 16-Apr. 20, 2016). However, no details were provided about the specific nature of the amatoxin derivative being used and of the specific linkage between that amatoxin derivative and the anti-CD269 antibody.

Thus, significant progress has already been made in the development of amatoxin-based conjugates for therapeutic uses. However, the present inventors have found that constructs based on α- and β-amatoxin were not fully stable under stress conditions in plasma and resulted in a substantial degree of cross-linked products (see FIG. 2). This effect was completely unexpected, and the reasons for such instability and cross-linking were unclear. In FIG. 2 it is additionally shown that the amount of cross-linked products formed from an amatoxin-based antibody conjugate can be reduced by the addition of cysteine, and in FIGS. 3 and 4 it is shown that α-amanitin reacts with cysteine. However, the stability of the conjugates comprising a highly toxic amatoxin is of utmost importance for the envisaged use as a therapeutic molecule for administration to human beings.

OBJECT OF THE INVENTION

Thus, there was still a great need for amatoxin-based antibody-drug conjugates having a high efficacy in target cells, with simultaneously having high stability. The solution to this problem, i.e. the identification of (a) an appropriate parental anti-BCMA antibody, (b) an appropriate strategy for attaching the toxic payload via linker to the antibody, (c) an appropriate linker and (d) an appropriate amatoxin variant was neither provided nor suggested by the prior art.

SUMMARY OF THE INVENTION

The present invention is based on the unexpected observation that a variant form of an amatoxin conjugated to an anti-BCMA antibody based on antibody J22.9, wherein the antibody and the amatoxin are linked by a cleavable linker shows an increased stability under stress conditions, particularly in human plasma, and an improved therapeutic index.

Thus, in one aspect the present invention relates to a conjugate according to Formula I comprising (a) an amatoxin comprising (i) an amino acid 4 with a 6'-deoxy position; and (ii) an amino acid 8 with an S-deoxy position; (b) a BCMA-binding moiety comprising (i) the variable domains of the heavy chain according to SEQ ID NO: 1 and the light chain according to SEQ ID NO: 2 of antibody J22.9-ISY, and (ii) a heavy chain constant region comprising a D265C mutation; and (c) a protease-cleavable linker, wherein said BCMA-binding moiety is attached to said linker via the thiol group of the engineered cysteine residue at position 265 in the antibody heavy chain.

Formula I

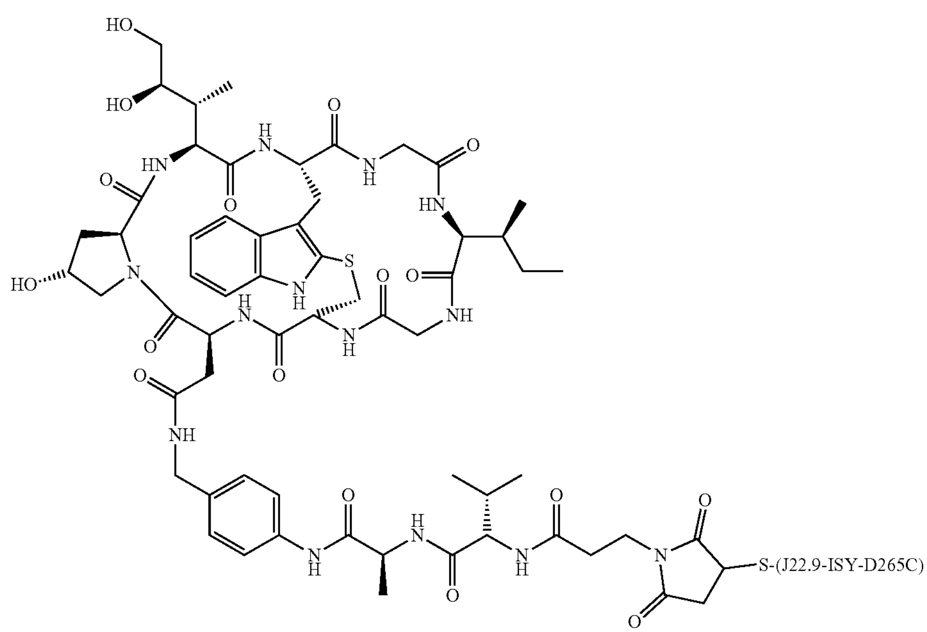

In a second aspect, the present invention relates to a pharmaceutical composition comprising the conjugate of the present invention.

In a third aspect, the present invention relates to the conjugate of the present invention, or the pharmaceutical composition of the present invention, for use in the treatment of cancer in a patient, particularly wherein the cancer is selected from the group consisting of multiple myeloma, diffuse large B-cell lymphoma (DLBCL), and chronic lymphocytic leukemia (CLL), particularly multiple myeloma.

BRIEF DESCRIPTION OF THE DRAWINGS

FIG. 16 shows the QA results of the production of (A) J22.9-ISY-D265C-30.2115, and (B) J22.9-ISY-D265C-30.1699.

FIG. 18 shows the results from experiments analysing plasma stability and cytotoxic potential. J22.9-ISY-D265C-30.2115 (A) and J22.9-ISY-D265C-30.1699 (B) were incubated in PBS for control, or human, cynomolgus or mouse plasma for 0, 4, and 10 days at 37° C. and analysed for remaining cellular toxicity potential using BCMA-positive NCI-H929 cells.

FIG. 22 shows the antitumor activity in mouse NCI-H929 subcutaneous xenograft in repeated dose application: Female CB-17 Scid mice were subcutaneously inoculated with 5×10⁶ NCI-H929 cells. Once tumor volume reached 80 mm³, mice (9 animals per group) were treated intravenously either once per week (1×/week), every two weeks (1×/2 weeks) or every 3 weeks (1×/3 weeks) with J22.9-ISY-D265C-30.2115 (doses 0.25 mg/kg, 0.5 mg/kg or 1 mg/kg) or were treated with PBS as control. In addition, 2 mg/kg doses were applied twice per week (2×/week). Tumor volumes were monitored twice per week.

DETAILED DESCRIPTION OF THE INVENTION

Figure 1:
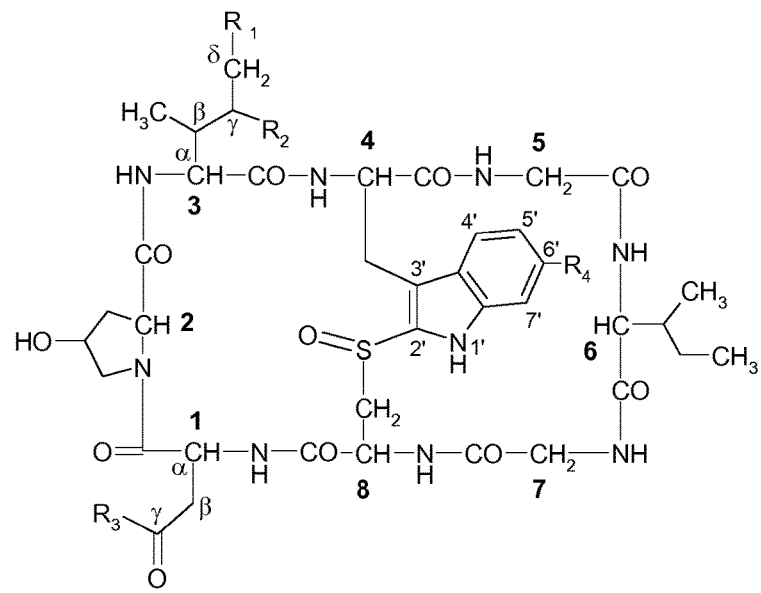
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Particularly, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law.

The present invention will now be further described. In the following passages different aspects of the invention are defined in more detail. Each aspect so defined may be combined with any other aspect or aspects unless clearly indicated to the contrary. In particular, any feature indicated as being of particular relevance or advantageous may be combined with any other feature or features indicated as being of particular relevance or advantageous.

The present invention is based on a combination of different advantageous elements and features and in particular on the unexpected observation that a variant form of an amatoxin conjugated to an anti-BCMA antibody based on antibody J22.9, wherein the antibody and the amatoxin are linked by a cleavable linker shows an increased stability under stress conditions, particularly in human plasma, and an improved therapeutic index.

Thus, in one aspect the present invention relates to a conjugate comprising (a) an amatoxin comprising (i) an amino acid 4 with a 6'-deoxy position; and (ii) an amino acid 8 with an S-deoxy position; (b) a BCMA-binding moiety comprising the variable domains of the heavy chain according to SEQ ID NO: 1 and the light chain according to SEQ ID NO: 2 of antibody J22.9-ISY, and (c) a protease-cleavable linker, wherein said BCMA-binding moiety is attached to said linker via the thiol group of the cysteine residue at position 265 in the antibody heavy chain.

In a particular embodiment, the BCMA-binding moiety comprises a heavy chain constant region comprising a D265C mutation.

In a particular embodiment, said protease-cleavable linker is a self-immolative linker.

In a particular embodiment, the conjugate is the conjugate according to Formula I.

Formula I

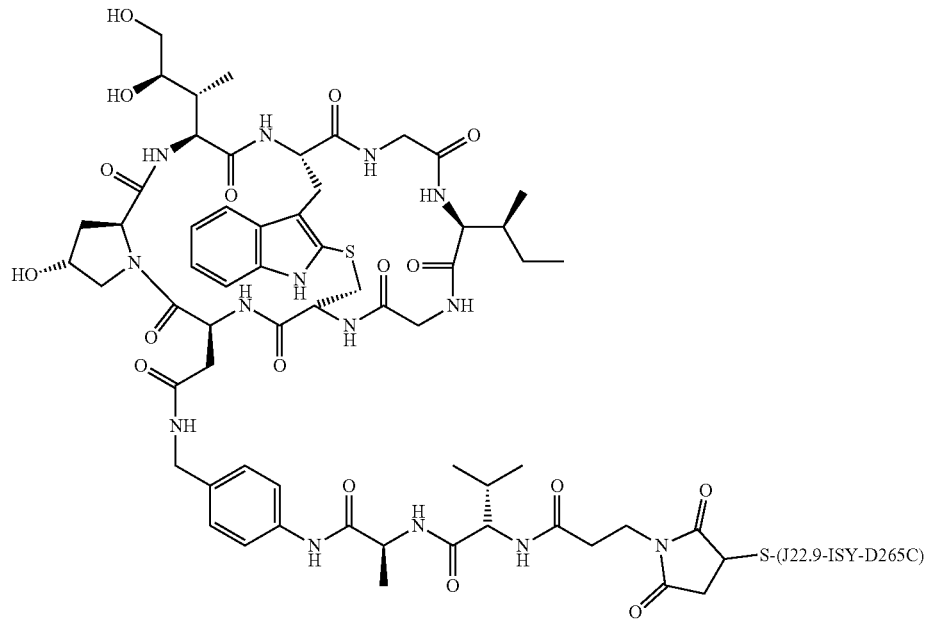

In the context of the present invention, the term "amatoxin" includes all cyclic peptides composed of 8 amino acids as isolated from the genus Amanita and described in Wieland, T. and Faulstich H. (1978), which comprise the specific positions according to (i) (i.e. where the indole moiety of the amino acid residue tryptophan has no oxygen-containing substituent at position 6', particularly where position 6' carries a hydrogen atom) and (ii) (i.e. in which the thioether sulfoxide moiety of naturally occurring amatoxins is replaced by a sulfide), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue carries at least the positions (i) and (ii) mentioned above and is functionally active by inhibiting mammalian RNA polymerase II.

Functionally, amatoxins are defined as peptides or depsipeptides that inhibit mammalian RNA polymerase II. Preferred amatoxins are those with a functional group (e.g. a carboxylic group or carboxylic acid derivative such as a carboxamide or hydroxamic acid, an amino group, a hydroxy group, a thiol or a thiol-capturing group) that can be reacted with linker molecules or target-binding moieties as defined above. Amatoxins which are particularly suitable for the conjugates of the present invention are di-deoxy variants of α-amanitin, β-amanitin, γ-amanitin, ε-amanitin, amanullin, or amanullinic acid, or mono-deoxy variants of amanin, amaninamide, y-amanin, or y-amaninamide as shown in FIG. 1 as well as salts, chemical derivatives, semisynthetic analogues, and synthetic analogues thereof.

Figure 2:
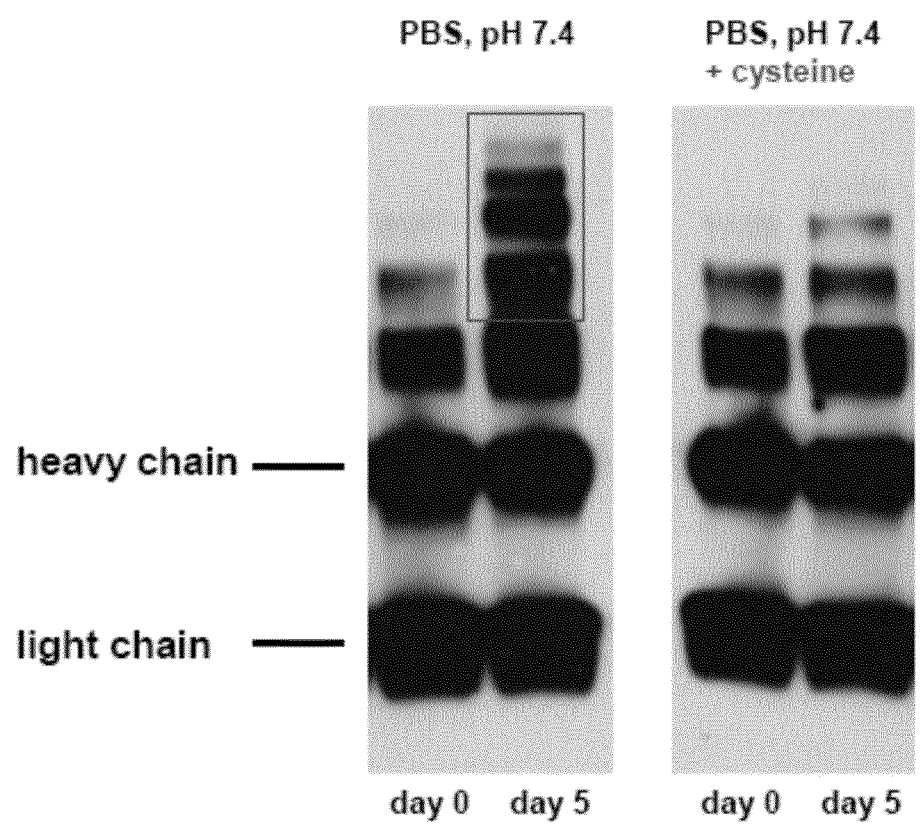
FIG. 2 shows the results of a stress testing experiment in an anti-amanitin Western blot. A trastuzumab-amanitin conjugate (Her-30.0643; lysine conjugation via 6'-OH; stable linker) was incubated for 5 days at 37° C. in PBS, pH 7.4, which led to extensive inter- and intrachain cross-linking; cross-linking of antibody chains could be reduced by addition of free cysteine.
Figure 3:
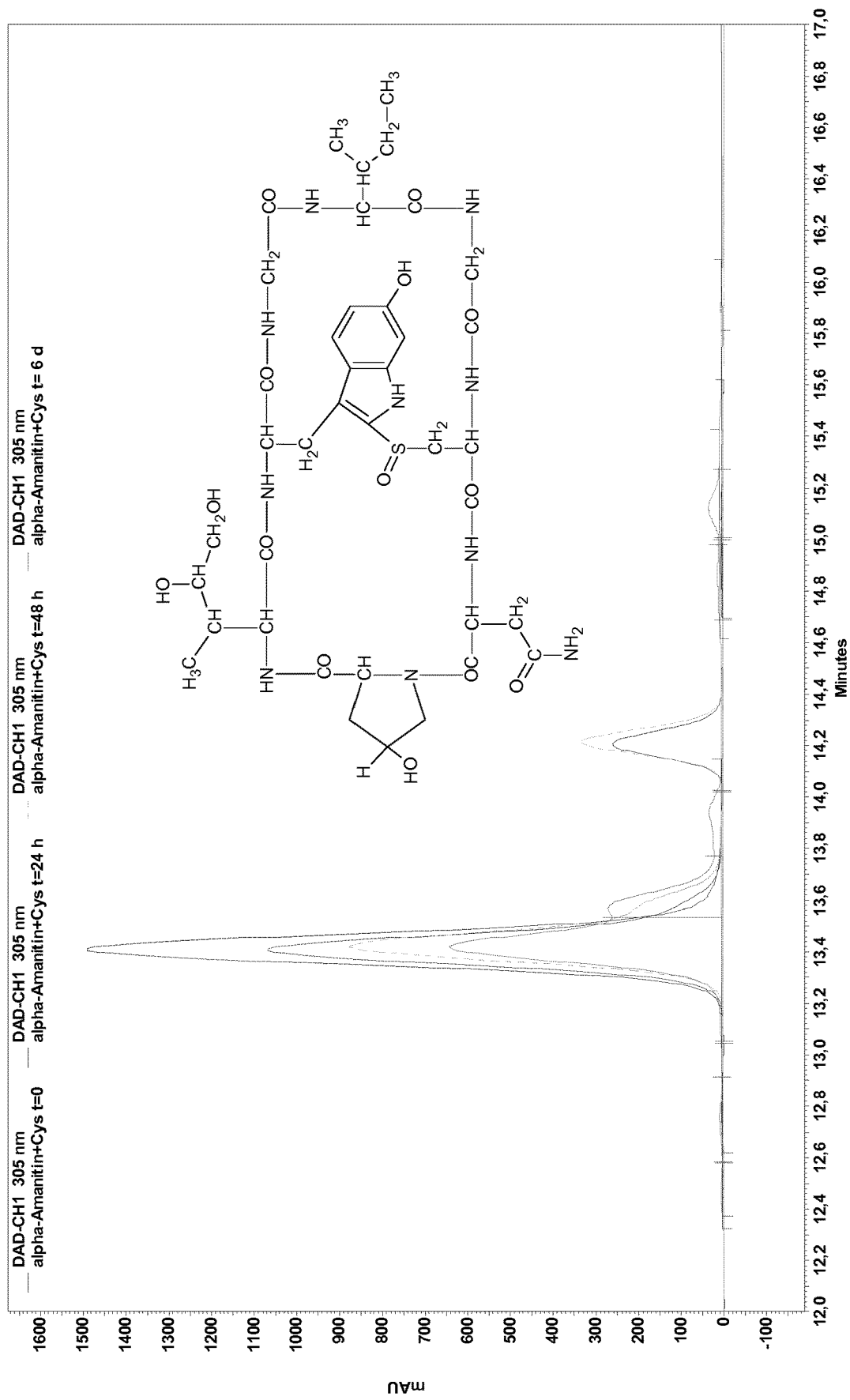
FIG. 3 shows that α-amanitin shows a strong reactivity with cysteine in PBS buffer, pH 7.4. 1 mg/mL α-amanitin 10 mg/mL cysteine in PBS, pH 7.4 at 37° C. after 24 h, 48 h and 6 d RP-HPLC C18.
Figure 4:
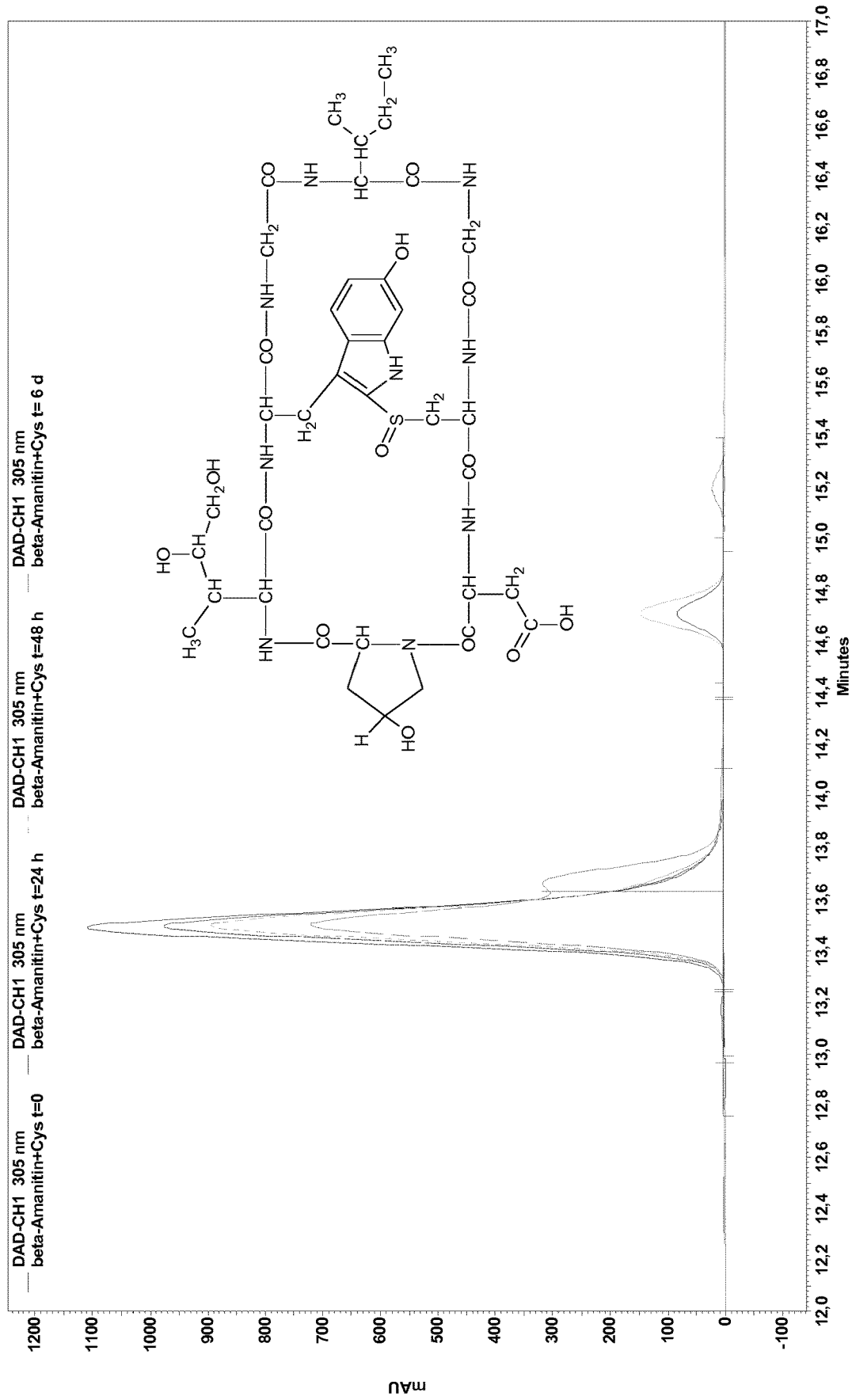
FIG. 4 shows that β-amanitin shows a strong reactivity with cysteine in PBS buffer, pH 7.4. 1 mg/mL β-amanitin 10 mg/mL cysteine in PBS, pH 7.4 at 37° C. after 24 h, 48 h and 6 d RP-HPLC C18.
Figure 5:
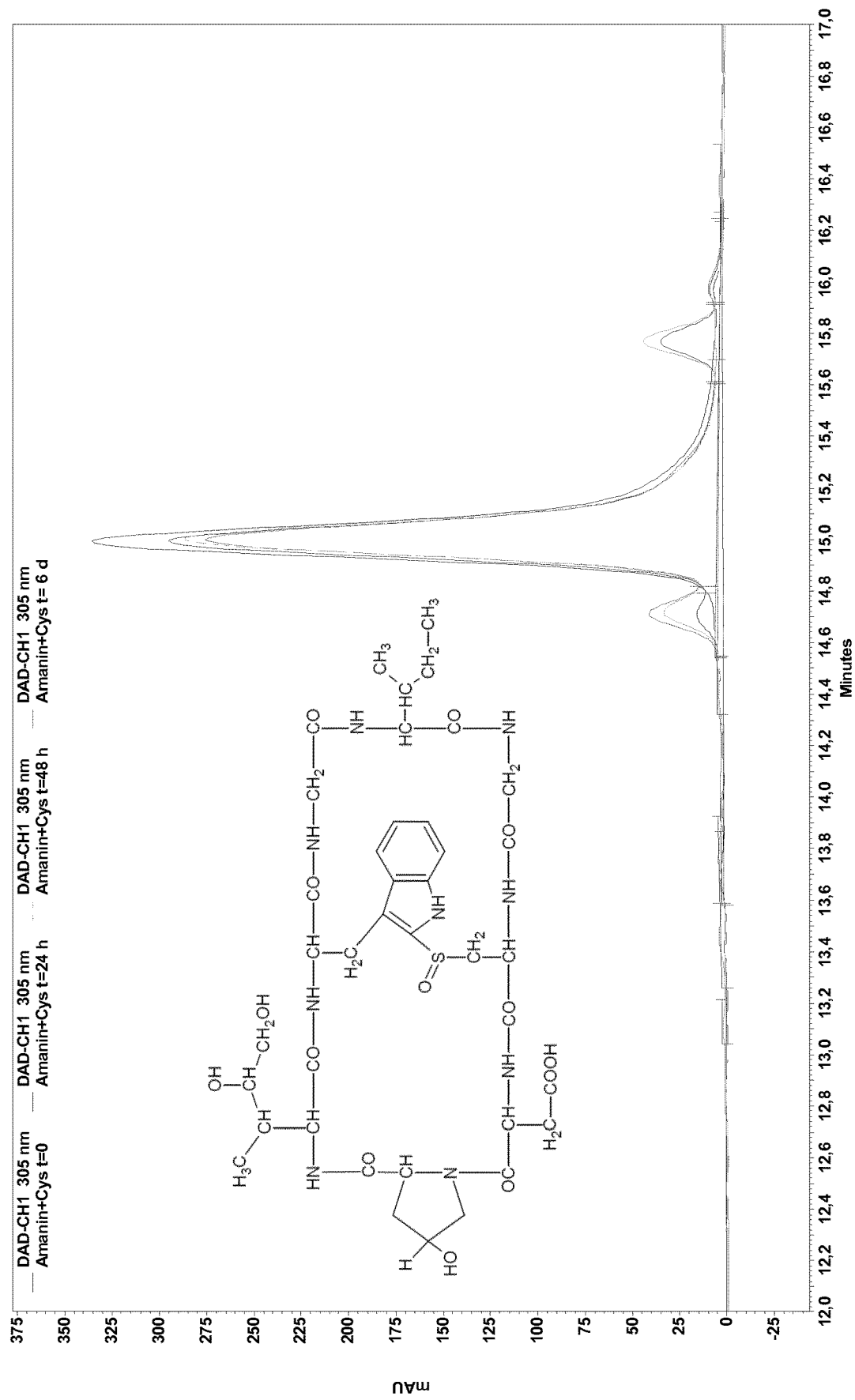
FIG. 5 shows that a 6'-deoxy variant at amino acid 4 ("amanin") shows a reduced reactivity with cysteine. 1 mg/mL amanin 10 mg/mL cysteine in PBS, pH 7.4 at 37° C. after 24 h, 48 h and 6 d RP-HPLC C18.
Figure 6:
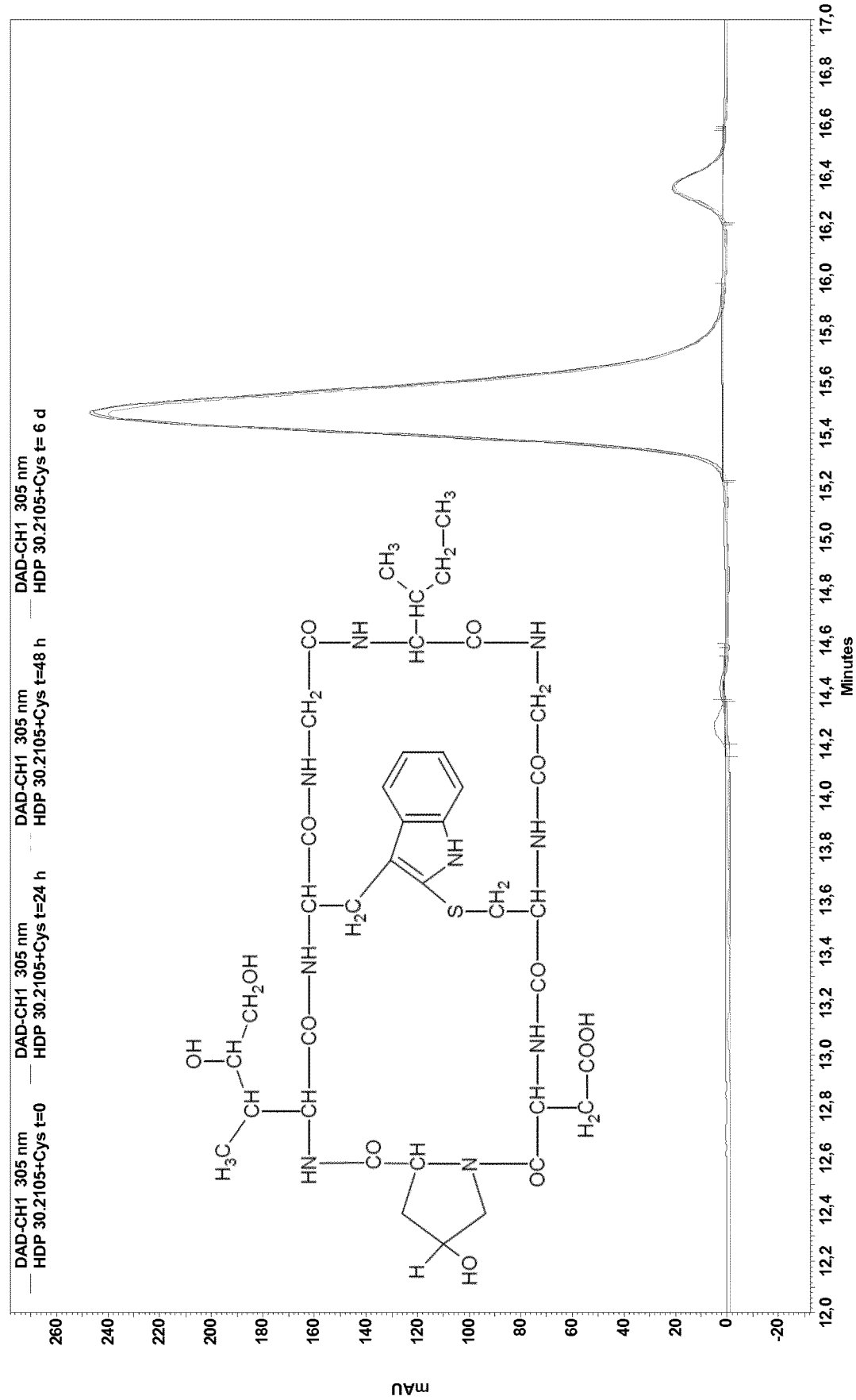
FIG. 6 shows that a double deoxy variant HDP 30.2105 (6'-deoxy at amino acid 4 and S-deoxy at amino acid 8; formula I with $R^3$=—$OR^5$ and each $R^5$=H) shows complete absence of reactivity with cysteine. 1 mg/mL HDP 30.2105, 10 mg/mL cysteine in PBS, pH 7.4 at 37° C. after 24 h, 48 h and 6 d RP-HPLC C18; *impurity.
Figure 7:
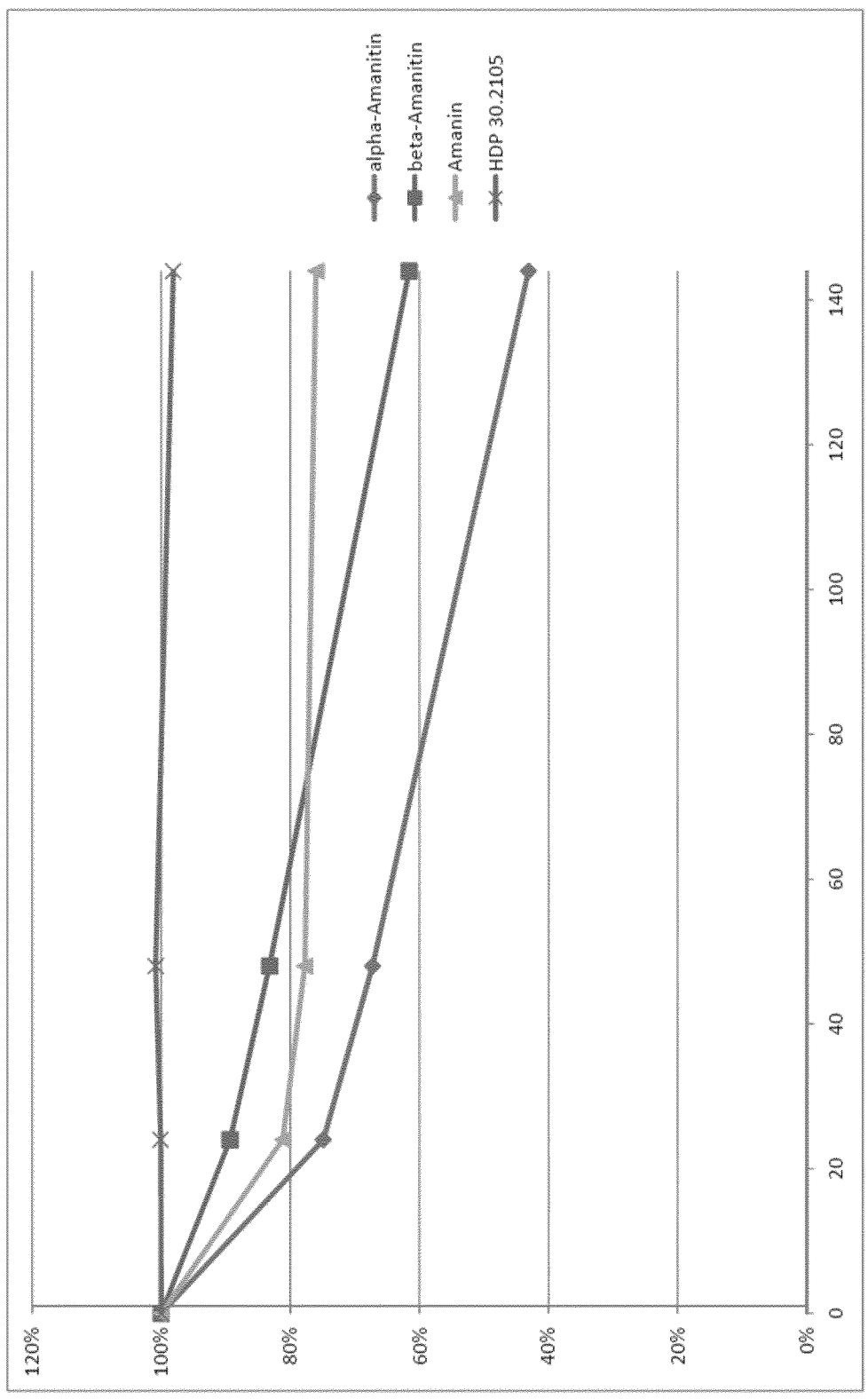
FIG. 7 summarizes the results from FIGS. 3 to 6; x axis: reaction time in hours; y axis: amount of remaining amatoxin variant in %.
Figure 8:
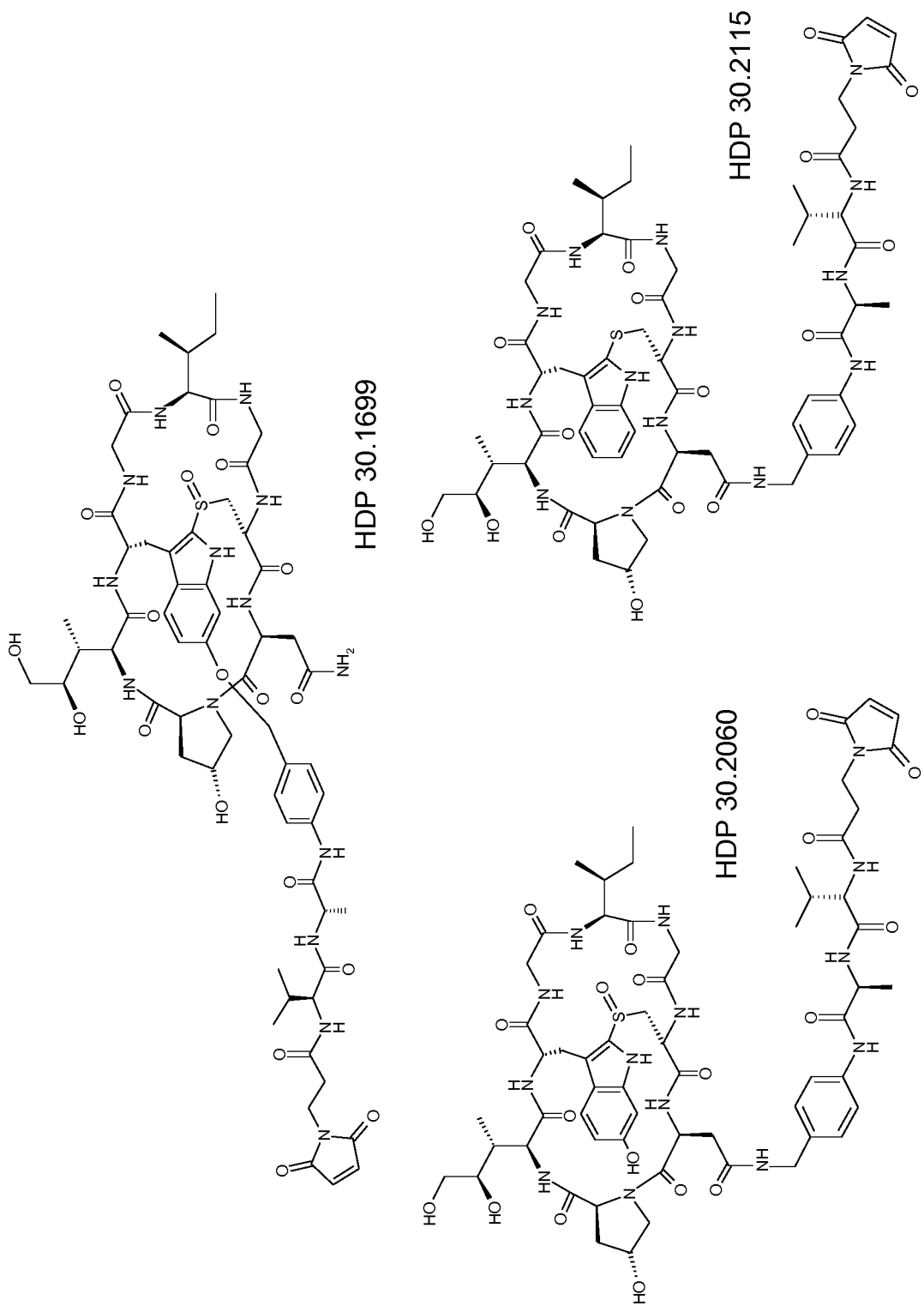
FIG. 8 shows alpha-amanitin derivative HDP 30.1699 with cleavable linker at AA4-6-OH moiety, alpha-amanitin derivative HDP 30.2060 with cleavable linker at AA1 γ-position and double deoxy amatoxin variant HDP 30.2115 with cleavable linker at AA1 γ-position.
Figure 9:
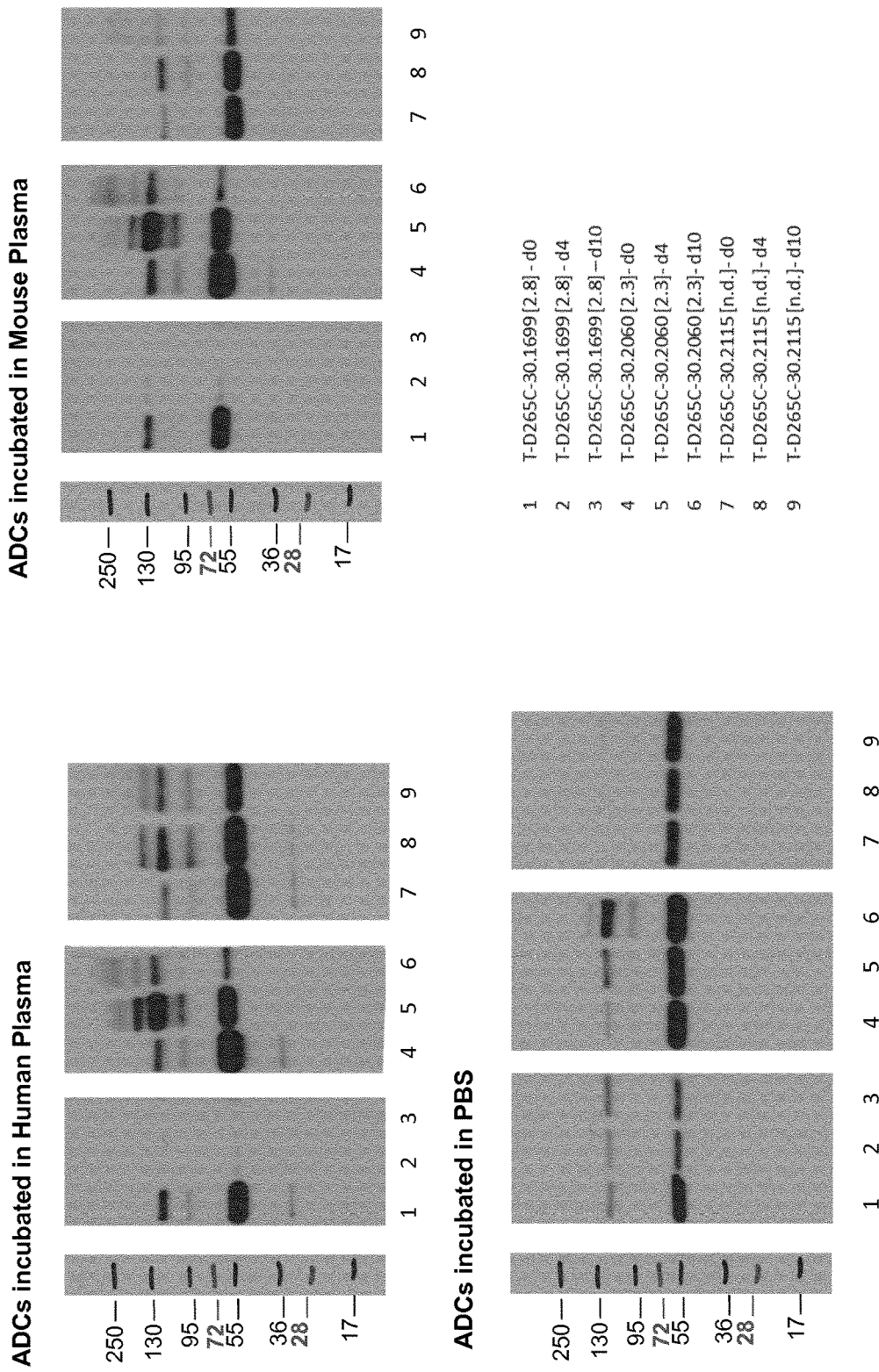
FIG. 9 shows Western-Blot analysis of amatoxin derivatives HDP 30.1699, HDP 30.2060 and HDP 30.2115 conjugated to reference Thiomab antibody with D265C mutation after incubation at 37° C. in human plasma, mouse plasma and phosphate buffered saline (PBS) for 0, 4 and 10 days. Detection was done with a polyclonal anti-amanitin antibody from rabbit and an anti-rabbit antibody conjugated to horseradish peroxidase. HDP 30.1699 and HDP 30.2060 showed considerable cross-links and loss of the amatoxin moiety. Double deoxy amanitin variant HDP 30.2115 shows high stability and significantly reduced cross-links.
Figure 10:
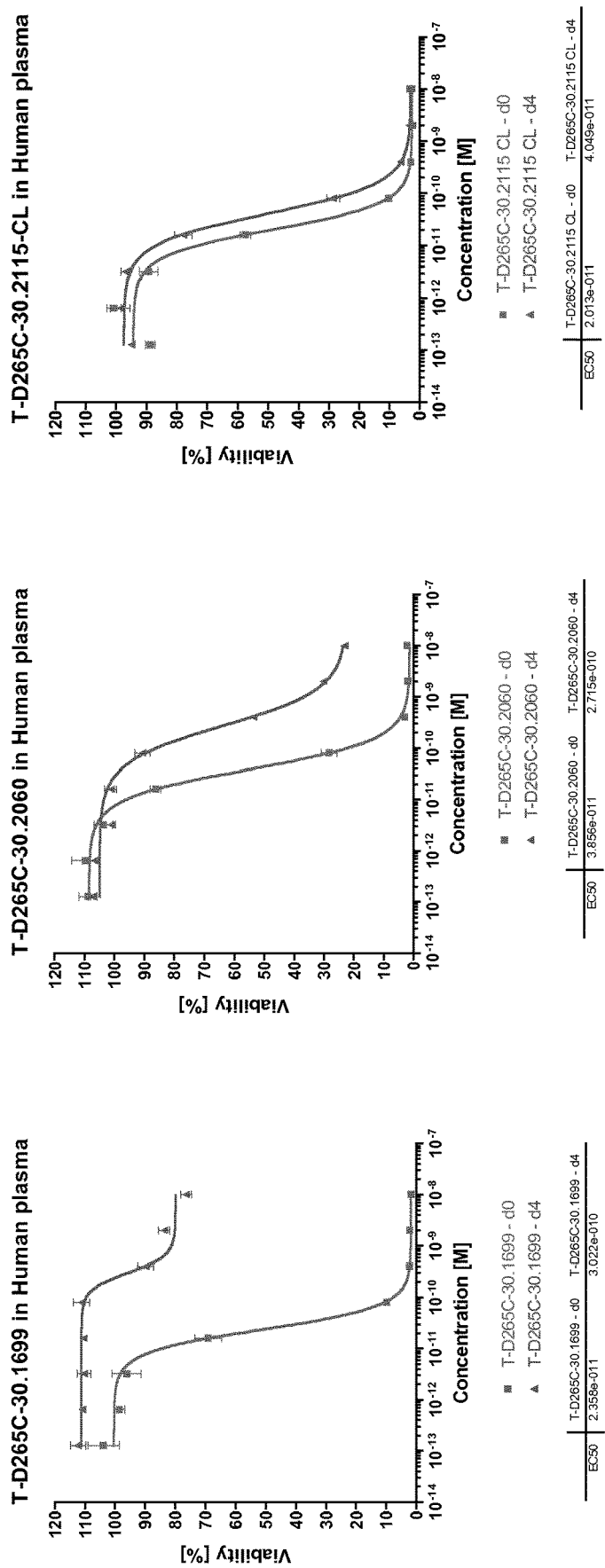
FIG. 10 shows cytotoxicity of amatoxin derivatives HDP 30.1699, HDP 30.2060 and HDP 30.2115 conjugated to reference Thiomab antibody with D265C mutation. Test items were incubated in human plasma at 37° C. for 0 an 4 days. Cytotoxicity assay were performed on SKBR-3 cells for 96 h. HDP 30.1699 and HDP 30.2060 based ADCs show remarkable loss of cytotoxicity after 4 days plasma stressing whereas deoxygenated derivative HDP 30.2115 shows still picomolar activity
Figure 11:
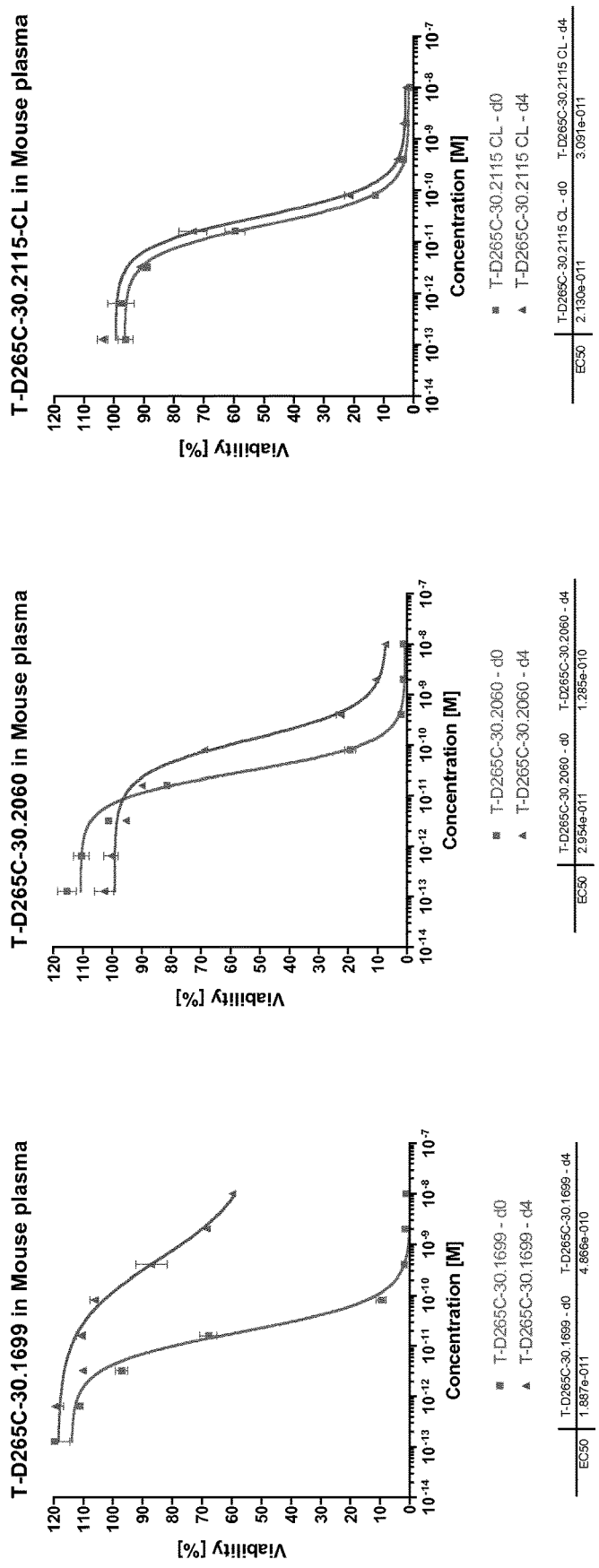
FIG. 11 shows cytotoxicity of amatoxin derivatives HDP 30.1699, HDP 30.2060 and HDP 30.2115 conjugated to reference Thiomab antibody with D265C mutation. Test items were incubated in mouse plasma at 37° C. for 0 an 4 days. Cytotoxicity assay were performed on SKBR-3 cells for 96 h. HDP 30.1699 and HDP 30.2060 based ADCs show remarkable loss of cytotoxicity after plasma stressing whereas deoxygenated derivative HDP 30.2115 remains almost unchanged.
Figure 12:
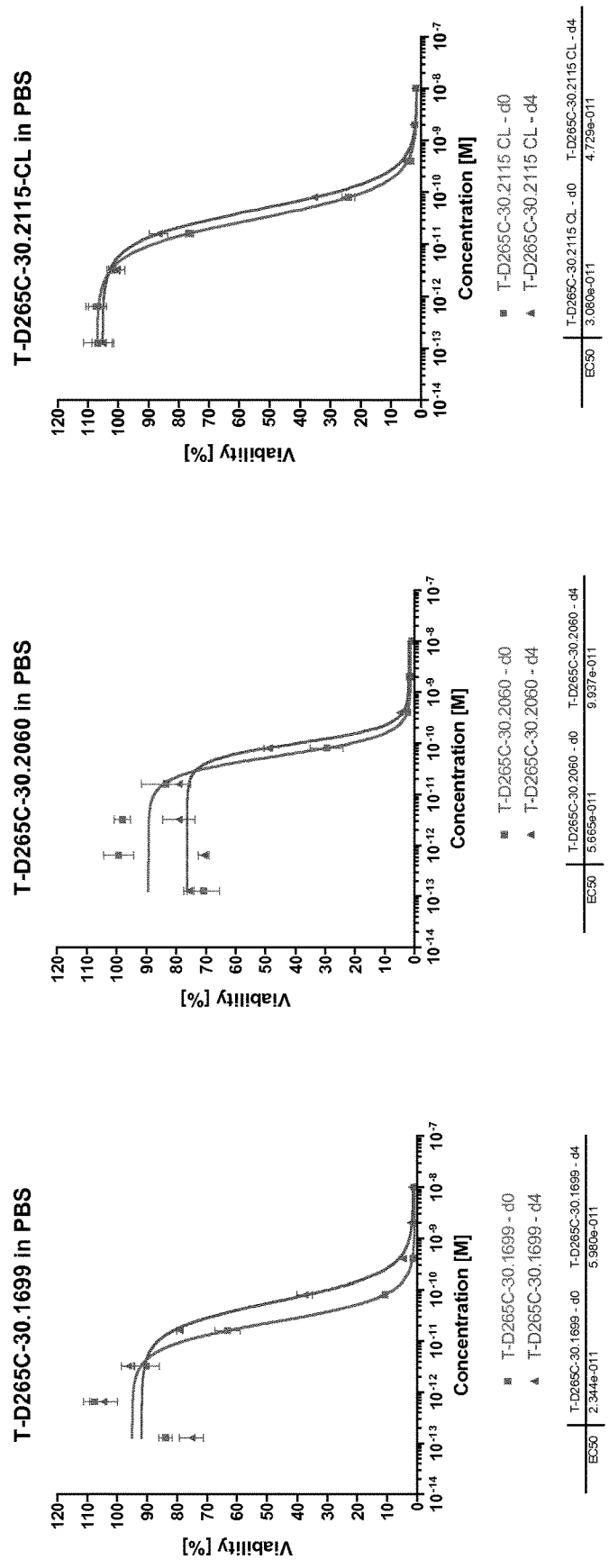
FIG. 12 shows cytotoxicity of amatoxin derivatives HDP 30.1699, HDP 30.2060 and HDP 30.2115 conjugated to reference Thiomab antibody with D265C mutation. Test items were incubated in PBS at 37° C. for 0 an 4 days. Cytotoxicity assay were performed on SKBR-3 cells for 96 h. All ADCs show adequate stability to non-enzymatic environment.
Figure 13:
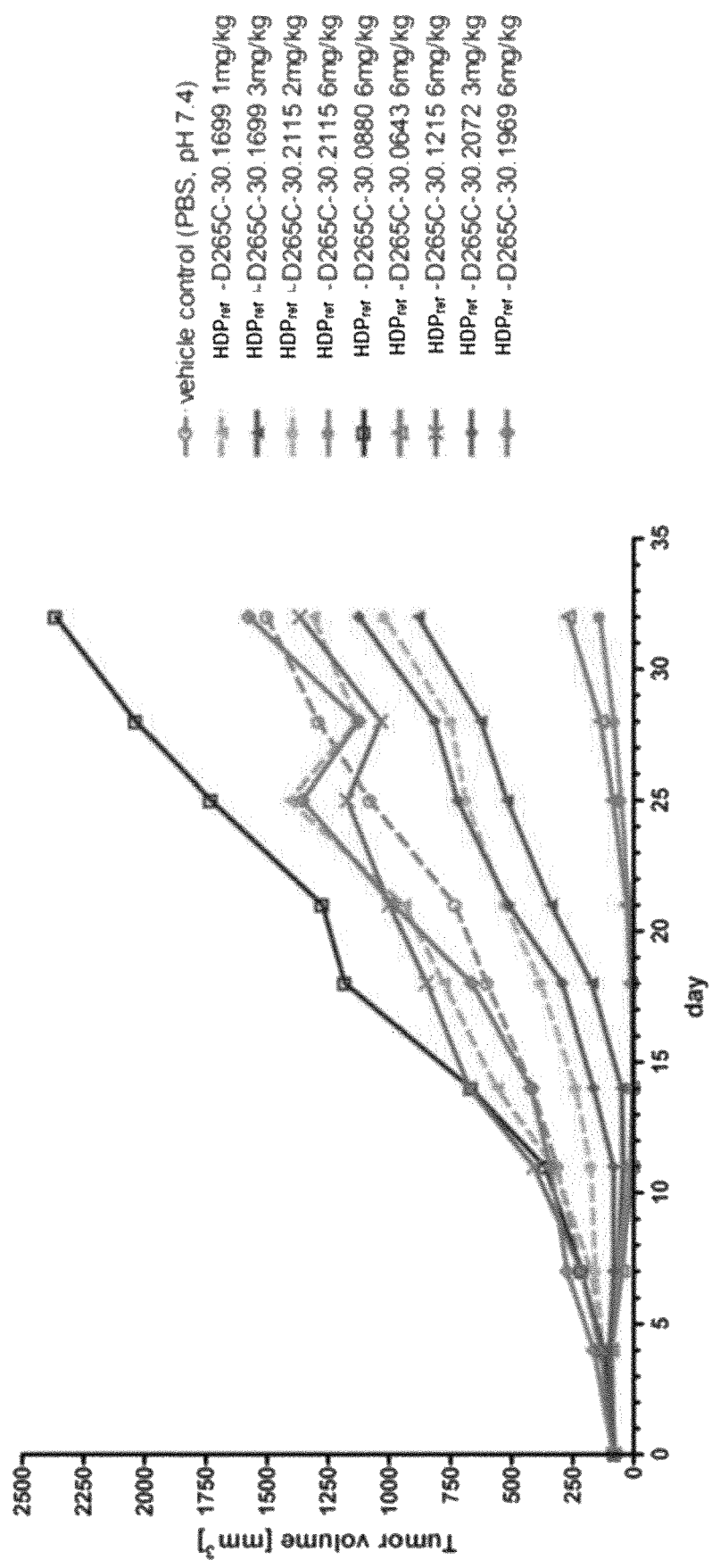
FIG. 13 compares the antitumoral activity of different amatoxin conjugates based on a tumor-targeting reference antibody ($HDP_{ref}$)—in a xenograft model—single dose experiment. Depending on linker and toxin structure significant differences in antitumoral activity have been observed. The deoxy-amanin variant $HDP_{ref}$-30.2115 (6'-deoxy at amino acid 4 and S-deoxy at amino acid 8) showed best antitumoral activity of all amatoxin ADCs, with a significantly better therapeutic index than corresponding cleavable linker ADC $HDP_{ref}$-30.1699 (lysine conjugation via 6'-OH; S═O at amino acid 8).
Figure 14:
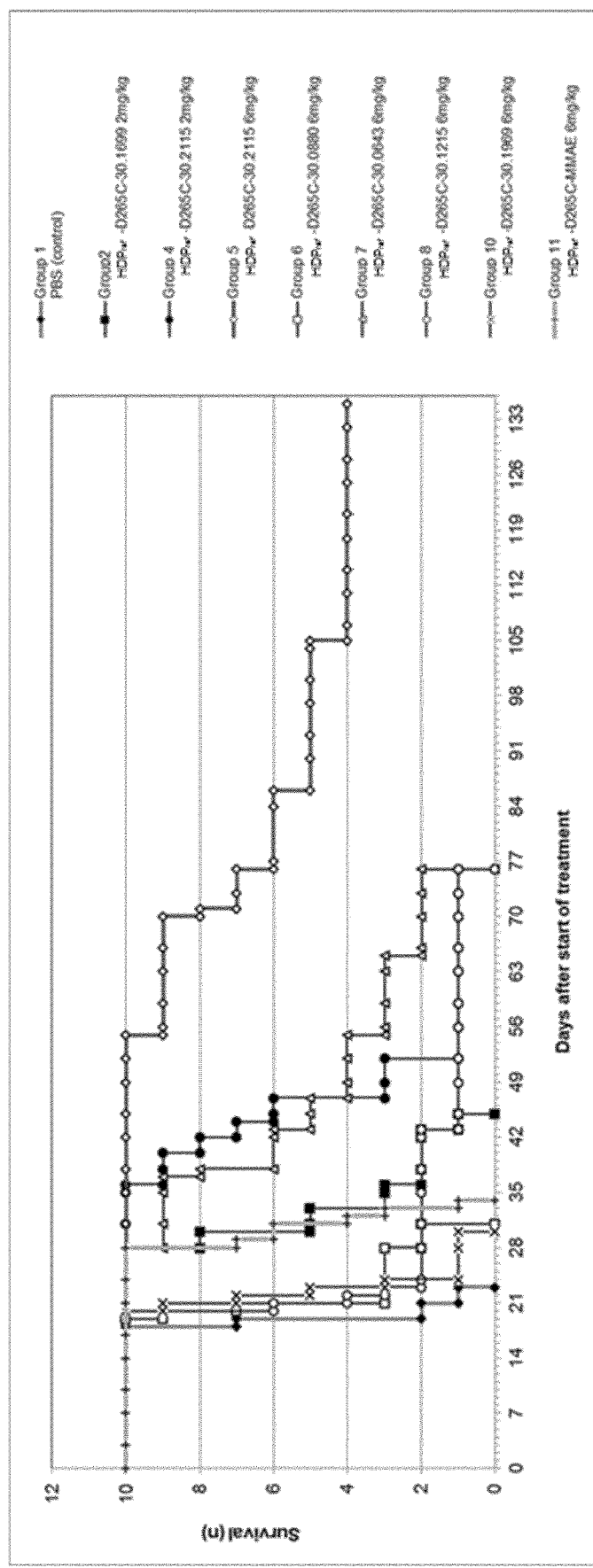
FIG. 14 shows the Kaplan Meier survival analysis in a systemic tumor model—single dose experiment with reference antibodies. In brief, $2.5 \times 10^6$ tumor cells in 200 μL PBS/mouse were inoculated intravenously on day 0. Therapy (single dose, iv) was initiated on day 3 post tumor cell inoculation. The deoxy-amanin variant $HDP_{ref}$-30.2115 (6'-deoxy at amino acid 4 and S-deoxy at amino acid 8) showed superior survival over $HDP_{ref}$-based conjugates with a-amanitin derivatives HDP 30.1699, HDP 30.0880 and HDP 30.0643 as well as with the corresponding MMAE-derivative.

An amatoxin variant comprising (i) an amino acid 4 with a 6'-deoxy position; and (ii) an amino acid 8 with an S-deoxy position was first mentioned in Zhou et al., ChemBioChem 16 (2015) 1420-1425, as one of four diastereomers being obtained in a total synthesis approach for amatoxins. However, the fact that such variants are more stable under stress conditions in plasma and result in a reduced degree of cross-linked products (as shown in FIG. 2) was not publicly known at the effective filing date of the present application in December 2016 (see patent application WO 2017/149077 published on Sep. 8, 2017).

In a particular embodiment, the conjugate of the present invention has a purity greater than 90%, particularly greater than 95%.

Monoclonal murine antibody J22.9 has been obtained using standard hybridoma technology from C57BL/6 mice immunized with purified human BCMA extracellular domain (residue 1-54) N-terminally fused to glutathione S-transferase (GST). Due to instability of the hybridomas, variable regions of light and heavy chain were amplified and cloned upstream of the human kappa and IgG1 constant domain, respectively, resulting in chimeric J22.9-xi antibody (Oden et al., 2015).

Antibody J22.9-xi was humanized based on sequence alignments and data obtained from crystal structure in order to identify mutations that would potentially disrupt the binding to BCMA. Briefly, J22.9-xi Fab fragment was generated from full-length antibody by incubation with pepsin and combined with purified 54 amino acid residue BCMA extracellular domain. Isolated complexes were used for crystallization studies and J22.9-xi BCMA binding epitopes were analysed in detail (WO2014/068079, WO2015/166073, Oden et al., 2015, Marino et al. 2016).

Based on these analyses, various combinations of fully humanized gene cassettes were identified and expressed as full-length antibody. J22.9-H is the fully humanized version of J22.9-xi. J22.9-ISY and J22.9-FSY are fully humanized versions containing in addition mutations intended to remove potentially detrimental post-translational modification (PTM) motifs.

J22.9-xi binds to purified BCMA and also detects BCMA on human MM cell lines MM.1S, NCI-H929, OPM-2 and RPMI-8226. No binding was detected on BCMA-negative cells. In addition, flow cytometry analyses revealed that cells from bone marrow of MM patients were detectable using J22.9-xi. The affinity of J22.9-xi to BCMA is very high with a mean Kd of 54 pM as determined using plasmon resonance (Oden et al., 2015).

BCMA activates nuclear factor KB (NFκB) pathways and triggers signals important for survival of MM and plasma cells through interaction with APRIL and/or BAFF. Affinity of J22.9 to BCMA was shown to be very high and exceeds that of April by 300- and of BAFF by 30.000-fold (Bossen and Schneider 2006). J22.9-xi efficiently blocks binding of APRIL and BAFF to BCMA. In addition, J22.9-xi interferes with APRIL-induced NFκB activation by blocking phosphorylation of IκB kinase (IKK) and subsequent IκBα degradation, leading to reduced DNA-binding activity of NFκB. In summary, J22.9-xi interferes with APRIL-induced NFκB activation in BCMA-positive NCI-H929 cells (Oden et al., 2015).

Cytotoxic activity of IgG1 antibodies is achieved through interaction of the IgG1 with Fcγ receptor (FcγR) on effector cells (e.g. natural killer cells) or with the C1q protein of the complement cascade. This interaction is dependent on glycosylation of the antibody at position Asn297 in the heavy chain constant region. Glycans on IgG1 display some heterogeneity but core structure is usually a fucosylated bi-antennary structure with varying levels of sialic acid at the antennae. Numerous investigations have shown that glycosylation affects binding affinity and loss of glycosylation completely abrogates binding altogether. Absence of glycosylation disrupts the structural integrity of the Fc region which is required for optimal binding to the Fcγ receptor (for review see Hayes et al., 2014). However, absence of core fucose of IgG results in improved binding to Fcγ receptor and enhanced antibody-dependent cellular cytotoxicity (ADCC).

Binding of the antibody to effector cells or complement results in ADCC mediated by natural killer cells or complement-dependent cytotoxicity (CDC). J22.9-xi is able to induce strong ADCC and CDC on BCMA-positive MM.1S cells when mixed with isolated Fc-bearing effector, peripheral blood mononuclear cells (PBMCs) from healthy donors.

Humanized and chimeric antibody variants bind to BCMA-expressing cell lines. No differences in binding characteristics were observed for J22.9-ISY and J22.9-FSY, whereas binding affinity of humanized variant J22.9-H was much lower.

In the context of the present invention, the term "purity" refers to the total amount of conjugates being present. A purity of greater than 90%, for example, means that in 1 mg of a composition comprising a conjugate of the present invention, there are more than 90%, i.e. more than 900 μg, of such conjugate. The remaining part, i.e. the impurities may include unreacted starting material and other reactants, solvents, cleavage products and/or side products.

In a particular embodiment, a composition comprising a conjugate of the present invention comprises more than 100 mg of such conjugate. Thus, trace amount of a conjugate of the present invention that arguably may be present in complex preparations of conjugates of the prior art, e.g. from partial reduction of naturally occurring sulfoxides, are explicitly excluded.

As used herein, a first compound (e.g. an antibody) is considered to "specifically bind" to a second compound (e.g. an antigen, such as a target protein), if it has a dissociation constant $K_D$ to said second compound of 100 μM or less, particularly 50 μM or less, particularly 30 μM or less, particularly 20 μM or less, particularly 10 μM or less, particularly 5 μM or less, more particularly 1 μM or less, more particularly 900 nM or less, more particularly 800 nM or less, more particularly 700 nM or less, more particularly 600 nM or less, more particularly 500 nM or less, more particularly 400 nM or less, more particularly 300 nM or less, more particularly 200 nM or less, even more particularly 100 nM or less, even more particularly 90 nM or less, even more particularly 80 nM or less, even more particularly 70 nM or less, even more particularly 60 nM or less, even more particularly 50 nM or less, even more particularly 40 nM or less, even more particularly 30 nM or less, even more particularly 20 nM or less, and even more particularly 10 nM or less.

The term "antibody or antigen binding fragment thereof", as used herein, refers to immunoglobulin molecules and immunologically active portions of immunoglobulin molecules, i.e. molecules that contain an antigen-binding site that immunospecifically binds the antigen BSMA. Thus, the term "antigen-binding fragments thereof" refers to a fragment of an antibody comprising at least a functional antigen-binding domain. In a particular embodiment, functional antigen-binding domain comprises the variable domains of the heavy chain according to SEQ ID NO: 1 and the light chain according to SEQ ID NO: 2 of antibody J22.9-ISY. Also comprised are immunoglobulin-like proteins that are selected through techniques including, for example, phage display to specifically bind to the antigen BSMA. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, F(ab')$_2$ fragments, fragments produced by a Fab expression library, diabodies or tetrabodies (Holliger P. et al., Proc Natl Acad Sci USA. 90 (1993) 6444-8), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and F(ab')$_2$, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains. In a particular embodiment, the antibody or antigen binding fragment thereof comprises a heavy chain constant region comprising a D265C mutation.

Antibodies usable in the invention may be from any animal origin including birds and mammals. Particularly, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

In a second aspect, the present invention relates to a pharmaceutical composition comprising the conjugate of the present invention.

In a third aspect, the present invention relates to the conjugate of the present invention, or the pharmaceutical composition of the present invention, for use in the treatment of cancer in a patient, particularly wherein the cancer is selected from the group consisting of multiple myeloma, diffuse large B-cell lymphoma (DLBCL), and chronic lymphocytic leukemia (CLL), particularly multiple myeloma.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising an amatoxin according to the present invention, or a conjugate of the present invention of an amatoxin with a target-binding moiety, and further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The amatoxins of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are particularly aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

EXAMPLES

In the following, the invention is explained in more detail by non-limiting examples:

Example 1

Synthesis of Amatoxin-Linker HDP 30.2115

Linkage of antibody to toxin can occur either to cysteine or lysine residues, a specific tag or non-nat of the antibody. In order to obtain homogenous ADC products with specific DAR of 2, site-specific conjugation to cysteine in combination with genetic engineered Thiomabs is preferred. Key attributes of the linker include the requirement to be stable in plasma in order to prevent the uncontrolled release of the toxic payload into the circulation, and on the other hand the toxin needs to be released within the cell after internalization of the ADC upon target binding. Release of the toxin inside the target cell can occur either via cleavable or non-cleavable linkers. Cleavable linkers can be cleaved from the payload via a variety of mechanism including acidic degradation as consequence of lower pH inside the cell compared to circulation and protease cleavage by the protease cathepsin B or thiol-disulfide exchange attributed to the more reductive intracellular environment. Non-cleavable linkers require complete lysosomal proteolytic degradation generating a payload with a charged lysine or cysteine residue from the antibody.

The main advantage of non-cleavable compared to cleavable linkers is their increased plasma stability. While it is apparent that activities of ADCs containing non-cleavable linkers are less predictable, cleavable linkers raise the concerns of non-specific cytotoxicity.

However, in previous experiments, particularly in vitro experiments, with numerous different linkers, ADCs containing non-cleavable linkers have been shown to be less toxic than ADCs with a cleavable linker, and the majority of amanitin-based ADCs based on cleavable linkers were more effective compared to non-cleavable linker constructs. Thus, a cathepsin B-cleavable linker has been chosen for the drug substance.

The α-amanineamide-linker-toxin HDP 30.2115 is synthesized by a multistep approach using solid phase peptide synthesis whereas the bicyclic octapeptide is initially assembled in a linear fashion. Starting point is a hydroxyproline resin immobilisation, followed by C-terminal coupling of dihydroxyisoleucin (HDP 30.0477). The remaining six amino acids are coupled by Fmoc strategy. The first cyclisation (right hand ring) occurs upon acidic cleavage from resin following the 'Savige-Fontana' mechanism. To make this happen, Tryptophan is incorporated in its oxidized form, 'HPI' (HDP 30.0079), as final amino acid. The second ring is formed by macrolactamisation using moderate to high dilution. The linker compound (HDP 30.2109) is synthesized in six linear steps and is finally introduced under standard coupling conditions, after deprotection.

1. Synthesis of Synthetic Dideoxy Precursor Molecule K

The synthesis of the dideoxy precursor molecule K is described in WO 2014/009025 in Example 5.5.

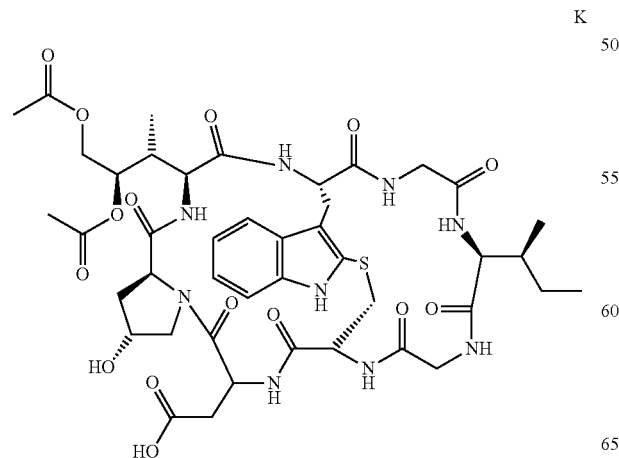

K

Compound K may be deprotected by treatment with 7 N methanolic $NH_3$ solution (3.0 ml) and stirring overnight.

2. Synthesis of Synthetic Dideoxy Precursor HDP 30.2105

An alternative dideoxy precursor molecules comprising a —COOH group instead of the carboxamide group at amino acid 1 can be synthesized (HDP 30.1895) and deprotected to result in HDP 30.2105.

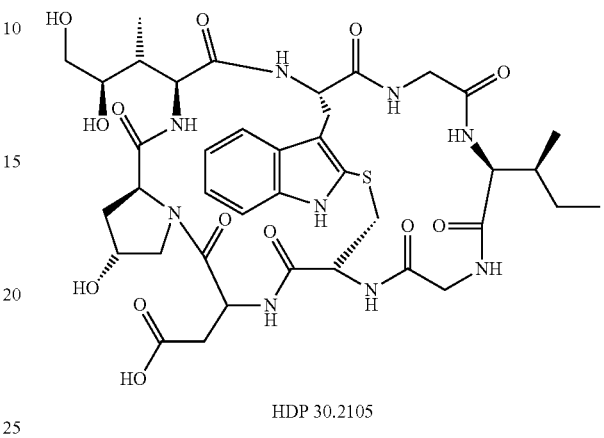

HDP 30.2105

Step 1: 4-Hydroxy-pyrrolidine-1,2-dicarboxylic acid 2-allyl ester 1-(9H-fluoren-9-ylmethyl) ester (HDP 30.0013)

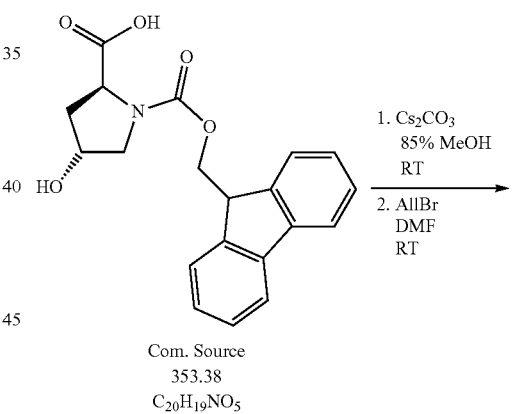

Com. Source
353.38
$C_{20}H_{19}NO_5$

1. $Cs_2CO_3$
   85% MeOH
   RT
2. AllBr
   DMF
   RT

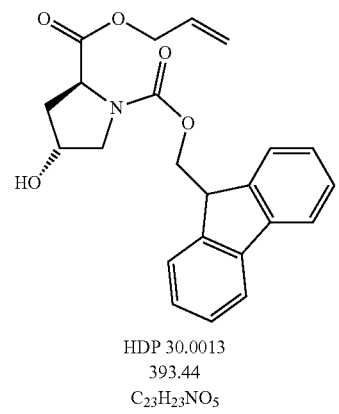

HDP 30.0013
393.44
$C_{23}H_{23}NO_5$

FmocHypOH (10.0 g, 28.3 mmol) was suspended in 100 ml 80% MeOH and Cs2CO3 (4.6 g, 14.1 mmol) was added.

The suspension was stirred at 50° C. for 30 minutes until complete dissolution. The reaction mixture was concentrated to dryness and resolved in 100 ml DMF. Allylbromide (1.6 ml, 3.6 g, 29.7 mmol) was added dropwise and the reaction was stirred over night at RT. DMF was distilled off and the residue dissolved in tert-butylmethyl ether. Precipitates were filtered and the clear solution was absorbed on Celite prior column chromatography. The compound was purified on 220 g Silicagel with an n-hexane/ethyl acetate gradient.

Yield: 11.5 g, 100%

Step 2: Resin Loading (HDP 30.0400)

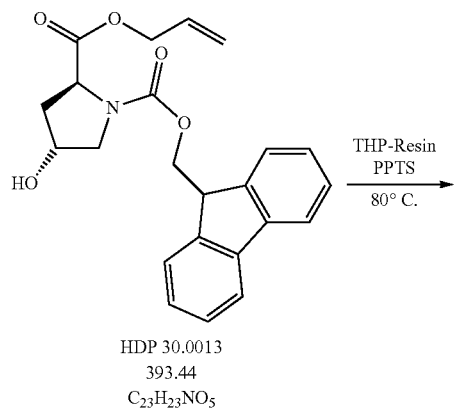

HDP 30.0013
393.44
$C_{23}H_{23}NO_5$

THP-Resin
PPTS
─────────→
80° C.

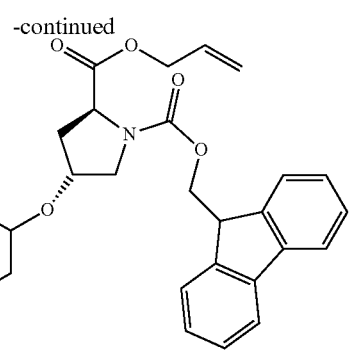

HDP 30.0040
393.44
$C_{23}H_{23}NO_5$

HDP 30.0013 (5.0 g, 14.1 mmol), pyridinium 4-toluene-sulfonate (1.33 g, 5.3 mmol) were added to a suspension of 1,3-dihydro-2H-pyran-2-yl-methoxymethyl resin (5.0 g, 1.0 mmol/g THP-resin) in 40 ml dichloroethane. The reaction was stirred at 80° C. overnight. After cooling the resin was filtered and extensively washed with dichloroethane, dimethylformamide, acetonitrile, dichloromethane and tert-butylmethylether.

Loading was 0.62 mmol/g (determined by UV-spectroscopy of the fluorene methyl group after deprotection).

Step 3: Solid Phase Precursor Synthesis (HDP 30.1894)

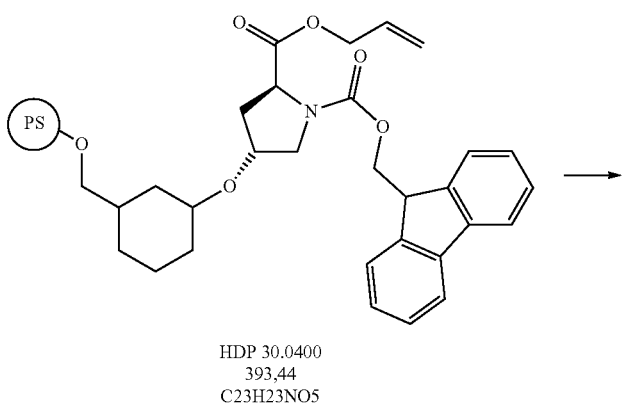

HDP 30.0400
393,44
C23H23NO5

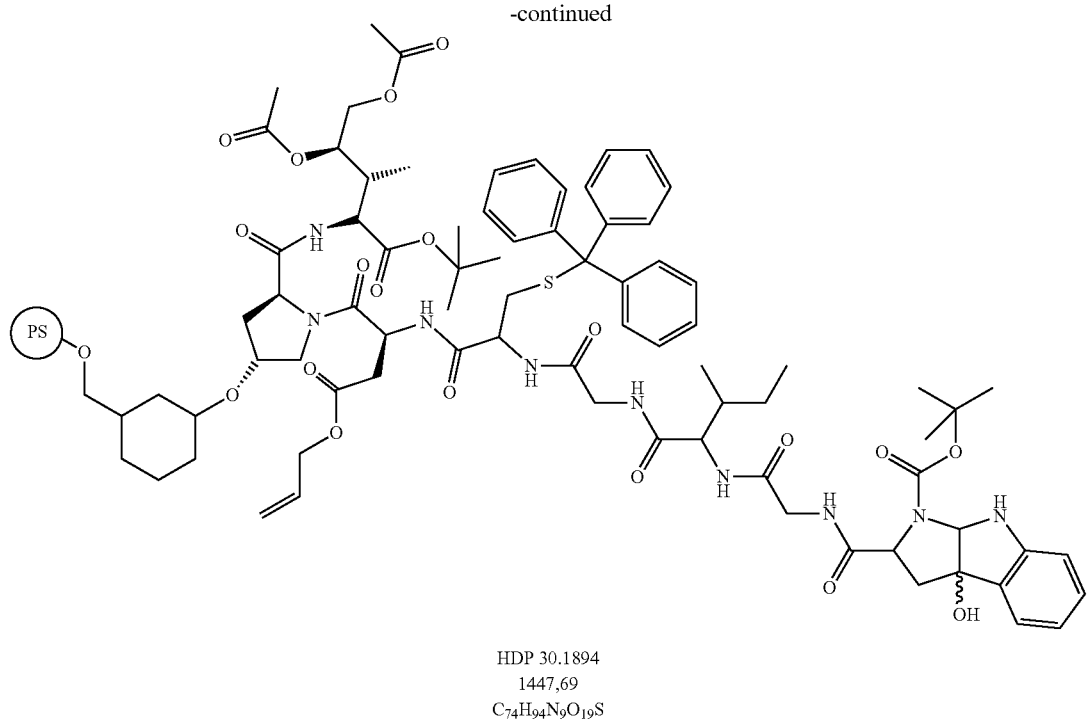

HDP 30.1894
1447,69
C$_{74}$H$_{94}$N$_9$O$_{19}$S

Resin Pre-Treatment:

HDP 30.0400 (0.5 g, 0.31 mmol) was treated with N,N-dimethylbarbituric acid (483 mg, 3.1 mmol) and Pd(PPh3)4 (69 mg, 0.06 mmol). The resin was shaken over night at RT. Thereafter the resin was extensively washed with dichloromethane, N-methyl-2-pyrrolidone, acetonitrile, dichloromethane and tert-butylmethyl ether and dried under reduced pressure.

Coupling Procedure:

All reactants and reagents were dissolved in dichloromethane/N-methyl-2-pyrrolidone containing 1% Triton-X100 (Solvent A).

HDP 30.0477 (257 mg, 0.38 mmol) was dissolved in 3.0 ml Solvent A and treated with 3.0 ml of a 0.2 N solution PyBOP (333 mg, 0.63 mmol, 2.0 eq), 3.0 ml of a 0.2 N solution HOBt (130 mg, 0.63 mmol, 2.0 eq) and 439 µl DIEA (4.0 eq). The reaction was heated to 50° C. for 8 minutes by microwave irradiation (20 W, CEM microwave reactor) and was washed with N-methyl-2-pyrrolidone after coupling.

Deprotection:

Deprotection was performed by addition of 6.0 ml 20% piperidine in N-methyl-2-pyrrolidone at 50° C. for 8 minutes. The resin was washed with N-methyl-2-pyrrolidone (Note: No deprotection after coupling of the final amino acid).

All other amino acids were coupled following the above protocol, weightings are shown below:

0.63 mmol, 498 mg Fmoc Asp(OAll)OH
0.63 mmol, 738 mg Fmoc Cys(Tri)OH
0.63 mmol, 375 mg Fmoc GlyOH
0.63 mmol, 445 mg FmocIleOH
0.63 mmol, 375 mg Fmoc GlyOH
0.38 mmol, 242 mg N-Boc-HPIOH (HDP 30.0079)

4,5-Diacetoxy-2-amino-3-methyl-pentanoic acid tert-butyl ester; hydrochloride (HDP 30.0477) was synthesized as described in WO 2014/009025.

N-Boc-HPIOH (HDP 30.0079) was prepared according to Zanotti, Giancarlo; Birr Christian; Wieland Theodor; International Journal of Peptide & Protein Research 18 (1981) 162-8.

Step 4: HDP 30.1895

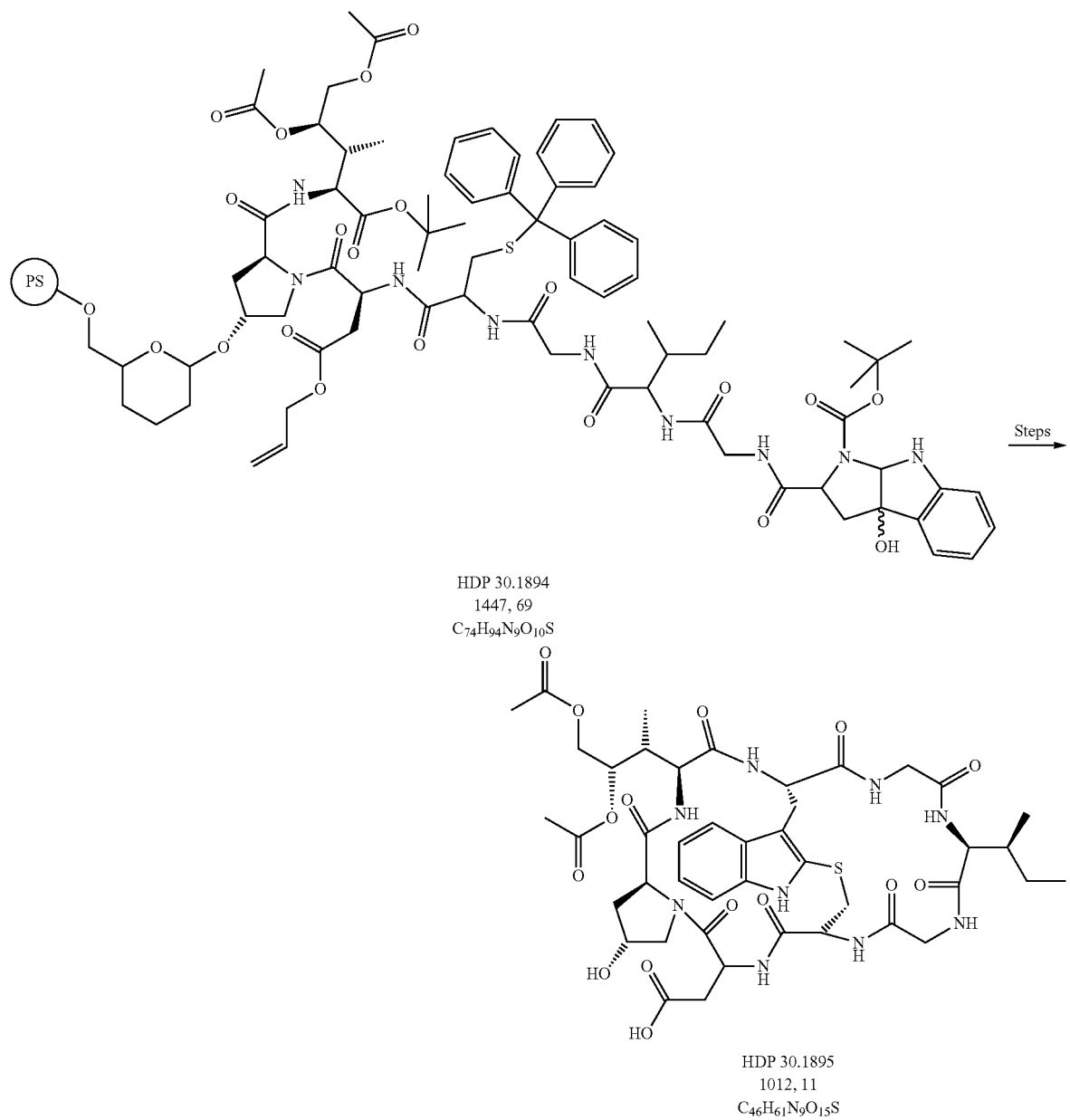

HDP 30.1894
1447, 69
$C_{74}H_{94}N_9O_{10}S$

HDP 30.1895
1012, 11
$C_{46}H_{61}N_9O_{15}S$

Elimination from Resin and B-Ring Formation

The resin was shaken with 10 ml trifluoroacetic acid/dichloromethane 50:50 (v/v) plus 10% methanol for 30 min and finally eluted into a 50 ml flask. The resin was washed twice with methanol (10 ml each). The combined eluates were concentrated in vacuum and re-suspended in 2-4 ml methanol. The methanolic solution was dropped twice into 50 ml cold diethyl ether for peptide precipitation. After centrifugation the precipitate was washed with diethyl ether (2 times) and dried under reduced pressure. The white precipitate was solubilized in approx. 4-5 ml methanol (0.5 ml per 100 mg) and purified by preparative reverse phase column chromatography. Approximately 100 mg crude precipitate were purified per run. Fractions were analyzed by mass spectrometry, combined and methanol distilled off under reduced pressure. The aqueous phase was freeze dried.

Yield: 24.4 mg, 23.7 µmol
Mass spectrometry: [M+H]+, 1030.5

A-Ring Formation

The above freeze dried intermediate was dissolved in 25 ml dimethylformamide and treated with diphenylphosphorylazide (63 µl, 1185 µmol, 5 eq) and diisopropylethyl amine (201 µl, 1185 µmol, 5 eq). The reaction was stirred overnight (20 hours). Conversion was monitored by reverse phase chromatography and finally quenched with 100 µl water. The mixture was concentrated by reduced pressure and re-dissolved in 1-2 ml methanol. Precipitation of the product was performed by dropwise addition to 20 ml diethyl ether.

The precipitate was washed twice with diethyl ether and dried under reduced pressure. The next step was performed without further purification.

Mass spectrometry: [M+Na]$^+$, 1034.6

Ester Deprotection:

To the crude cyclisation product 2.5 ml dichloromethane, diethylbarbituric acid (22.3 mg, 118.5 µmol) and Pd(PPh$_3$)$_4$ (27 mg, 23.7 µmol) were added. The reaction was stirred at RT overnight. The reaction can be monitored by RP-HPLC. After complete conversion, the mixture was added dropwise to 20 ml cooled diethyl ether and the precipitate washed twice with diethyl ether. After drying at reduced pressure the precipitate was dissolved in methanol (1.0 ml) and purified by preparative reversed phase chromatography.

Yield: 15.0 mg

Mass spectrometry: [M+H]$^+$, 972.3; [M+Na]$^+$, 994.5

Step 5: HDP 30.2105

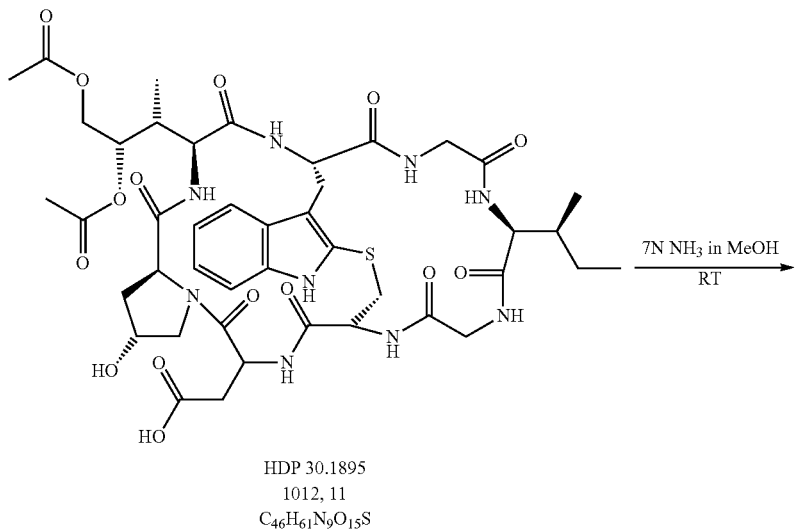

HDP 30.1895
1012, 11
C$_{46}$H$_{61}$N$_9$O$_{15}$S

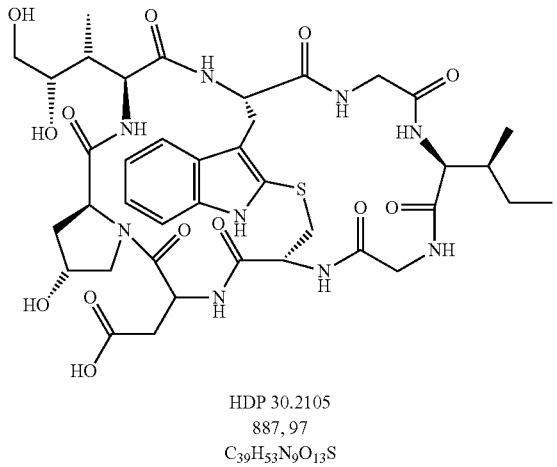

HDP 30.2105
887, 97
C$_{39}$H$_{53}$N$_9$O$_{13}$S

HDP 30.1895 (15.0 mg, 15.3 µmol) was dissolved in 7 N methanolic NH$_3$ solution (3.0 ml) and stirred overnight. Conversion was checked by mass spectrometry. After complete conversion the reaction was concentrated in vacuum, suspended in 80% tert-butanol and lyophilized. Product was purified by preparative HPLC.

Yield: 12.1 mg

Mass spectrometry: [M+H]$^+$, 888.0; [M+Na]$^+$, 910.2

3. Synthesis of Synthetic Dideoxy Precursor HDP 30.2115

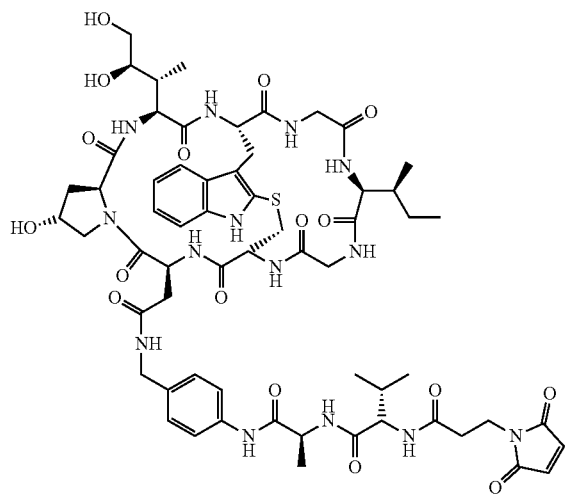

A dideoxy precursor molecule comprising a thiol reactive group with cleavable linker can be synthesized from example 2 product in 7 steps as follows:

Step 1: Fmoc-Val-OSu (HDP 30.1343)

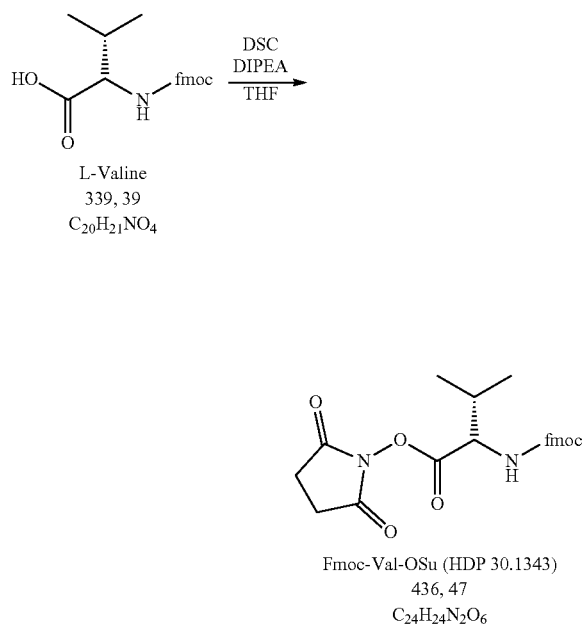

This compound is prepared according to R. A. Firestone et al, U.S. Pat. No. 6,214,345. Fmoc-Val-OH (20.24 g; 59.64 mmol) and N-hydroxysuccinimide (6.86 g=1.0 eq.) in tetrahydrofuran (200 ml) at 0° C. were treated with N,N'-dicyclohexylcarbodiimide (12.30 g; 1.0 eq.). The mixture was stirred at RT under argon atmosphere for 6 h and then the solid dicyclohexyl urea (DCU) by-product was filtered off and washed with THF and the solvent was removed by rotavap. The residue was dissolved in 300 ml dichloromethane, cooled in an ice bath for 1 h and filtered again to remove additional DCU. The dichloromethane was evaporated and the solid foam (26.51 g) was used in the next step without further purification.

Step 2: Fmoc-Val-Ala-OH (HDP 30.1414)

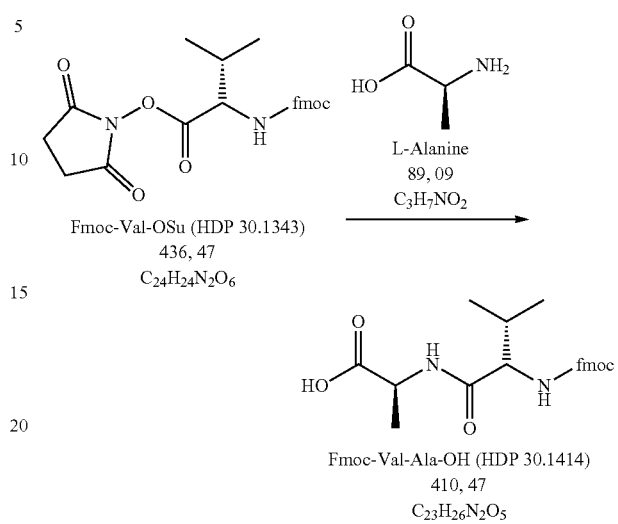

Step 2 product is prepared in analogy to P. W. Howard et al. US 2011/0256157. A solution of L-alanine (5.58 g; 1.05 eq.) and sodium hydrogen carbonate (5.51 g; 1.1 eq.) in 150 ml water was prepared and added to a solution of HDP 30.1343 (26.51 g; max. 59.6 mmol) in 225 ml tetrahydrofuran. The mixture was stirred for 50 h at RT. After consumption of starting material the solution was partitioned between 240 ml of 0.2 M citric acid and 200 ml of ethyl acetate. The aqueous layer was separated and extracted with ethyl acetate (3×200 ml). The combined organic layers were washed with water and brine (300 ml each) dried (MgSO$_4$) and the solvent was evaporated to approx. 200 ml. Pure product precipitated at this time and was filtered off. The mother liquor was evaporated to dryness and the residue was stirred 1 h with 100 ml MTBE to result additional crystalline material. The two crops of product were combined to 18.01 g (74%) white powder. (m.p.: 203-207° C.)

| MS (ESI+) | | |
|---|---|---|
| [M + Na]$^+$ found: 410.94; | calc.: 411.19 | (C$_{23}$H$_{27}$N$_2$O$_5$) |
| [M + Na]$^+$ found: 433.14; | calc.: 433.17 | (C$_{23}$H$_{27}$N$_2$O$_5$) |
| [2M + H]$^+$ found: 842.70; | calc.: 843.36 | (C$_{46}$H$_{52}$N$_4$NaO$_{10}$) |

Step 3: Fmoc-Val-Ala-PAB-NHBoc (HDP 30.1713)

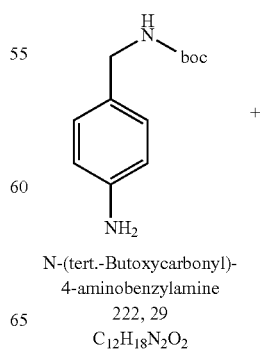

N-(tert.-Butoxycarbonyl)-
4-aminobenzylamine
222, 29
C$_{12}$H$_{18}$N$_2$O$_2$

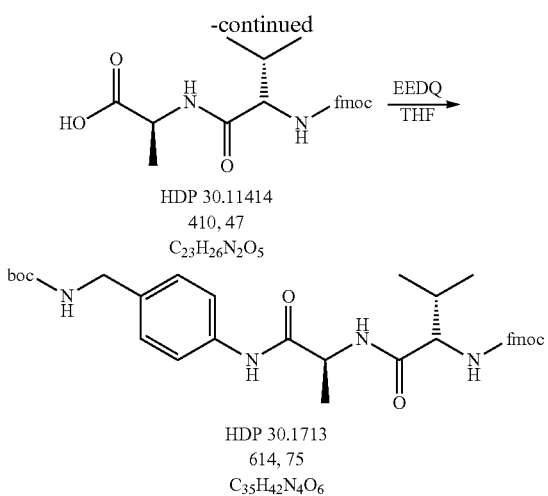

HDP 30.11414
410, 47
$C_{23}H_{26}N_2O_5$

HDP 30.1713
614, 75
$C_{35}H_{42}N_4O_6$

Step 2 product HDP 30.1414 (1.76 g; 4.28 mmol) and 4-[(N-Boc)aminomethyl]aniline (1.00 g; 1.05 eq.) were dissolved in 26 ml abs. tetrahydrofuran. 2-Ethoxy-N-(ethoxycarbonyl)-1,2-dihydroquinoline (EEDQ 1.11 g; 1.05 eq.) was added and the mixture was stirred at RT, protected from light. With ongoing reaction a gelatinous matter is formed from the initially clear solution. After 40 h the reaction mixture was diluted with 25 ml of tert-butylmethyl ether (MTBE) and stirred for 1 h. Subsequently the precipitation is filtered off with suction, washed with MTBE and dried in vacuo to 2.30 g (85% yield) of a white solid.

$^1$H NMR (500 MHz, DMSO-d6) δ 9.87 (s, 1H), 8.11 (d, J=7.1 Hz, 1H), 7.88 (d, J=7.5 Hz, 2H), 7.74 (q, J=8.4, 7.9 Hz, 2H), 7.51 (d, J=8.2 Hz, 2H), 7.45-7.23 (m, 7H), 7.17 (d, J=8.3 Hz, 2H), 4.44 (p, J=7.0 Hz, 1H), 4.36-4.17 (m, 3H), 3.96-3.89 (m, 1H), 2.01 (hept, J=6.9 Hz, 1H), 1.39 (s, 9H), 1.31 (d, J=7.1 Hz, 3H), 0.90 (d, J=6.8 Hz, 3H), 0.87 (d, J=6.8 Hz, 3H).

$^{13}$C NMR (126 MHz, DMSO-d6) δ 170.84, 170.76, 156.04, 155.63, 143.77, 143.69, 140.60, 137.41, 134.99, 127.50, 127.26, 126.93, 125.22, 119.95, 118.97, 77.60, 65.62, 59.95, 48.86, 46.62, 42.93, 30.28, 28.16, 19.06, 18.10, 18.03.

Step 4: H-Val-Ala-PAB-NHBoc (HDP 30.1747)

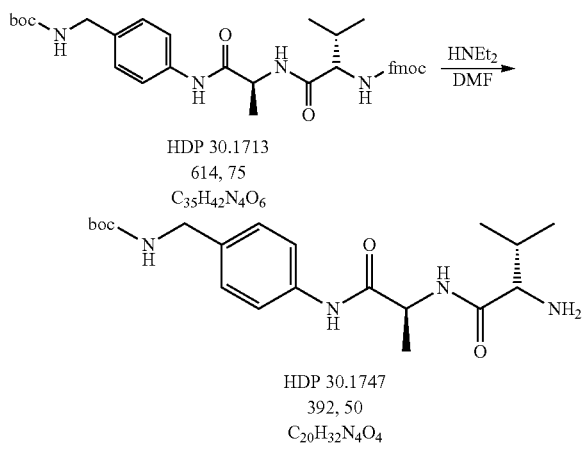

HDP 30.1713
614, 75
$C_{35}H_{42}N_4O_6$

HDP 30.1747
392, 50
$C_{20}H_{32}N_4O_4$

Step 3 compound HDP 30.1713 (1.230 g, 2.00 mmol) was placed in a 100 ml flask and dissolved in 40 ml dimethylformamide (DMF). Diethyl amine (7.5 ml) was added and the mixture was stirred at RT. The reaction was monitored by TLC (chloroform/methanol/HOAc 90:8:2). After consumption of starting material (30 min) the volatiles were evaporated and the residue was co-evaporated with 40 ml fresh DMF to remove traces of diethyl amine. The crude product was used without further purification for the next step.

| MS (ESI+) | | | |
|---|---|---|---|
| [MH]$^+$ | found: 393.26; | calc.: 393.25 | ($C_{20}H_{33}N_4O_4$) |
| [M + Na]$^+$ | found: 415.35; | calc.: 415.23 | ($C_{20}H_{32}N_4NaO_4$) |
| [2M + H]$^+$ | found: 785.37; | calc.: 785.49 | ($C_{40}H_{65}N_8O_8$) |

Step 5: BMP-Val-Ala-PAB-NHBoc (HDP 30.2108)

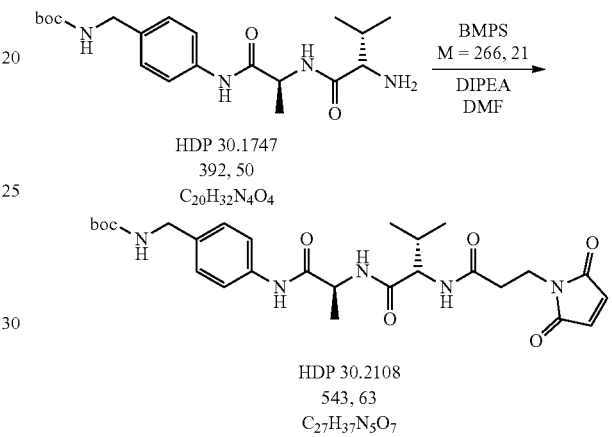

HDP 30.1747
392, 50
$C_{20}H_{32}N_4O_4$

HDP 30.2108
543, 63
$C_{27}H_{37}N_5O_7$

Crude step 4 product HDP 30.1747 (max 2.00 mmol) was dissolved in 40 ml DMF, 3-(maleimido)propionic acid N-hydroxysuccinimide ester (BMPS 532 mg; 1.0 eq.) and N-ethyldiisopropylamine (510 μl, 1.5 eq.) were added and the mixture was stirred 3 h at RT After consumption of starting material HDP 30.1747 (TLC: chloroform/methanol/HOAc 90:8:2) the volatiles were evaporated and the residue is stirred with 50 ml MTBE until a fine suspension was formed (1 h). The precipitate was filtered off with suction, washed with MTBE and dried. The crude product (1.10 g) was dissolved in 20 ml dichloromethane/methanol 1:1, kieselgur (15 g) was added and the solvents were stripped off. The solid material was placed on top of an 80 g silica gel column and eluted with a linear gradient of 0-10% methanol in dichloromethane. Product fractions were combined and evaporated to 793 mg (73% over two steps) amorphous solid.

MS (ESI$^+$) [M + Na]$^+$ found: 566.24; calc.: 566.26 ($C_{27}H_{37}NaO_7$)

$^1$H NMR (500 MHz, DMSO-d$_6$) δ 9.75 (s, 1H), 8.09 (d, J=7.1 Hz, 1H), 7.98 (d, J=8.4 Hz, 1H), 7.52 (d, J=8.6 Hz, 2H), 7.29-7.23 (m, 1H), 7.16 (d, J=8.5 Hz, 2H), 6.98 (s, 2H), 4.39 (p, J=7.1 Hz, 1H), 4.13 (dd, J=8.4, 6.7 Hz, 1H), 4.06 (d, J=6.1 Hz, 2H), 3.67-3.56 (m, 2H), 2.49-2.41 (m, 2H), 1.96 (h, J=6.8 Hz, 1H), 1.39 (s, 9H), 1.30 (d, J=7.1 Hz, 3H), 0.86 (d, J=6.8 Hz, 3H), 0.82 (d, J=6.8 Hz, 3H).

$^{13}$C NMR (126 MHz, DMSO-d$_6$) δ 170.80, 170.63, 170.60, 169.72, 155.65, 137.45, 134.94, 134.44, 127.26, 118.95, 77.62, 57.71, 48.92, 42.95, 33.96, 33.64, 30.17, 28.17, 19.02, 18.06, 17.82.

Step 6: BMP-Val-Ala-PAB-NH₂ (HDP 30.2109)

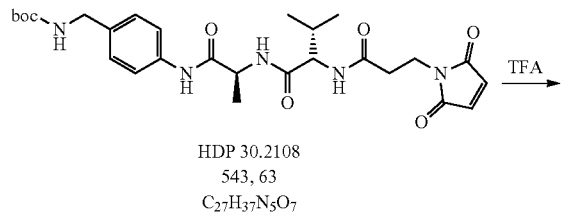

HDP 30.2108
543, 63
C₂₇H₃₇N₅O₇

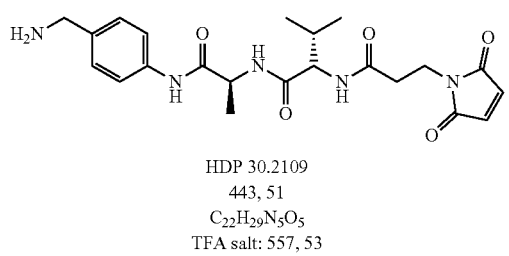

HDP 30.2109
443, 51
C₂₂H₂₉N₅O₅
TFA salt: 557, 53

Step 5 product HDP 30.2108 (400 mg, 736 μmol) was dissolved in 4,000 μl trifluoroacetic acid and stirred for 2 min. Subsequently the volatiles were evaporated at RT and the remainders were co-evaporated twice with 4,000 μl toluene. The residue was dissolved in 5,000 μl 1,4-dioxane/water 4:1, solidified in liquid nitrogen and freeze-dried: 410 mg (quant.) colorless powder.

| MS (ESI+) | [M + Na]⁺ found: 415.35; | calc.: 466.21 (C₂₂H₂₉NaO₅) |
|---|---|---|
| | [2M + H]⁺ found: 887.13; | calc.: 887.44 (C₄₄H₅₉N₁₀O₁₀) |

$^1$H NMR (500 MHz, DMSO-d$_6$) δ 9.89 (s, 1H), 8.13 (d, J=6.9 Hz, 1H), 7.99 (d, J=8.2 Hz, 1H), 7.66-7.60 (m, 2H), 7.41-7.34 (m, 2H), 6.98 (s, 2H), 4.39 (p, J=7.1 Hz, 1H), 4.11 (dd, J=8.2, 6.6 Hz, 1H), 3.97 (q, J=5.6 Hz, 2H), 3.69-3.58 (m, 2H), 2.49-2.40 (m, 2H), 1.96 (h, J=6.8 Hz, 1H), 1.32 (d, J=7.1 Hz, 3H), 0.86 (d, J=6.8 Hz, 3H), 0.83 (d, J=6.7 Hz, 3H).

$^{13}$C NMR (126 MHz, DMSO-d$_6$) δ 171.24, 170.78, 170.72, 169.85, 158.12 (q, J=33.2 Hz, TFA), 158.25, 157.99, 157.73, 139.19, 134.53, 129.45, 128.52, 119.02, 116.57 (q, J=296.7 Hz, TFA), 57.78, 49.08, 41.90, 34.00, 33.68, 30.21, 19.07, 18.16, 17.76.

Step 6: HDP 30.2115

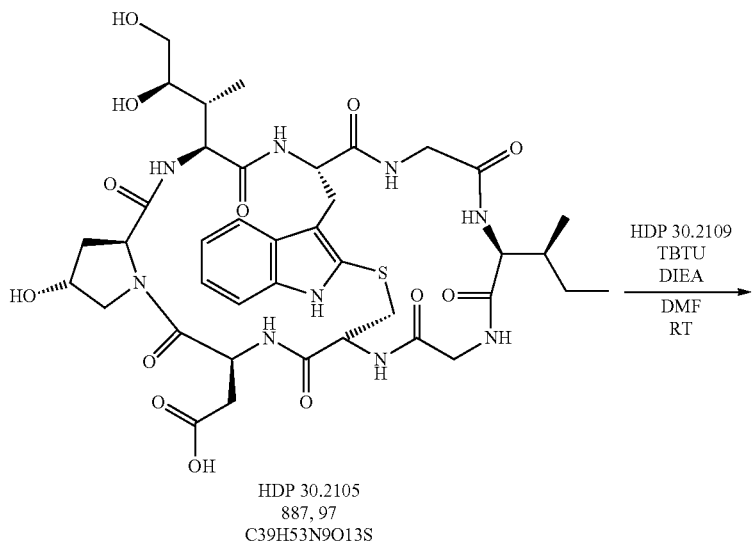

HDP 30.2105
887, 97
C39H53N9O13S

-continued

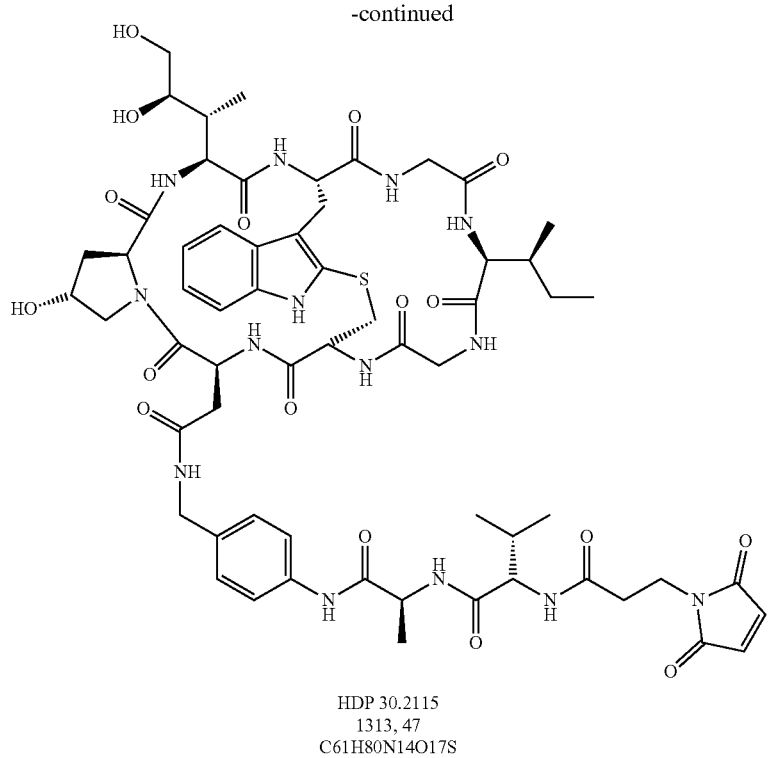

HDP 30.2115
1313, 47
C61H80N14O17S

HDP 30.2105 (15.0 mg, 16.5 μmol) were treated with 429 μl of a 0.1 M solution of HDP 30.2109 (25.2 μmol, 1.5 eq), 492 μl of 0.1 M TBTU (25.2 μmol, 1.5 eq) and 492 μl of 0.2 M DIEA (49.1 μmol, 3.0 eq) at RT. The reaction was monitored by RP-HPLC. After completion the reaction was quenched with 100 μl H$_2$O stirred for 15 minutes and injected onto a preparative RP-HPLC.

Yield: 12.2 mg, 56%

Mass spectrometry: 1313.2 [M+H]$^+$, 1335.5 [M+Na]$^+$

Example 2

Properties of Constructs Based on HDP 30.2105

Various experiments were performed to compare the properties of constructs based on di-deoxy amanitin derivative HDP 30.2105 with those of other amanitin variants. The results of these experiments are shown in FIGS. 2 to 14.

Example 3

Generation and Expression of Thiomab Antibody J22.9-ISY-D265C

Conjugation of the antibody with linker and toxin can occur to lysine or cysteine residues, resulting in highly variable drug-antibody ratio (DAR). Since potency and toxicity is strongly influenced by DAR, homogeneity and comparability of the ADC with predictable DAR is favourable. Antibodies with engineered reactive cysteine residues (thiomabs) allow for site-specific conjugation and therefore, amino acid aspartic acid at position 265 has been exchanged to cysteine (D265C). Thus, the resulting antibody variant contains two introduced cysteines at each chain of the Fc region, which serves as coupling site for the toxin-linker compound and allows production of ADCs with DAR=2.

Sequence modifications in the Fc-region of the antibody can have dramatic influence in linking antibody-mediated immune responses with cellular effector functions, since residues in the Fc-region are responsible for interaction with IgG Fcγ receptor (FcγR). Interactions of IgG with the FcγR play crucial role in cellular effector functions including release of inflammatory mediators, endocytosis of immune complexes, antibody-dependent cellular cytotoxicity (ADCC) and complement-dependent cytotoxicity (CDC). Preserving these effector functions in an ADC might contribute to the anti-tumor activity of the ADC. However, this assumption might prove to be incorrect as these effector functions are generally weak and, importantly, might compete with ADC internalization, reduce or abolish their specific toxin-related activity and increase off-target toxicity due to ADC uptake in antigen-negative cells via Fc-receptor. Several ADCs currently in pre-clinical and clinical development are based on IgG2 and IgG4 which are very inefficient in these effector functions (Trail, 2013; Peters and Brown, 2015).

Detailed mapping of binding sites on human IgG1 to FcγRI, FcγRII, FcγRIII and to neonatal Fc receptor (FcRn) revealed a crucial role of aspartic acid at position 265. Replacement of aspartic acid in IgG2 and IgG1 completely abolished interaction with FcγR (Baudino et al., 2008; Shields et al., 2001).

The efficiency of antibody-induced effector functions in Trastuzumab (Trademark Herceptin®) and corresponding thiomab antibodies with amino acid exchanges at position 265 (D265C) or 118 (T118C) for control were tested on a macrophage cell line THP-1. This monocytic cell line expresses multiple FcγRs and allows for testing antibody-mediated phagocytosis (Ackerman et al. 2011). Cytotoxicity on THP-1 cells was reduced by at least two orders of magnitude with thiomab D265C compared to thiomab A118C, containing a cysteine mutation at position A118 not reducing the effector function, and non-engineered antibody. This effect of reduced cytotoxicity with thiomab engineered at amino acid 265 is not due to conjugation of the toxin to the engineered cysteine, since, in contrast to T-D265C-30.1699 containing a cleavable linker conjugated to the engineered cysteine, in the case of T-D265C-30.0643 a stable linker is conjugated to lysine residues of the antibody. Thus, antibody-dependent effector functions were surprisingly highly reduced due to D265C exchange in thiomabs (see Table 1).

TABLE 1

| Compound | $EC_{50}$ [M] on THP-1 |
|---|---|
| T-D265C-30.0643 (stable linker; lysine coupling) | $1.9 \times 10^{-8}$ |
| T-D265C-30.0880 (stable linker; cysteine coupling) | $4.0 \times 10^{-8}$ |
| T-D265C-30.1699 (cleavable linker; cysteine coupling) | $2.0 \times 10^{-8}$ |
| T-A118C-30.0643 (stable linker; lysine coupling) | $2.8 \times 10^{-10}$ |
| T-A118C-30.0880 (stable linker; cysteine coupling) | $7.0 \times 10^{-10}$ |
| T-A118C-30.1699 (cleavable linker; cysteine coupling) | $4.4 \times 10^{-10}$ |
| Her-30.0880 (wild-type) | $4.6 \times 10^{-10}$ |
| Her-30.0643 (wild-type) | $1.2 \times 10^{-10}$ |

Results from characterization of the chimeric and sequence-optimized variants of J22.9 revealed improved binding properties of the sequence optimized variants J22.9-ISY and J22.9-FSY to BCMA compared to J22.9-H, with no obvious difference for ISY- or FSY-variant. Since use of plasmids expressing J22.9-ISY antibody variant resulted in improved titers when transiently expressed in cell culture, variant J22.9-ISY was chosen for conjugation and further evaluation.

The nucleic acid coding sequence for the heavy chain of monoclonal antibody J22.9-ISY-D265C was obtained from the heavy chain sequence of humanized antibody J22.9-ISY (see WO 2014/068079 and WO 2015/166073) as described in WO 2016/142049. In addition to the exchange D265C, J22.9-ISY-D265C additionally contains a mutation R214K (see SEQ ID NO: 1).

In order to produce amanitin-conjugate J22.9-ISY-D265C-30.2115, antibody J22.9-ISY-D265C was transiently expressed in Expi293F™ cells co-transfected with plasmids for the heavy and light chain. In an additional approach, antibody J22.9-ISY-D265C was produced in CHO cells stably transfected with plasmids expressing heavy and light chain. The antibody was purified from the cell culture supernatant using protein A chromatography followed by gel filtration. Antibody produced transiently from Expi293F™ or from stable CHO cells are comparable conjugation to payload, in binding to BCMA and cytotoxicity on BCMA-expressing cells.

Figure 15:
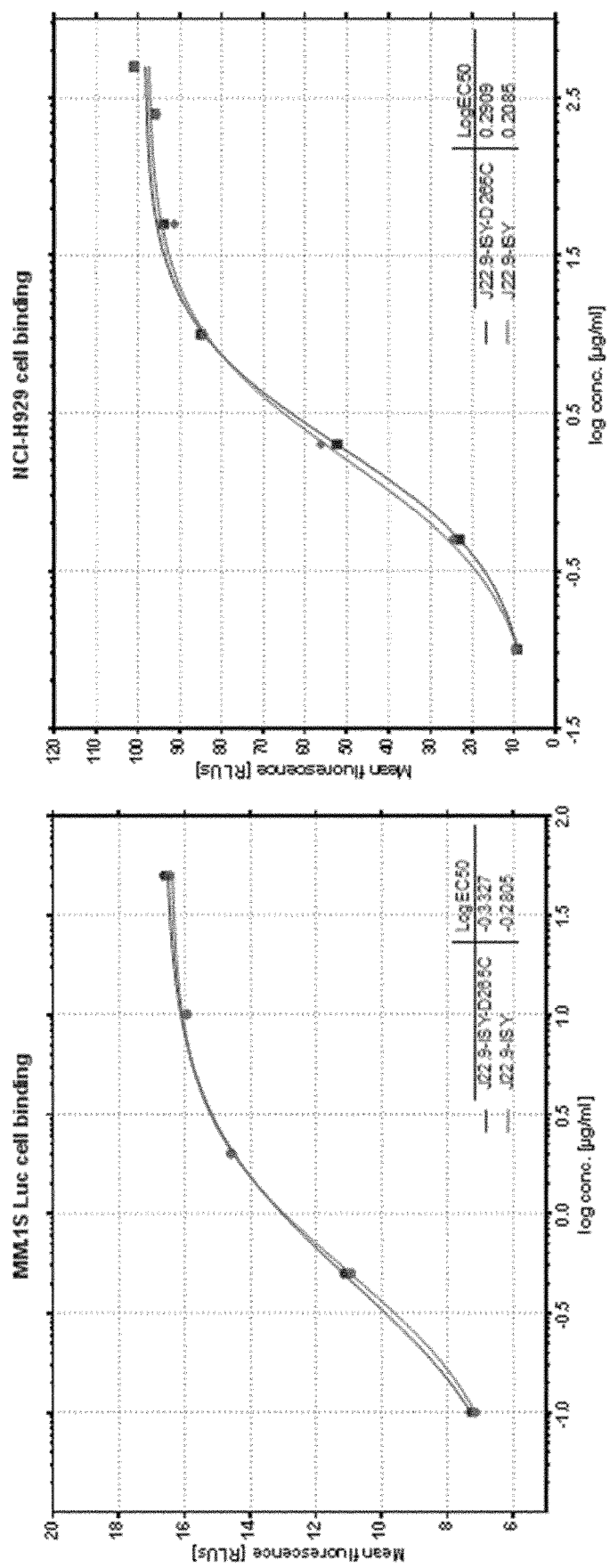
FIG. 15 shows that J22.9-ISY and thiomab J22.9-ISY-D265C have comparable binding properties to BCMA-positive cells. The results of a flow cytometry-binding assays of antibody variants J22.9-ISY and J22.9-ISY-D265C revealed comparable binding properties to BCMA-expressing MM.1S Luc and NCI-H929 cells.

In order to test if amino acid exchange in Thiomab J22.9-ISY-D265C did not interfere with binding to BCMA, binding of J22.9-ISY and J22.9-ISY-D265C to BCMA-expressing cells was compared. The binding property of the engineered thiomab J22.9-ISY-D265C to BCMA-positive NCI-H929 and MM.1S-Luc cells was identical to J22.9-ISY antibody (see FIG. 15).

Example 4

Synthesis of Conjugate J22.9-ISY-D265C-30.2115

Conjugation of HDP 30.2115 to 10 mg J22.9-ISY-D265C 10 mg Thiomab J22.9-ISY-D265C in PBS buffer will be used for conjugation to HDP 30.2115.

Adjust antibody solution to 1 mM EDTA:
2 ml antibody solution (10.0 mg)+20 µl 100 mM EDTA, pH 8.0
Amount antibody: 10 mg=$6.8\times10^{-8}$ mol
Uncapping of cysteines by reaction of antibody with 40 eq. TCEP:
2 ml antibody solution ($6.8\times10^{-8}$ mol)+54.5 µl 50 mM TCEP solution ($2.72\times10^{-6}$ mol)
Incubate for 3 h at 37° C. on a shaker.
Two consecutive dialyses at 4° C. in 2.0 1 1×PBS, 1 mM EDTA, pH 7.4 in a Slide-A-Lyzer Dialysis Cassette 20'000 MWCO, first dialysis ca. 4 h, second dialysis overnight
Concentrate to ca. 4.0 ml using Amicon Ultra Centrifugal Filters 50'000 MWCO.
Oxidation by reaction of antibody with 20 eq. dehydroascorbic acid (dhAA):
ca. 2 ml antibody solution ($6.8\times10^{-8}$ mol)+27.2 µl fresh 50 mM dhAA solution ($1.36\times10^{-6}$ mol)
Incubate for 3 h at RT on a shaker.
Conjugation with amanitin using 4 eq. HDP 30.2115 and quenching with 25 eq. N-acetyl-L-cysteine:
Solubilize 0.7 mg HDP 30.2115 in 70 µl DMSO=10 µg/µl
ca. 2 ml antibody solution (=9.5 mg; $6.54\times10^{-8}$ mol)+34.4 µl HDP 30.2115 (=344 µg; $2.62\times10^{-7}$ mol).
Incubate 1 h at RT.
Quench by addition of 16.4 µl 100 mM N-acetyl-L-cysteine ($1.64\times10^{-6}$ mol).
Incubate 15 min at RT (or overnight at 4° C.).
Purify reaction mix with 1× PD-10 columns equilibrated with 1×PBS, pH 7.4. Identify protein-containing fractions with Bradford reagent on parafilm and bring protein-containing fractions together.
Dialysis of antibody solution at 4° C. overnight in 2.0 l PBS, pH 7.4 and Slide-A-Lyzer Dialysis Cassettes 20'000 MWCO.
Determination of protein concentration by UV-spectra (absorption at 280 nm).
Determination of DAR by LC-ESI-MS-analysis.
Adjust protein concentration to 5.0 mg/ml ($3.4\times10$-5 M) and bring to sterile conditions by filtration. Store at 4° C.

Example 5

Characterization of Drug Substance J22.9-ISY-D265C-30.2115

1. Production and Release Testing

In order to characterize an ADC variant based on HDP 30.2115, it was compared to a variant based on HDP 30.1699 (see Table 1).

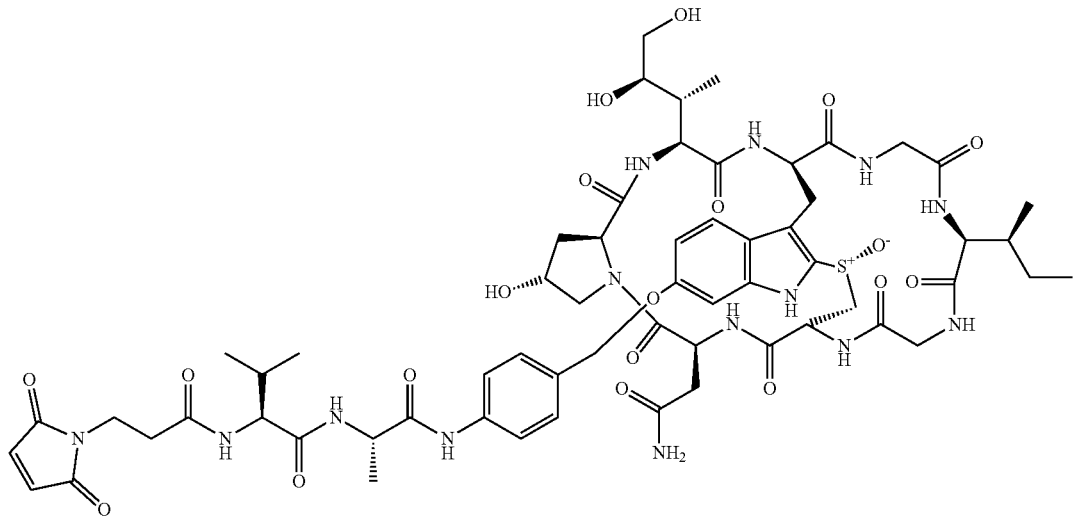

HDP 30.1699

HDP 30.1699 contains amanitin from natural source in contrast to fully synthetic amanitin derivative HDP 30.2115. Due to the chemical synthesis, there are the following differences between the two compounds: HDP 30.2115 contains a thioether bridge and a core tryptophan moiety, whereas HDP 30.1699 contains a sulfoxide bridge and a 6-hydroxytryptophan moiety. The absence of 6-hydroxytryptophan in HDP 30.2115 requires linkage of the antibody to the aspartic acid in contrast to HDP 30.1699 were 6-hydroxytryptophan is used for the linkage. In both compounds a cathepsin B cleavable linker was used.

Antibody J22.9-ISY-D265C was conjugated to compounds HDP 30.1699 and HDP 30.2115 using maleimido-chemistry as described above and tested for aggregates, DAR and product quality in analytical SEC-HPLC, Mass spectrometry, SDS-Page and Western Blot.

Test results from B16-0040 and B16-0049 are presented exemplarily in FIG. 16.

Figure 17:
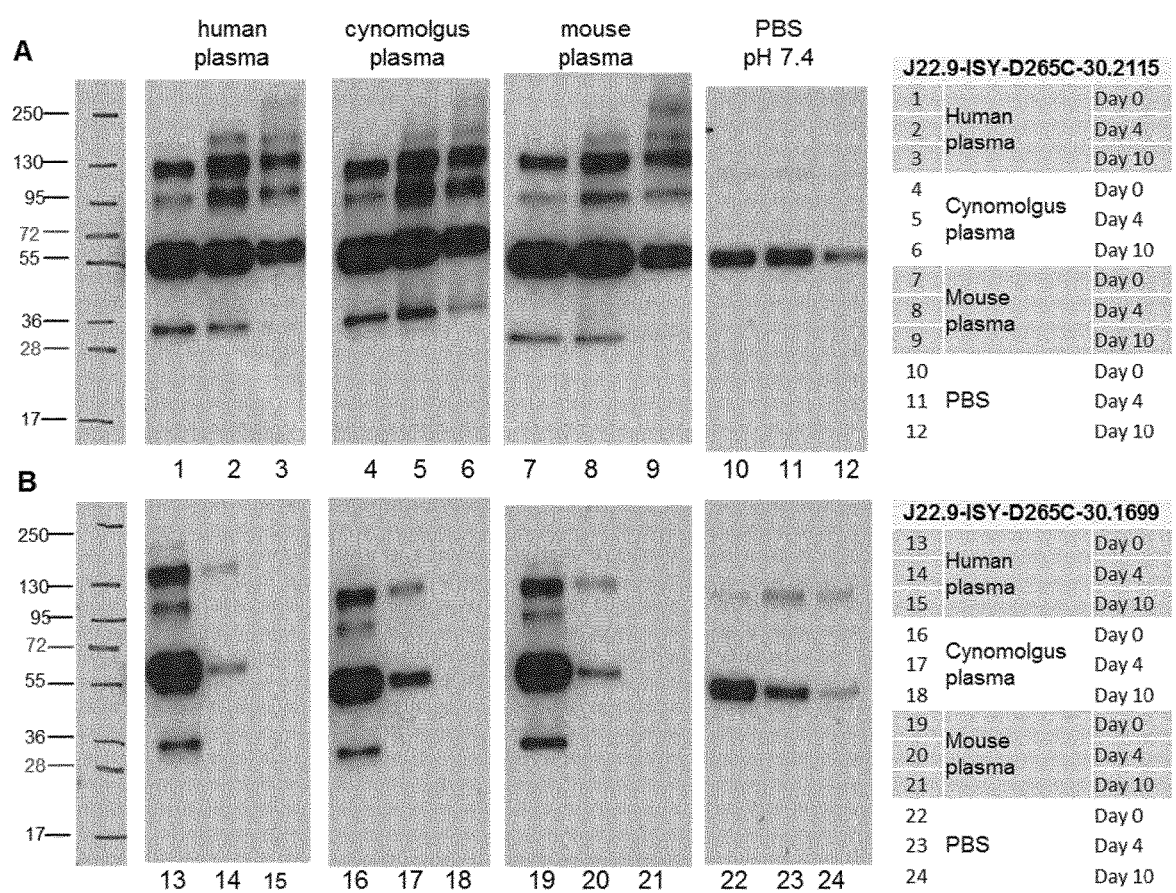
FIG. 17 shows the results of stability experiments: J22.9-ISY-D265C-30.2115 (A) and J22.9-ISY-D265C-30.1699 (B) were incubated in human, cynomolgus, or mouse plasma or PBS for control for 0, 4, and 10 days at 37° C. and analysed in reducing SDS-PAGE and subsequent anti-amanitin Western Blot.

Stability of J22.9-ISY-D265C-30.2115 and J22.9-ISY-D265C-30.1699 was tested following incubation at 37° C. for 0, 4, and 10 days in PBS, human, cynomolgus or mouse plasma. In contrast to J22.9-ISY-D265C-30.1699, Western Blot analyses surprisingly revealed a particularly high stability throughout the time course of the experiment for J22.9-ISY-D265C-30.2115 in PBS or plasma (see FIG. 17).

Thus the ADC-containing the synthetic amanitin-derivative showed superior stability compared to the ADC with amanitin from natural source.

Plasma stability of both ADC variants was confirmed in a cell-based cytotoxicity assay on BCMA-positive NCI-H929 cells (see Table 2) after incubation for 0, 4 and 10 days in PBS, human, cynomolgus or mouse plasma. Incubation in PBS or plasma over up to 10 days has almost no influence on the cytotoxic potential of J22.9-ISY-D265C-30.2115. In contrast, the cytotoxicity and thus the stability of J22.9-ISY-D265C-30.1699 was clearly reduced after incubation in human, cynomolgus or mouse plasma, as already observed in Western Blot analyses (see FIG. 18).

TABLE 2

| $EC_{50}$ | | human plasma | cynomolgus plasma | mouse plasma | PBS pH 7.4 |
|---|---|---|---|---|---|
| J22.9-ISY-D265C-30.2115 | day 0 | $2.8 \times 10^{-10}$ | $2.5 \times 10^{-10}$ | $1.2 \times 10^{-10}$ | $2.4 \times 10^{-10}$ |
| | day 4 | $2.7 \times 10^{-10}$ | $2.5 \times 10^{-10}$ | $1.8 \times 10^{-10}$ | $2.4 \times 10^{-10}$ |
| | day 10 | $1.0 \times 10^{-9}$ | $2.9 \times 10^{-10}$ | $6.0 \times 10^{-10}$ | $4.1 \times 10^{-10}$ |
| J22.9-ISY-D265C-30.1699 | day 0 | $1.8 \times 10^{-10}$ | $2.0 \times 10^{-10}$ | $8.6 \times 10^{-11}$ | $1.6 \times 10^{-10}$ |
| | day 4 | $3.7 \times 10^{-7}$ | $2.1 \times 10^{-9}$ | $2.0 \times 10^{-9}$ | $3.6 \times 10^{-10}$ |
| | day 10 | — | — | — | $6.0 \times 10^{-10}$ |

Figure 19:
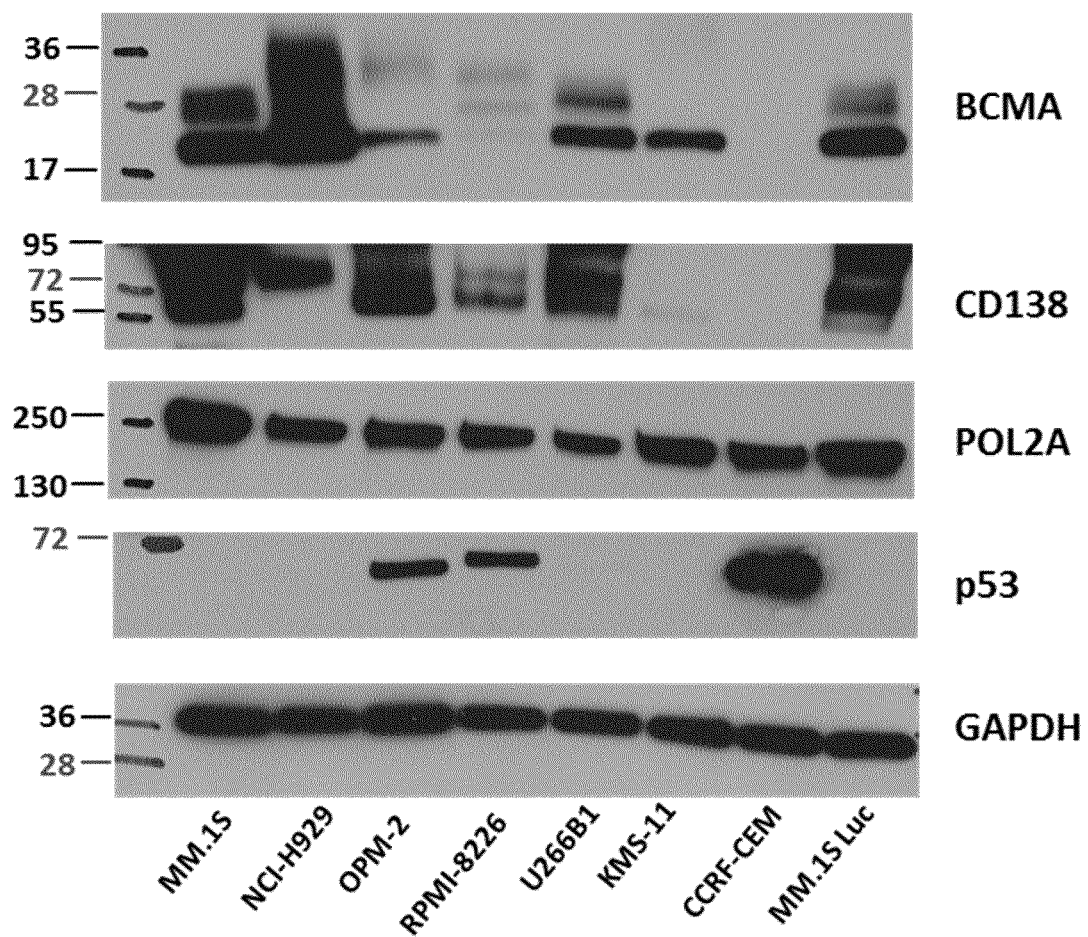
FIG. 19 shows BCMA expression levels on different cell lines used for cytotoxicity assays. Western Blot analyses using antibodies against BCMA, CD138, RNA polymerase 2A (POLR2A), p53 and GAPDH (control). All cell lines express BCMA, except for CCRF-CEM which was used a BCMA-negative cell line. Highest BCMA levels are detected in NCI-H929 cells, lowest in RPMI-8226 cells.
Figure 20:
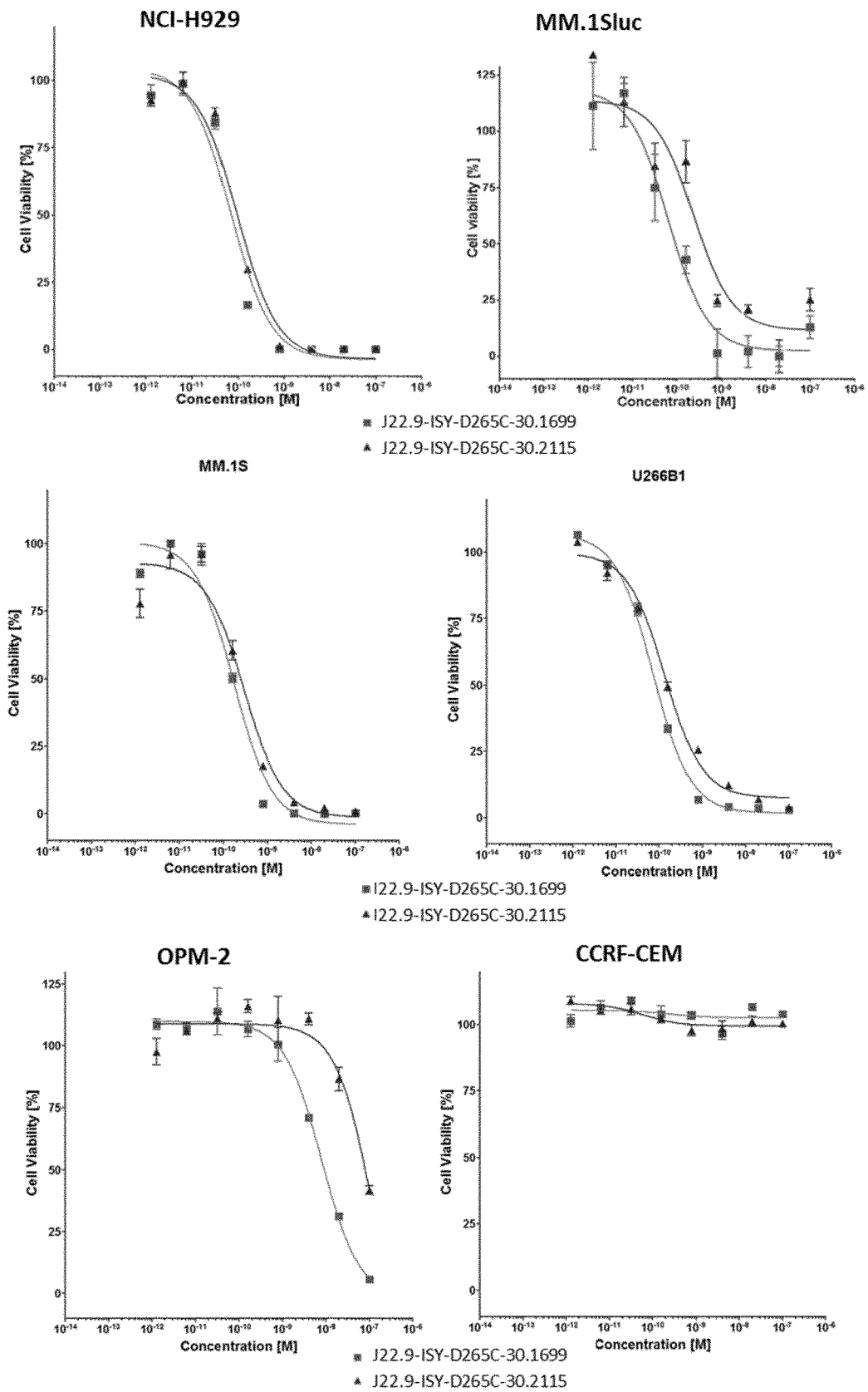
FIG. 20 shows results from cellular cytotoxicity experiments: Viability of BCMA-positive (NCI-H929, MM.1S, MM.1S Luc, U266B1, OPM-2) and BCMA-negative (CCRF-CEM) cells after incubation for 96 hours with J22.9-ISY-D265C-30.1699 and J22.9-ISY-D265C-30.2115 was monitored. Cytotoxicity was calculated as half maximal effective concentration ($EC_{50}$).

Cytotoxicity potentials of both ADCs were tested on five BCMA-positive MM cell lines (NCI-H929, MM.1S Luc, MM.1S, U266B1, and OPM-2) and one BCMA-negative control cell line (CCRF-CEM). Both ADCs show high cytotoxic activity in the picomolar range with slightly superior toxicity of J22.9-ISY-D265C-30.1699 on some cell lines. Cytotoxicity of J22.9-ADCs is strongly dependent on BCMA-expression levels on cell surface with no toxicity observed in non-BCMA expressing control cells. In addition, with both amanitin-ADCs low $EC_{50}$ values on OPM-2 cells correlate with poor BCMA-expression (see Table 3/FIG. 19 and Table 4/FIG. 20).

TABLE 2

| Cell line | | CD269 protein (Western blot) | CD138 protein (Western blot) | J22.9-ISY binding (FACS) |
|---|---|---|---|---|
| MM.1S | Multiple myeloma cell (B lymphoblast) established from the bone marrow of a 55-year-old man with plasma cell leukemia at relapse after chemotherapy | ++ | +++ | ++ |
| MM.1S Luc | MM.1S cells expressing luciferase | ++ | +++ | ++ |
| NCI-H929 | Multiple myeloma cell (B lymphoblast) cell established from a 62-year-old white woman with myeloma at relapse | +++ | ++ | +++ |
| U266B1 | Multiple myeloma cell (B lymphoblast) cell derived from peripheral blood of a 53-year-old patient with an IgE myeloma | ++ | +++ | + |
| OPM-2 | Multiple myeloma cell (B lymphoblast) cell established from the peripheral blood of a 56-year-old woman with multiple myeloma (IgG lambda) in leukemic phase (relapse, terminal) | + | +++ | + |
| KMS-11 | Multiple myeloma cell (B lymphoblast) cell established from patient with multiple myeloma | + | +/− | + |
| RPMI-8226 | Multiple myeloma cell (B lymphoblast) cell established from the peripheral blood of a 61-year-old man with multiple myeloma | +/− | + | + |
| CCRF-CEM | T lymphoblastoid line established from the peripheral blood of a 3-year-old Caucasian girl with acute lymphoblastic leukemia (ALL) at relapse (control cell line) | − | − | − |

TABLE 4

| $EC_{50}$ [M]: | NCI-H929 | MM.1S Luc | MM.1S | U266B1 | OPM-2 |
|---|---|---|---|---|---|
| J22.9-ISY-D265C-30.1699 | $7.0 \times 10^{-11}$ | $6.5 \times 10^{-11}$ | $1.7 \times 10^{-10}$ | $7.3 \times 10^{-11}$ | $7.9 \times 10^{-9}$ |
| J22.9-ISY-D265C-30.2115 | $9.7 \times 10^{-11}$ | $2.3 \times 10^{-10}$ | $2.9 \times 10^{-10}$ | $1.4 \times 10^{-10}$ | $1.4 \times 10^{-7}$ |

Example 6

In-Vivo Pharmacological Activity in Multiple Myeloma Xenograft Model

1. Subcutaneous Xenograft Model
Single Dosing

Antitumor activity of J22.9-ISY-D265C-30.2115 and J22.9-ISY-D265C-30.1699 was tested in a subcutaneous NCI-H929 (see Table 3 for details of cell line) mouse xenograft model.

Figure 21:
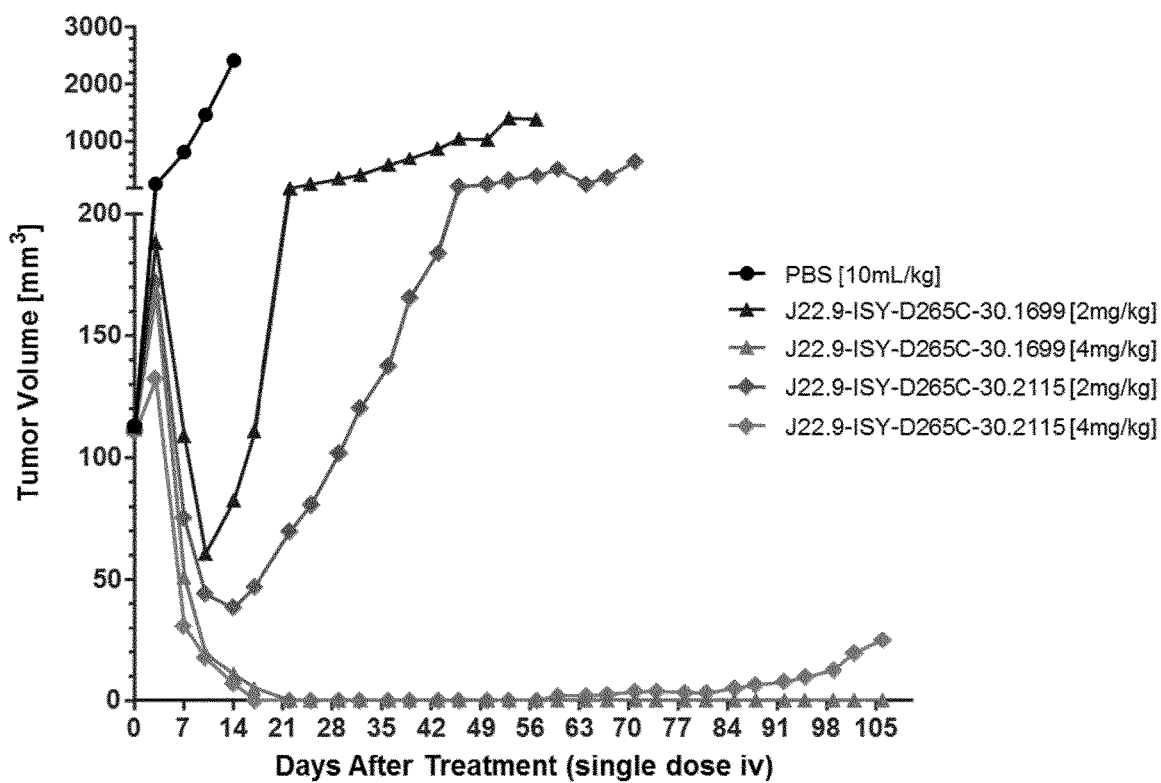
FIG. 21 shows the antitumor activity in mouse NCI-H929 subcutaneous xenograft in single dose application: Female CB-17 Scid mice were subcutaneously inoculated with 5×10⁶ NCI-H929 cells. Once tumor volume reached 80 mm³, mice (8 animals per group) were treated intravenously with single doses (2 or 4 mg/kg) of J22.9-ISY-D265C-30.2115 or J22.9-ISY-D265C-30.1699, or were treated with PBS as control.. Tumor volumes were monitored twice per week.

Single treatment with 2 mg/kg doses resulted in initial response followed by regrowth of tumor in 7 of 8 mice for J22.9-ISY-D265C-30.1699 and 6 of 8 mice for J22.9-ISY-D265C-30.2115. At 4 mg/kg doses, complete tumor remission was reached in 8 of 8 mice for J22.9-ISY-D265C-30.1699 and 7 of 8 mice for J22.9-ISY-D265C-30.2115 and mice stayed tumor free for more than 100 days (the time course of the experiment). At doses of 2 mg/kg J22.9-ISY-D265C-30.2115 showed slightly superior anti-tumor efficacy compared to J22.9-ISY-D265C-30.1699. No statistically significant body weight reduction was observed, except for J22.9-ISY-D265C-30.1699 at 4 mg/kg doses (see FIG. 21).

Repeated Dosing

The efficacy of drug substance J22.9-ISY-D265C-30.2115 was further evaluated in a repeated dose setting in the subcutaneous NCI-H929 xenograft model. Compared to the single dose application described above, doses were reduced to 1, 0.5 and 0.25 mg/kg and applied either once per week (1×/week), every two weeks (1×/2 weeks) or every three weeks (1×/3 weeks). Repeatedly applied doses of 1 mg/kg already resulted in tumor regression, and with repeated 2 mg/kg dosing complete tumor remission could be observed (see FIG. 22).

2. Intravenous Xenograft Model

Single Dosing

Figure 23:
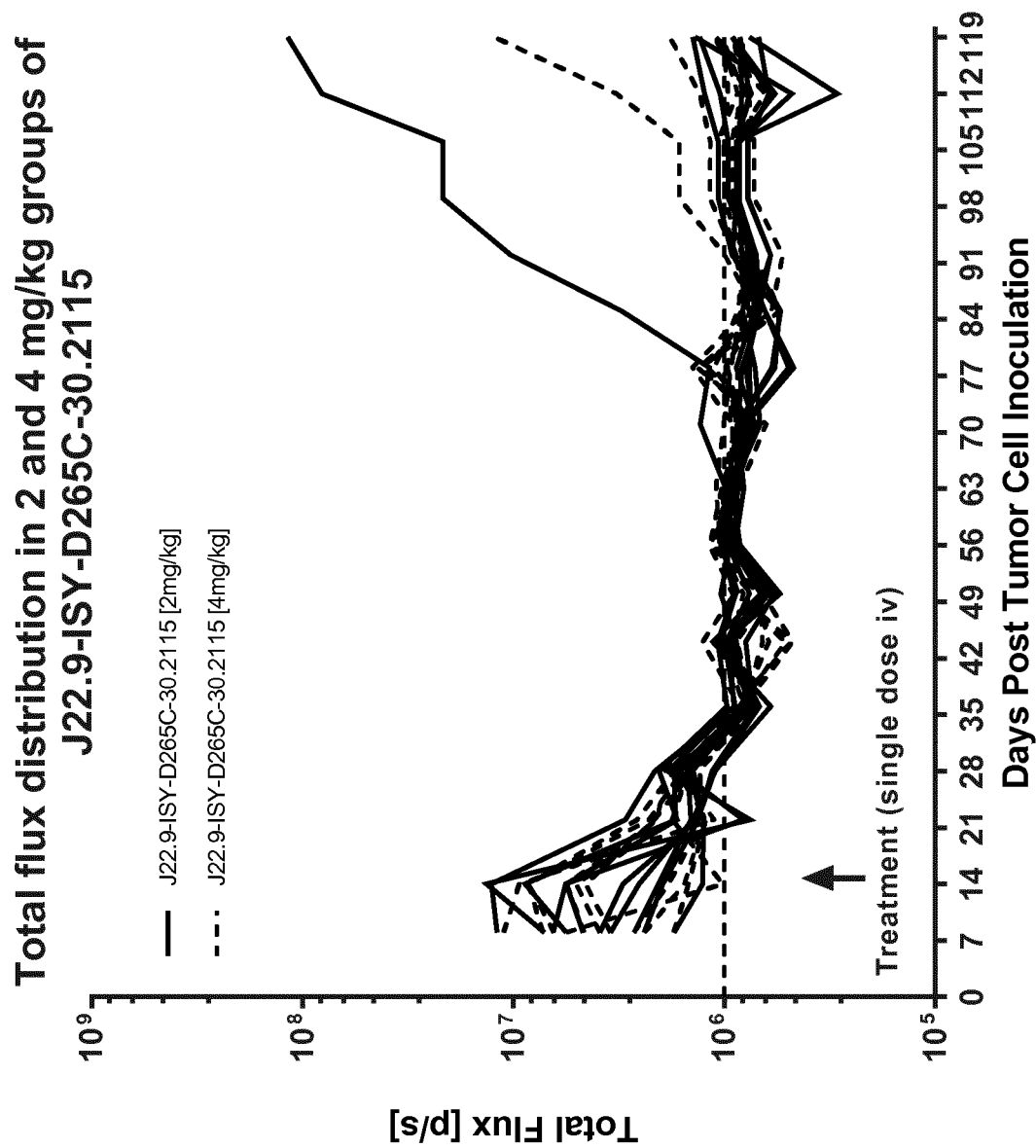
FIG. 23 shows the antitumor activity in disseminating MM.1S Luc xenograft model: (A) Female SCID beige mice were intravenously injected with 1×10⁷ MM.1S Luc cells. When reaching a mean flux of 1.5×10⁶-1×10⁷ (10-14 days after implantation) 8-10 mice per group were treated with single doses (2 and 4 mg/kg) of J22.9-ISY-D265C-30.1699, J22.9-ISY-D265C-30.2115 or PBS as control. Luciferase activity was monitored by non-invasive bio-imaging twice weekly, 10 minutes after administration of luciferin (10 µl/g body weight). (B) Individual tumor growth curves for each animal are depicted. Individual Growth curves are shown for groups treated with 2 mg/kg (solid line) and 4 mg/kg (dashed line) of J22.9-ISY-D265C-30.2115. Data indicate that only one animal from each depicted group shows elevated tumor signals significantly above background level.

The antitumor activity of J22.9-ISY-D265C-30.1699 and J22.9-ISY-D265C-30.2115 was further tested in a disseminating intravenous MM.1S Luc xenograft model at doses of 2 and 4 mg/kg. Both compounds showed very effective and comparable antitumor activity with complete tumor remission for more than 100 days (see FIG. 23A). Only 1 of 10 mice for both compounds showed slight regrowth of tumor after initial response for over 90 days(see FIG. 23B).

Figure 24:
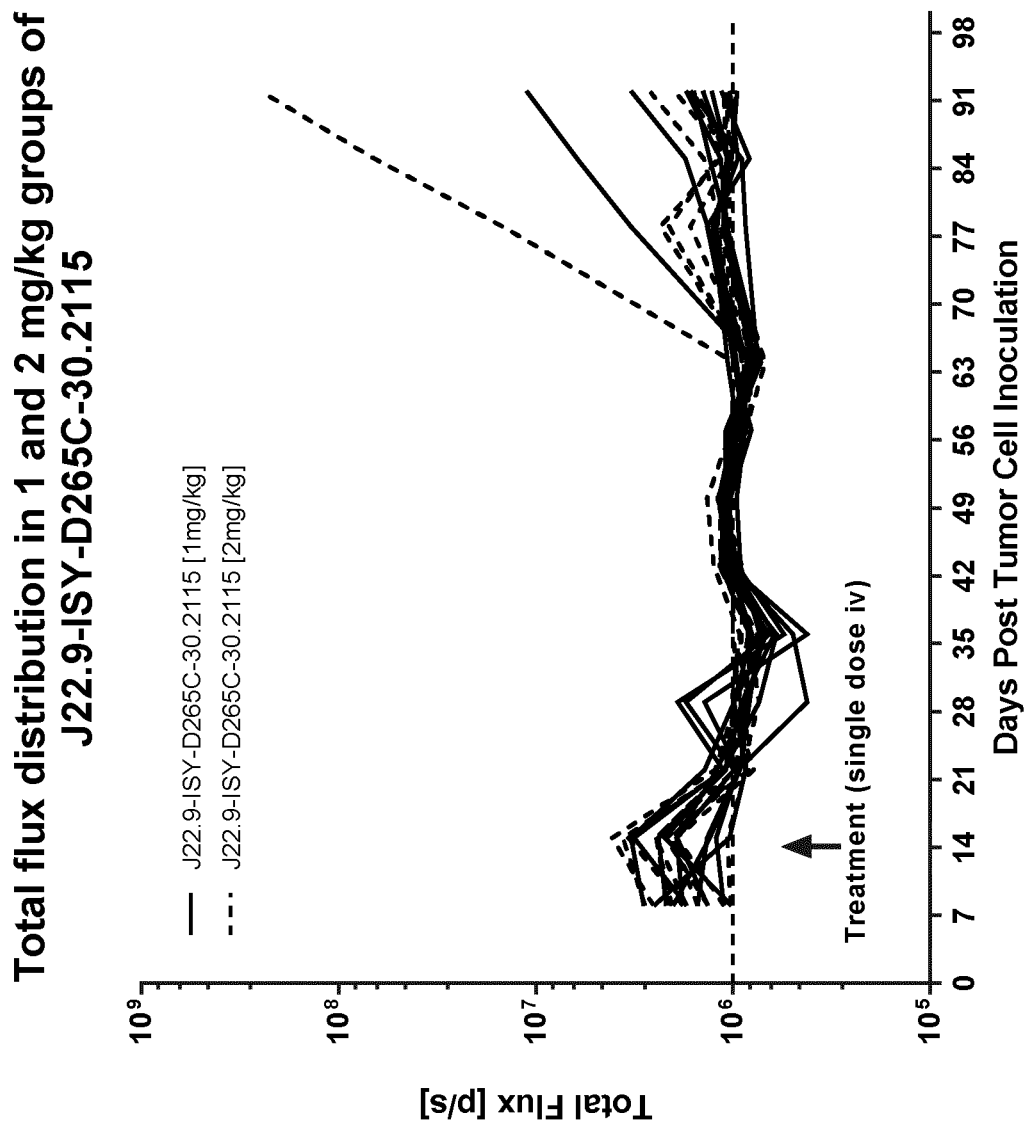
FIG. 24 shows the antitumor activity in a disseminating MM.1S Luc xenograft model: dose reduction: (A) Female SCID beige mice were intravenously injected with 1×10⁷ MM.1S Luc cells. When reaching a mean flux of 1.5×10⁶-1×10⁷ (10-14 days after implantation) 8-10 mice per group were treated with single doses (0.1, 0.3, 1 and 2 mg/kg) of J22.9-ISY-D265C-30.2115 or PBS as control. Luciferase activity was monitored by non-invasive bio-imaging twice weekly, 10 minutes after administration of luciferin (10 µl/g body weight). (B) Individual tumor growth curves for each animal are depicted. Growth curves are shown for groups treated with 1 mg/kg (solid line) and 2 mg/kg (dashed line) of J22.9-ISY-D265C-30.2115. Data indicate that only one animal from each depicted group shows elevated tumor signals significantly above background level.

In the disseminating MM.1S Luc xenograft model doses of drug substance J22.9-ISY-D265C-30.2115 were further reduced to single dose application of 1, 0.3 and 0.1 mg/kg. Already single dose application of 0.3 mg/kg resulted in complete tumor eradication (see FIG. 24).

Example 7

Non-Human Primate (NHP) Tolerability Study

Figure 25:
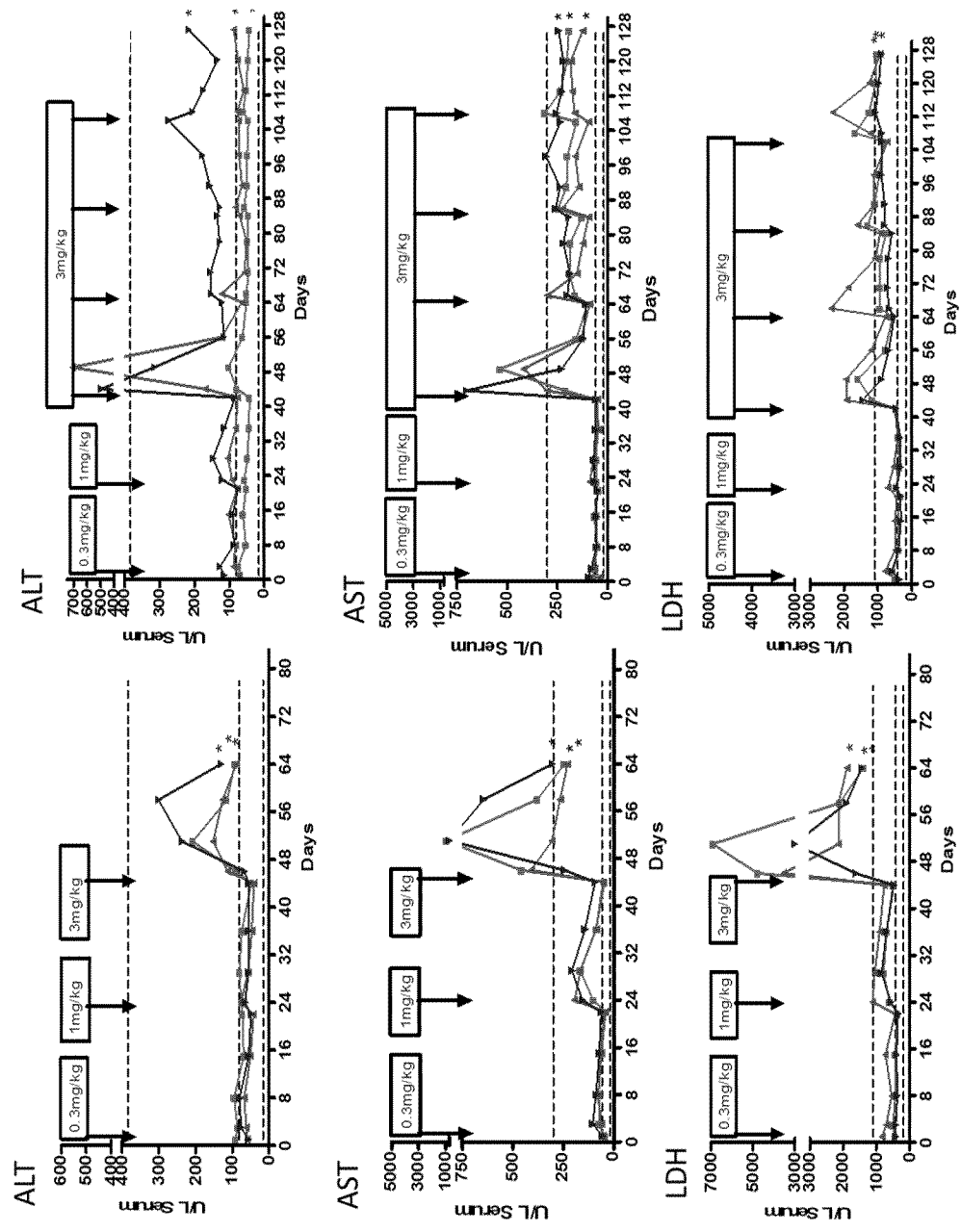
FIG. 25 shows the results from a tolerability study in cynomolgus monkeys: Groups of 3 animals were injected with J22.9-ISY-D265C-30.2115 or J22.9-ISY-D265C-30.1699 in escalating doses (0.3, 1 and 3 mg/kg) followed by repeated dosing using 3 mg/kg. ALT: alanine transaminase; AST: aspartate transaminase; LDH: lactate dehydrogenase.

J22.9-ISY-D265C-30.2115 and J22.9-ISY-D265C-30.1699 were assessed for a dose-escalating tolerability study in cynomolgus monkeys. Groups of 3 animals were injected with J22.9-ISY-D265C-30.1699 at days 1 (0.3 mg/kg), 22 (1 mg/kg), and 44 (3 mg/kg), or with J22.9-ISY-D265C-30.2115 at days 1 (0.3 mg/kg), 21 (1 mg/kg), and 42, 64, 84, 106 (3 mg/kg each time point). Animals were monitored over time for biochemical and haematological blood parameters (see FIG. 25), urinalysis, body weight, food consumption, clinical signs and mortality. In addition, blood samples were collected for pharmacokinetic studies. At the end of the experiments tissue samples are used for histopathological examinations.

Up to 3 mg/kg doses of both compounds were well tolerated with no signs of kidney damage by serum parameters and unaffected body weight and food consumption. Doses of 3 mg/kg resulted in increased but transient levels of liver enzymes (ALT, AST) and the unspecific inflammatory marker LDH. Repeated dosing of 3 mg/kg J22.9-ISY-D265C-30.2115 did not result in further increase of liver enzymes or LDH.

Example 7

Figure 26A:
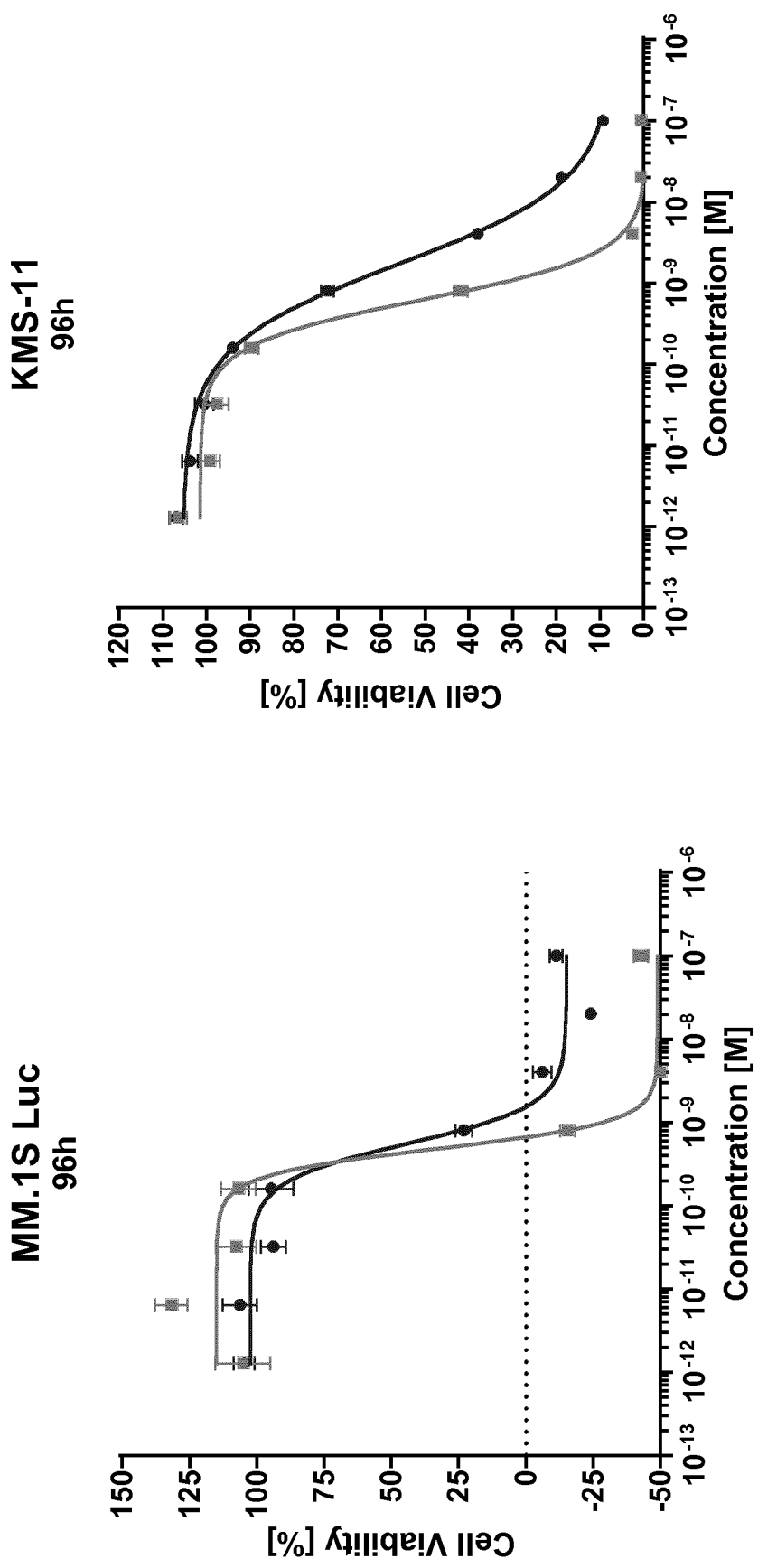
FIG. 26 shows a comparison of the cytotoxic potential of J22.9-ISY-D265C-30.2115 (●) with the monomethyl auristatin F derivative J22.9-ISY-MMAF (■) on MM.1S Luc (left panel) and KMS-11 cells (right panel): (A) comparison at time point 96 h, $EC_{50}$ of J22.9-ISY-D265C-30.2115: 5.575 $10^{-10}$ M on MM.1S Luc cells; 1.716 $10^{-9}$ Mon KMS.-11 cells; $EC_{50}$ of J22.9-ISY-MMAF: 4.812 $10^{-10}$ M on MM.1S Luc cells; 6.261 $10^{-10}$ M on KMS-11 cells; (B) time course 24 h to 120 h of cytotoxic potential on MM.1S Luc cells (J22.9-ISY-D265C-30.2115: ●; J22.9-ISY-MMAF: ■); (C) time course 24 h to 120 h of cytotoxic potential on KMS-11 cells (J22.9-ISY-D265C-30.2115: ●; J22.9-ISY-MMAF: ■).
Figure 26B:
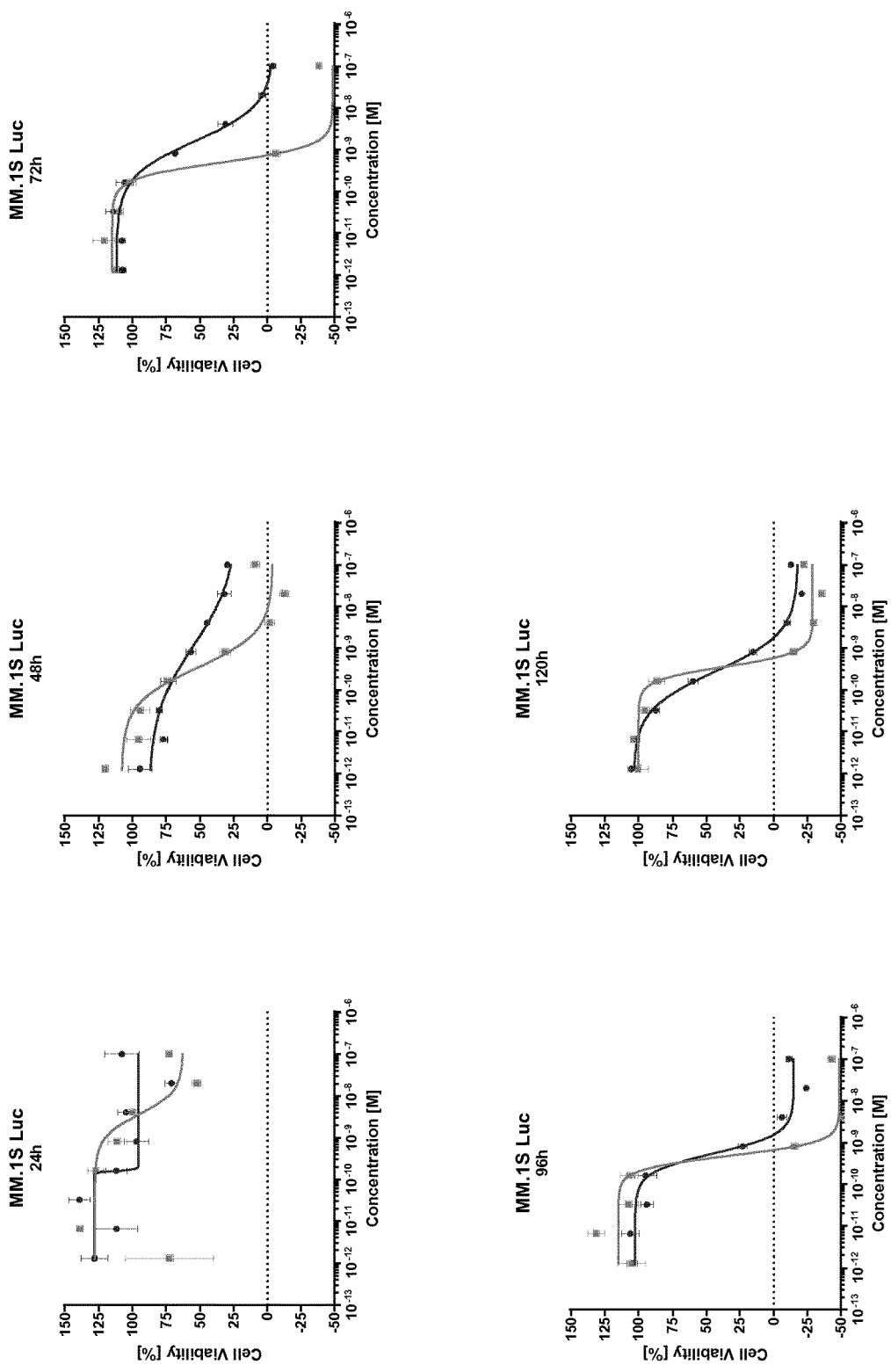

Cytotoxic Potential of J22.9-ISY-D265C-30.2115 in Comparison to Monomethyl Auristatin F Derivative Cytotoxicity potentials of J22.9-ISY-D265C-30.2115 was compared to the interchain conjugate J22.9-ISY-MMAF on two BCMA-positive MM cell lines (MM.1S Luc, and KMS-11). Both ADCs show high cytotoxic activity in the picomolar range after 96 h with slightly superior toxicity of J22.9-ISY-MMAF (see FIG. 26A). The efficacy of both compounds was compared in a timeline experiment on the two cell lines. Cytotoxicity was measured after 24, 46, 72, 96, and 120 hours (see FIGS. 26B+26C). J22.9-ISY-D265C-30.2115 unfolded the full cytotoxicity after 96 and 120 hours, whereas the MMAF conjugate showed already after 48 and 72 hours a full blown cytotoxic potential. This indicates that the amanitin derivative needs more time to unfold its cytotoxic potential and to drive the cells into apoptosis due to its mode of action than MMAF.

Example 8

Efficacy of J22.9-ISY-D265C-30.2115 in a Disseminating Xenograft Model

Figure 26C:
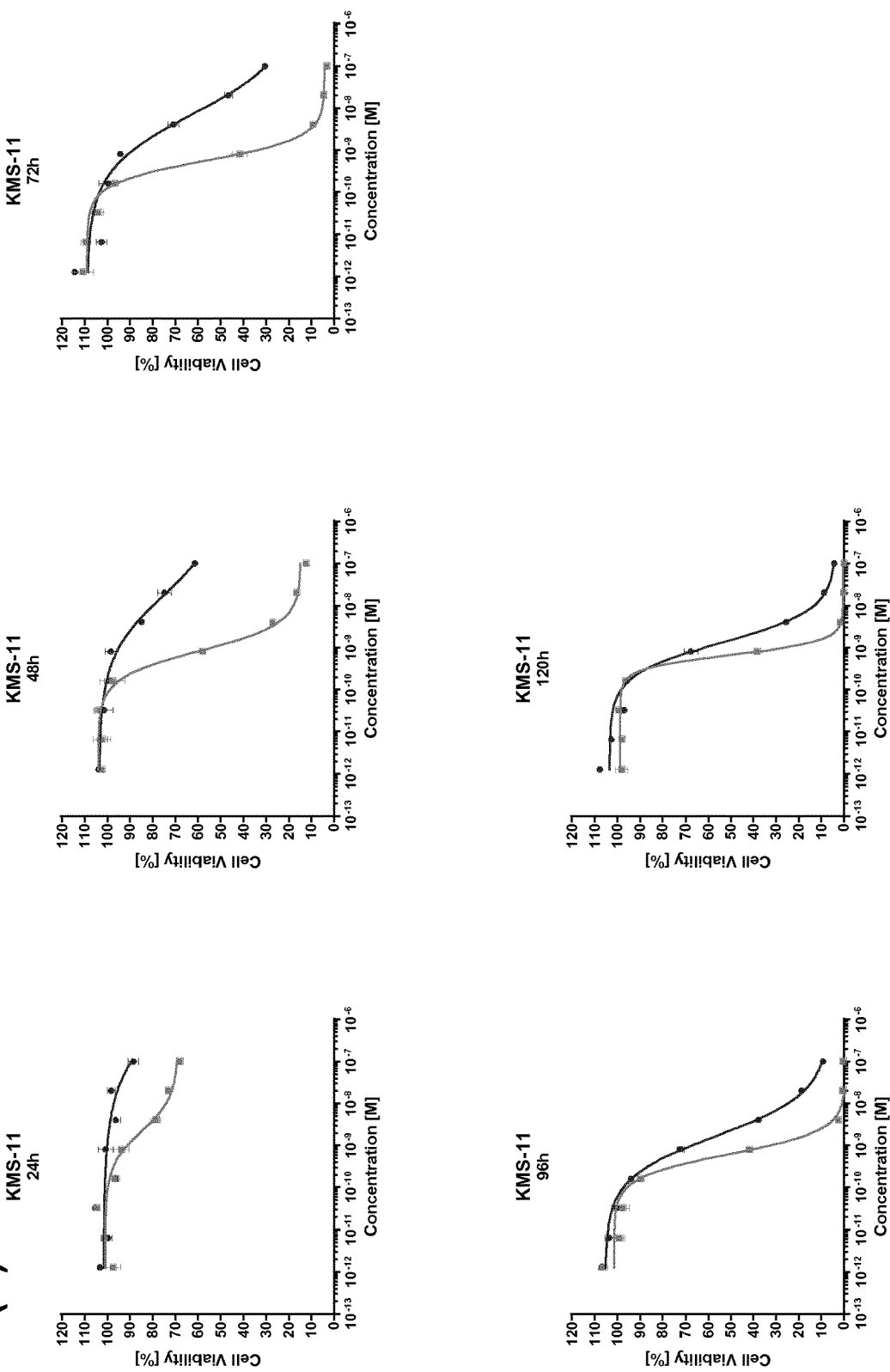
Figure 27:
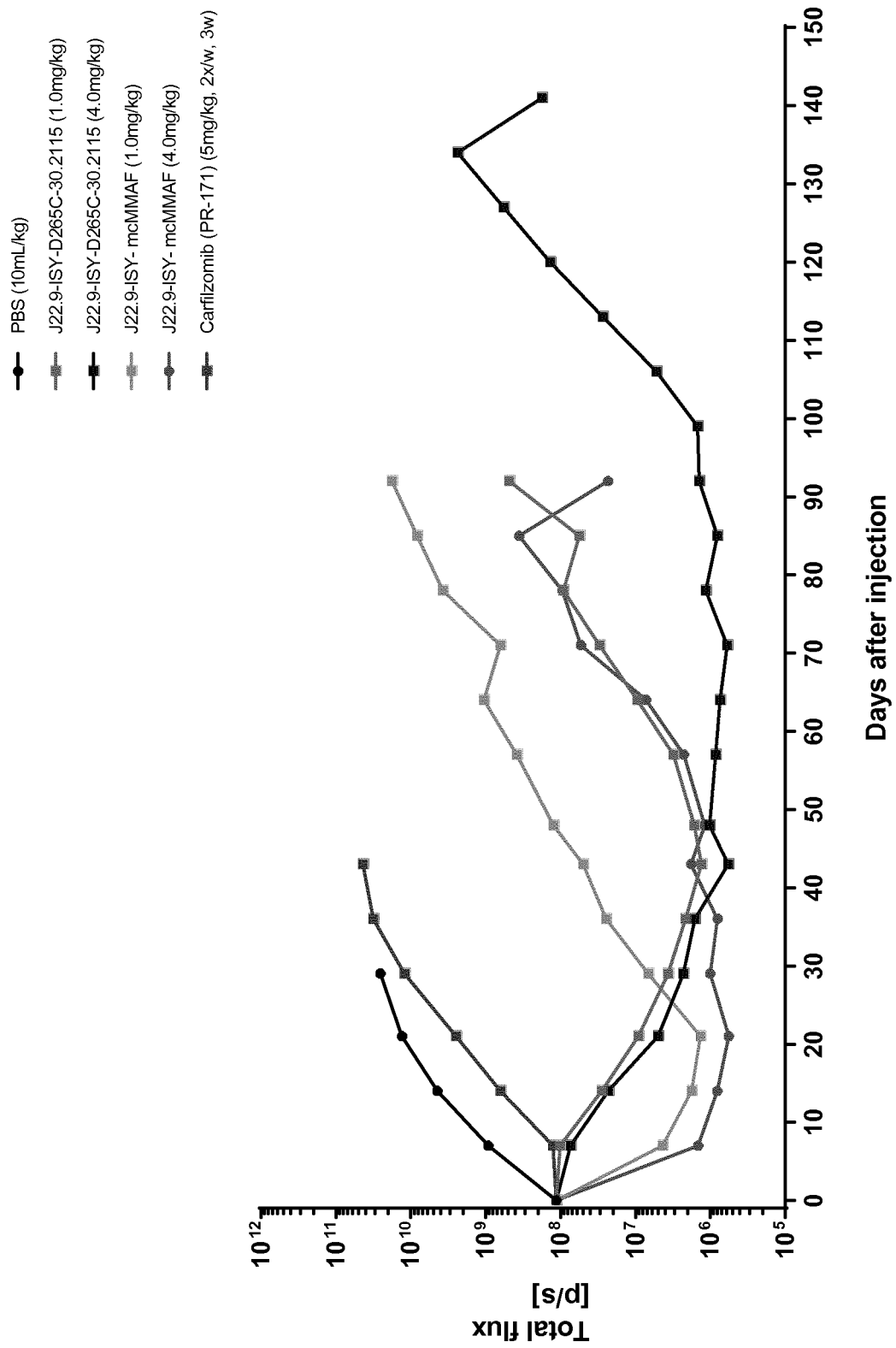
FIG. 27 shows the results from a study of the efficacy of J22.9-ISY-D265C-30.2115 in comparison with the monomethyl auristatin F derivative J22.9-ISY-MMAF and Carfilzomib in a disseminating Xenograft model (MM.1S Luc).

The antitumor activity of J22.9-ISY-D265C-30.2115 was compared to the interchain conjugate J22.9-ISY-MMAF in a disseminating intravenous MM.1S Luc xenograft model at doses of 1 and 4 mg/kg. The MMAF conjugate showed a very fast initial response after five days at both doses and a regrowth of the tumor after 20 and 50 days, respectively. J22.9-ISY-D265C-30.2115 in contrast showed a slower initial response after 10 days at both doses, but a longer period until regrowth of the tumor after 50 and 100 days, respectively (see FIG. 27). Thus, the amatoxin conjugate showed a better efficacy in terms of tumor free survival despite its slower onset of action (see FIGS. 26(A) to (C)).

REFERENCES

Ackerman M E et al. A robust, high-throughput assay to determine the phagocytic activity of clinical antibody samples. J Immunol Methods. 2011 Mar. 7; 366(1-2): 8-19.

Baudino L et al. Crucial role of aspartic acid at position 265 in the CH2 domain for murine IgG2a and IgG2b Fc-associated effector functions. J Immunol. 2008 Nov. 1; 181(9):6664-9.

Belucci R et al. Graft-versus-tumor response in patients with multiple myeloma is associated with antibody response to BCMA, a plasma-cell membrane receptor. Blood. 2005 May 15; 105(10):3945-5

Bird J M et al. Guidelines for the diagnosis and management of multiple myeloma 2011. Br J Haematol. 2011 July; 154(1):32-75

Bossen C, Schneider P. BAFF, APRIL and their receptors: structure, function and signaling. Semin Immunol. 2006 October; 18(5):263-75

Chesi M, Bergsagel P L. Advances in the pathogenesis of multiple myeloma. Int J Lab Hematol. 2015 May; 37 Suppl 1:108-14

Davis M B, Preston J F. A Conjugate of α-amanitin and Monoclonal Immunoglobulin G to Thy 1.2 Antigen is Selectively Toxic to T Lymphoma Cells. Science 213 (1981) 1385-1388

Dimopoulos M A et al. Current treatment landscape for relapsed and/or refractory multiple myeloma. Nat Rev Clin Oncol. 2015 January; 12(1):42-54

Dimopoulos M A et al. Pathogenesis and treatment of renal failure in multiple myeloma. Leukemia. 2008 August; 22(8):1485-93

Hayes J M et al. Glycosylation and Fc receptors. Curr Top Microbiol Immunol. 2014; 382:165-99

Kuehl W M, Bergsagel P L. Molecular pathogenesis of multiple myeloma and its premalignant precursor. J Clin Invest. 2012 October; 122(10):3456-63

Leukemia. 2009 January; 23(1):3-9

Kyle R A, Rajkumar S V. Multiple myeloma. N Engl J Med. 2004 Oct. 28; 351(18):1860-73.

Marino S F, Olal D, Daumke O. A complex water network contributes to high-affinity binding in an antibody-antigen interface. Data Brief. 2015 Dec. 19; 6:394-7

Morris P W, Venton D L. Regiospecific amine substitution into a-amanitin with retention of inhibitory properties against eukaryotic class II RNA polymerase. Int. J. Peptide Protein Res. 21 (1983) 419-430

Oden et al. Potent anti-tumor response by targeting B cell maturation antigen (BCMA) in a mouse model of multiple myeloma. Mol Oncol. 2015 August; 9(7):1348-5

Peters C, Brown S. Antibody-drug conjugates as novel anti-cancer chemotherapeutics. Biosci Rep. 2015 Jun. 12; 35(4).

Rajkumar S V et al. International Myeloma Working Group updated criteria for the diagnosis of multiple myeloma. Lancet Oncol. 2014 November; 15(12):e538-4

Rickert R C et al. Signaling by the tumor necrosis factor receptor superfamily in B-cell biology and disease. Immunol Rev. 2011 November; 244(1):115-33

Sanchez et al. Serum B-cell maturation antigen is elevated in multiple myeloma and correlates with disease status and survival. Br J Haematol. 2012 September; 158(6): 727-38

Shaffer A L et al. IRF4 addiction in multiple myeloma. Nature. 2008 Jul. 10; 454(7201):226-31

Shields R L et al. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001 Mar. 2; 276(9):6591-604

Trail P A. Antibody drug conjugates as cancer therapeutics. Antibodies 2013, 2(1), 113-129.

Wieland T, Faulstich H. Amatoxins, phallotoxins, phallolysin, and antamanide: the biologically active components of poisonous Amanita mushrooms. CRC Crit Rev Biochem. 1978 December; 5(3):185-260

Zhao L, May J P, Blanc A, Dr. Dietrich D J, Loonchanta A, Matinkhoo K, Pryyma A, and Perrin D M. Synthesis of a Cytotoxic Amanitin for Biorthogonal Conjugation. ChemBioChem 16 (2015) 1420-1425

SEQUENCES

Humanized J22.9 heavy chain J22.9-ISY-D265C (SEQ ID NO: 1):
EVQLVESGGG LVQPGGSLRL SCAASGFTFS RYWISWVRQA

PGKGLVWVGE INPSSSTINY APSLKDKFTI SRDNAKNTLY

LQMNSLRAED TAVYYCASLY YDYGDAYDYW GQGTLVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVCVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPGK

Humanized J22.9 light chain (SEQ ID NO: 2):
EIVMTQSPAT LSVSPGERAT LSCKASQSVE SNVAWYQQKP

GQAPRALIYS ASLRFSGIPA RFSGSGSGTE FTLTISSLQS

EDFAVYYCQQ YNNYPLTFGA GTKLELKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC

The invention claimed is:

1. A conjugate according to Formula I comprising (a) an amatoxin; (b) a BCMA-binding moiety comprising the antibody heavy chain according to SEQ ID NO: 1 and the antibody light chain according to SEQ ID NO: 2, wherein the, heavy chain constant region of the antibody heavy chain sequence comprises a D265C mutation (J22.9-ISY-D265C); and (c) a protease-cleavable linker, wherein said BCMA-binding moiety is attached to said linker via the thiol group of the cysteine residue at position 265 in the antibody heavy chain, wherein said amatoxin is characterized by comprising (i) an amino acid 4 with a 6'-deoxy position; and (ii) an amino acid 8 with an S-deoxyposition Formula I
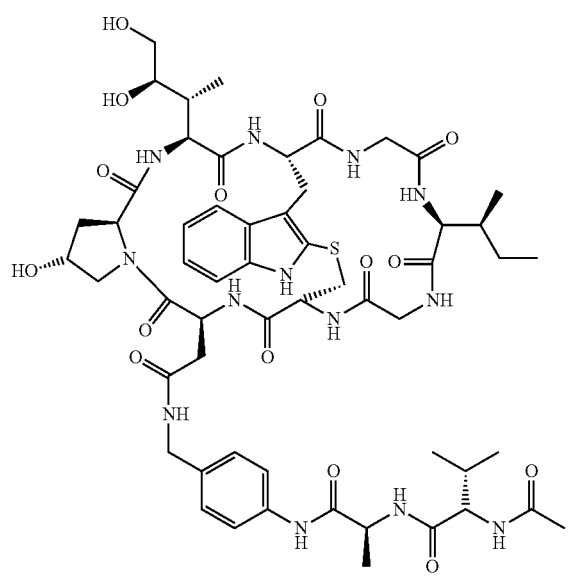
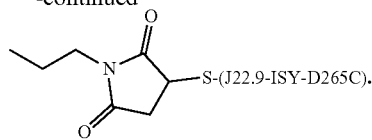
2. A pharmaceutical composition comprising the conjugate of claim 1.
3. A method of treating cancer in a patient, the method comprising administering to the patient the conjugate of claim 1, wherein the cancer is selected from the group consisting of multiple myeloma, diffuse large B-cell lymphoma (DLBCL), and chronic lymphocytic leukemia (CLL).
* * * * *